United States Patent
Taylor et al.

(10) Patent No.: US 11,248,051 B2
(45) Date of Patent: *Feb. 15, 2022

(54) ADMINISTRATION OF AGENTS FOR THE TREATMENT OF INFLAMMATION

(71) Applicant: Biogen MA Inc., Cambridge, MA (US)

(72) Inventors: Julie Taylor, San Francisco, CA (US); Theodore A. Yednock, Forest Knolls, CA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,042

(22) Filed: May 13, 2019

(65) Prior Publication Data

US 2020/0148773 A1  May 14, 2020

Related U.S. Application Data

(60) Continuation of application No. 15/586,724, filed on May 4, 2017, now abandoned, which is a continuation of application No. 14/613,821, filed on Feb. 4, 2015, now abandoned, which is a continuation of application No. 12/846,350, filed on Jul. 29, 2010, now abandoned, which is a division of application No. 11/540,640, filed on Oct. 2, 2006, now Pat. No. 7,807,167, which is a division of application No. 10/372,111, filed on Feb. 25, 2003, now abandoned.

(60) Provisional application No. 60/374,501, filed on Apr. 23, 2002, provisional application No. 60/360,134, filed on Feb. 25, 2002.

(51) Int. Cl.

| A61K 39/395 | (2006.01) |
| A61K 39/00 | (2006.01) |
| A61K 49/00 | (2006.01) |
| C07K 16/28 | (2006.01) |
| A61K 45/06 | (2006.01) |
| G01N 33/569 | (2006.01) |

(52) U.S. Cl.
CPC ...... *C07K 16/2839* (2013.01); *A61K 39/3955* (2013.01); *A61K 45/06* (2013.01); *C07K 16/2842* (2013.01); *G01N 33/56966* (2013.01); *A61K 2039/505* (2013.01); *A61K 2039/507* (2013.01); *A61K 2039/545* (2013.01); *C07K 2317/24* (2013.01); *C07K 2317/76* (2013.01); *G01N 2333/4737* (2013.01); *G01N 2333/7055* (2013.01)

(58) Field of Classification Search
None
See application file for complete search history.

(56) References Cited

U.S. PATENT DOCUMENTS

| 5,260,210 A | 11/1993 | Rubin et al. |
| 5,716,648 A | 2/1998 | Halskov et al. |
| 5,730,978 A | 3/1998 | Wayner |
| 5,840,299 A | 11/1998 | Bendig et al. |
| 5,932,214 A | 8/1999 | Lobb et al. |
| 6,001,809 A | 12/1999 | Thorsett et al. |
| 6,033,665 A | 3/2000 | Yednock |
| 6,602,885 B2 | 8/2003 | Baroudy et al. |
| 7,807,167 B2 | 10/2010 | Taylor et al. |
| 7,972,775 B2 * | 7/2011 | Rubin .............. G01N 33/56983 435/5 |
| 8,124,350 B2 | 2/2012 | Subramanyam et al. |
| 8,815,236 B2 | 8/2014 | Burke et al. |
| 8,871,449 B2 | 10/2014 | Subramanyam et al. |
| 9,493,567 B2 * | 11/2016 | Lieberburg ........ A61K 49/0004 |
| 9,709,575 B2 | 7/2017 | Subramanyam et al. |
| 10,233,245 B2 * | 3/2019 | Lieberburg ............ A61K 38/03 |
| 2001/0046496 A1 | 11/2001 | Brettman et al. |
| 2005/0215565 A1 | 9/2005 | Karlik et al. |

FOREIGN PATENT DOCUMENTS

| EP | 1485127 | 6/2011 |
| JP | 3-7237 | 1/1991 |
| JP | 9-500617 | 1/1997 |
| JP | 9/508272 | 8/1997 |
| WO | WO 90/07861 | 7/1990 |
| WO | WO 91/03252 | 3/1991 |
| WO | WO 92/15683 | 9/1992 |
| WO | WO 93/15764 | 8/1993 |
| WO | WO 94/16094 | 7/1994 |
| WO | WO 94/28911 | 12/1994 |
| WO | WO 95/19790 | 1/1995 |
| WO | WO 96/01644 | 1/1996 |
| WO | WO 97/18838 | 5/1997 |

(Continued)

OTHER PUBLICATIONS

Tubridy et al. The effect of anti-alpha4 integrin antibody on brain lesion activity in MS. The UK Antegren Study Group. Neurology. Aug. 11, 1999; 53(3):466-72. (Year: 1999).*

(Continued)

*Primary Examiner* — Maher M Haddad
(74) *Attorney, Agent, or Firm* — Todd Lorenz

(57) ABSTRACT

A method of chronically reducing a patient's pathological inflammation via the administration of an agent that specifically binds to an alpha-4 integrin or a dimer comprising an alpha-4 integrin is disclosed. The agent provided must have a binding affinity such that administration is sufficient to suppress pathological inflammation, and the agent is administered chronically to provide long-term suppression of pathological inflammation.

7 Claims, 19 Drawing Sheets

Specification includes a Sequence Listing.

(56) References Cited

FOREIGN PATENT DOCUMENTS

| WO | WO 98/30227 | 7/1998 |
|---|---|---|
| WO | WO 98/53817 | 12/1998 |
| WO | WO 00/44408 | 8/2000 |
| WO | WO 01/85797 | 11/2001 |
| WO | WO 03/072040 | 9/2003 |

OTHER PUBLICATIONS

Athena Neurosciences. Antibody against alpha-4 integrin reverses signs of active disease in multiple sclerosis model. Press Release; Nov. 14, 1994. (Year: 1994).*
Kent et al A monoclonal Antibody to α4-Integrin Reverses the MR-Detectable Signs of Experimental Allergic Encephalomyelitis in the Guinea Pig. JMRI 1995, 5:535-540. (Year: 1995).*
Andersson et al., "Glucocorticosteroid therapy for multiple sclerosis: a critical review", Journal Neurological Sciences 160:16-25, 1998.
Antergren Publication Committee, "A randomized, double-blind, placebo-controlled, pan-European study of a recombinant humanised antibody to alpha4 integrin (Antegren TM) in moderate to severely active Crohn's disease", Gastroenterology 12(5 Suppl. 1):A127-A128, 2001.
Asakura, H., "Treatment of ulcerative colitis and Crohn's disease with monoclonal antibody", Japanese Journal of Clinical Medicine 60(3)531-538, 2002 (abstract in English).
Bergsteinsdottir et al., "Evidence for common autoimmune disease genes controlling onset, severity, and chronicity based on experimental models for multiple sclerosis and rheumatoid arthritis", Journal of Immunology 1564-1568, 2000.
Bevilacqua et al., "Endothelial-leukocyte Adhesion Molecules", Annu. Rev. Immunol., vol. 11, pp. 767-804 (1993).
Bjursten et al., "Long-term treatment with anti-alpha 4 integrin antibodies aggravates colitis in G-12 defecient mice", Eur. J. Immunol. 35(8):2274-2283, 2005.
Briskin et al., Am. J. Pathol., "Human Mucosal Addressing Cell Adhesion Molecule-1 Is Preferentially Expressed in Intestinal Tract and Associated Lymphoid Tissue", vol. 151, pp. 97-110 (1997).
Brocke et al., "Antibodies to CD44 and integrin α4, but not L-selectin, prevent central nervous system inflammation and experimental encephalomyelitis by blocking secondary leukocyte recruitment", Proc. Natl. Acad. Sci USA 96:6896-6901, 1999.
Bryant et al., "Systematic review of immunomodulatory drugs for the treatment of people with multiple sclerosis: Is there good quality evidence on effectiveness and cost?", Journal Neurosurgery & Physchiatry70(5):574-579, 2001.
Butcher et al., "Lymphocyte Homing and Homeostasis", Science, vol. 272, pp. 60-66 (1996).
Cannella et al., "The adhesion molecule and cytokine profile of multiple sclerosis lesions", Ann Neurol. 37:424-435, 1995.
Carter et al., "A placebo-controlled, pharmacodynamic, pharmacokinetic, tolerability and safety study of three doses of intravenous natalizumab in multiple sclerosis", Neurology 53(3) abstract S50.003, 1999.
Chisholm, P.L. et al., "Monoclonal antibodies to the integrin α-4 subunit inhibit the murine contact hypersensitivity response", Eur. J. Immunology 23(3):686-688, 1993.
Coles et al., "Monoclonal Antibody Treatment Exposes Three Mechanisms Underlying the Clinical Course of Multiple Sclerosis", Ann. Neurol., vol. 46, No. 3, pp. 296-304 (1999).
Corthay, A.et al., "Collagen-induced arthritis development requires αβ T cells but not γδ T cells: studies with T cell-deficient (TCR mutant) mice", International Immunology 11(7):1065-1073, 1999.
Cybulsky et al., "Endothelial expression of a mononuclear leukocyte adhesion molecule during atherogenesis", Science 251:788-791, 1991.
Damle et al., "Costimulation with integrin ligands intercellular adhesion molecule-1 or vascular cell adhesion molecule-1 augments activation-induced death of antigen-specific CD4+ T lymphocytes.", J. Immunol., vol. 151, pp. 2368-2379 (1993).

Dore-Duffy et al., Frontiers in Cerebral Vascular Biology: Transport and its regulation Dreues and Betz(eds)Plenum Press N.Y. pp. 243-248, 1993.
Edwards et al., "Vascular cell adhesion molecule 1 and α4 and β1 integrins in lymphocyte aggregates in Sjogren's syndrome and rheumatoid arthritis", Ann Rheum Dis. 52:806-811, 1993.
El-Gabalawy et al., "Supplement Review. why do we not have a cure for rheumatoid arthritis", Arthritis Res. 4 (suppl 3) S297-S301, 2002.
Elan and Biogen Begin Phase III Clinical Trials of Antegren(R) (Natalizumab) in Multiple Sclerosis and Crohn's Disease, obtained Aug. 8, 2015, from www.mult-sclerosis.org/news/Dec2001/PhaseIIIClinicalTrialsOfAntegren.html.
Extended European Search Report dated Dec. 12, 2011, in EP 10012870.1.
Farstad et al., "Topographic Distribution of Homing Receptors on B and T Cells in Human Gut-Associated Lymphoid Tissue", Am. J. Pathol, vol. 150, pp. 187-199 (1997).
Fischer C. et al., "Lymphocyte-endothelial interactions in inflamed synovia: involvement of several adhesion molecules and integrin epitopes", Scand. J. Immunol.38:158-166, 1993.
Gilden, D.H., "Viruses and Multiple Sclerosis", JAMA 286(24), 2001.
Generini et al., "Therapy of spondylarthropathy in inflammatory bowel disease", Clin. Exp. Rheumatol. 20 (Suppl.28):S88-S94, 2002.
Goodkin et al., "Experimental therapies for multiple sclerosis current status", Cleveland Clinic Journal of Medicine 59(1):63-74, 1992.
Gonzalez-Amaro et al., "Therapeutic anti-integrin (α4 and αL) monoclonal antibodies: two-edged swords?", Immunology 116:289-296, 2005.
Gordon, F., "Randomised double-blind placebo-controlled trial of recombinant humanised antibody to α4 integrin (antegren™) in active crohn's disease", Gastroenterology vol. 118(4 Suppl. 2 part 1)pp. AGA A344, 2000.
Gordon, F., Treatment of active ulcerative colitis with a recombinant humanised antibody to α4 integrin (antegren™) Gastroenterology G3151 p. A726, XP-001024675, 1999.
Gordon et al., "A randomized placebo-controlled trial of a humanized monoclonal antibody to alpha4 integrin in active Crohn's disease", Gastroenterology 121(2):268-274, 2001.
Gordon et al., "Adhesion molecule expression in inflammatory bowel disease (IBD) patients treted with natalizumab (Amtegrem TM) a humanised antibody to alpha 4 integrin". Gastroenterology vol. 118(4) abstract 1857, 2000.
Grober, J.S. et al., "Monocyte-endothelial adhesion in chronic rheumatoid arthritis", J Clin. Invest. 91:2609-2619, 1993.
Harlow E. Lane, "Antibodies a laboratory manual", Cold Spring Harbor NY Lab Press 141-155, 1989.
Holzman, B. et al., "Identification of a murine peyer's patch-specific lymphocyte homing receptor as an integrin molecule with an α chain homologous to human VLA-4α", Cell 56:37-46, 1989.
Humira Product Leaflet, Abbot Labratories https://www.accessdata.fda.gov/drugsatfda_docs/label/2002/adalabb 1...1 (2002).
International Search Report dated Apr. 16, 2004, in PCT/US03/05421.
Issekutz, T.B., "Inhibition of in vivo lymphocyte migration to inflammation and homing to lymphoid tissues by the TA-2 monoclonal antibody", J. Immunology 147(12):4178-4184, 1991.
Issekutz, T.B. et al., "T lymphocyte migration to arthritic joints and dermal inflammation in the rat: differing migration patterns and the involvement of VLA-4", Clinical Immunology Immunopathology 61:436-447, 1991.
Issekutz A.C. et al., "A major portion of polymorphonuclear leukocyte and T lymphocyte migration to arthritic joints in the rat is via LFA-1/MAC-1-independent mechanisms",Clinical Immunology and Immunopathology 67(3):257-263, 1993.
Issekutz, A.C. et al., "Monocyte migraion to arthritis in the rat utilizes both CD11/CD18 and very late activation antigen 4 integrin mechanisms", J. Exp. Med. 181:1197-1203, 1995.
Issekutz, A.C. et al., "Treatment of established adjuvant arthritis in rats with monoclonal antibody to CD18 and very late activation

(56) References Cited

OTHER PUBLICATIONS antigen-4 integrins suppress meutrophil and T-lymphocyte migration to the joints and improves clinical disease", Immunology 88(4):569-576, 1996.
Ishikawa, H. et al., "Adhesion molecules in the lymphoid cell distribution in rheumatoid synovial membrane", Bulletin Hospital for Joint Diseases 53(2)23-28, 1993.
Jalkanen et al., "A novel endothelial cell molecule mediating lymphocyte binding in humans", Behring Inst. Mitt. No. 92:36-43, 1993.
Janson et al., Immun. Rev., "Immunotoxins: Hybrid Molecules Combining High Specifity and Potent Cytotoxcity", vol. 62, p. 185 (1982).
Karusis et al., "Treatment of chronic-relapsing experimental autoimmune encephalomyelitis with the synthetic immunomodulator linomide (quinoline-3-carboxamide)", Proc. Natl. Acad. Sci. USA 90:6400-6404, 1993.
Kettleborough et al., "Humanization of a mouse monoclonal antibody by CDR-grafting: the importance of framework residues on loop conformation", Protein Engineering 4(7):773-783, 1991.
Kolbinger et al., "Humanization of a mouse anti-human IgE antibody: a potential therapeutic for IgE-mediated allergies", Protein Engineering 6(8):971-980, 1993.
Koopman et al., "Adhesion through the LFA-1 (CD11a/CD18)-ICAM-1 (CD54) and the VLA-4 (CD49d)-VCAM-1 (CD106) pathways prevents apoptosis of germinal center B cells", J. Immunol., vol. 152, pp. 3760-3767 (1994).
Kuby et al., "Autoimmunity", Immunology $3^{rd}$ pp. 485-505, 1998.
Laffon, A. et al., "Upregulated expression and function of VLA-4 fibronectin receptors on human activated T cells in rheumatoid arthritis", J. Clin. Invest. 88:546-552, 1991.
Laffaille et al., "Myelin basic protein-specific T helper 2 (Th2) cells cause experimental autoimmune encephalomyelitis in immunodeficient hosts rather than protect them from the disease", J. Exp. Med. 186(2):307-312, 1997.
Leger et al., "Humanization of a mouse antibody against human alpha-4 integrin: a potential therapeutic for the treatment of multiple sclerosis", Human Antibodies 8(1): 3-16, 1997.
Leussink et al., "Blockade of signaling via the very late antigen (VLA-4) and its counterligand vascular cell adhesion molecule-1 (VCAM-1) causes increased T cell apoptosis in experimental autoimmune neuritis", Acta Neuropathol., vol. 103, pp. 131-136 (2002).
Lindsey and Wolinsky, Demyelinating Diseases, Medscape from WebMD Sep. 29, 2005, pp. 1-2.
Lipsky et al., "From idea to market: the drug approval process", JABFP 14(5):362-367, 2001.
Lisak et al., "Effect of treatment with copolymer 1(cop-1) on the in vivo and in vitro manifestations of experimental allergic encephalomyelitis (EAE)", Journal Neurol. Sciences 62:281-293, 1983.
Lobb et al., "The Pathophysiologic Role of a4 Integrins In Vivo", J. Clin. Invest., vol. 94, pp. 1722-1728 (1994).
Martin et al., "Absence of seven human herpesviruses, including HHV-6, by polymerase chain reaction in CSF and blood from patients with multiple sclerosis and optic neuritis", Acta Neurol Scand 95(5):280-283, 1997.
Marlor, C.W. et al., "Expression of vascular cell adhesion molecule-1 in fibroblastlike synoviocytes after stimulation with tumor necrosis factor", American J. of Pathology 140(5):1055-1059, 1992.
Miller et al., "A controlled trial of Natalizumab for relapsing multiple sclerosis", N. Engl. J Med. 348:15-23, 2003.
Miller et al., "Guidelines for the use of magnetic resonance techniques in monitoring the treatment of multiple sclerosis", Ann. Neurology 39:6-16, 1996.
Miller et al., "Results of a Double-Blind, Randomized, Placebo-controlled Phase II Trial of Angegren (Natalizumab) in Subjects with Relapsing Multiple Sclerosis," Multiple Sclerosis: Clinical Laboratory Research, $17^{th}$ Congress of the European Committee for Treatment & Research in Multiple Sclerosis (ECTRIMS), Sep. 12-15, 2001.

Morales-Ducret et al., "α4/β1 integrin (VLA-4) ligands in arthritis vascular cell adhesion molecule-1 expression in synovium and on fibroblast-like synoviocytes", J. Immunology 194(4)1424-1431, 1993.
Monshizadegan et al., "VLA-4-dependent adhesion activites of U937 cells and guinea pig bronchoalveolar lavage leukocytes", Agents Actions 39, Special Conference Issue C177-C179, 1993.
Mundy, "Auti-X4 integrin antibody in an animal model suppresses enlargement of multiple myloura and bone destruction and proloups survival type", J. JP. Orthop. Assoc. vol. 75, No. 6, 2001.
Munkholm et al., GUT, "Frequency of glucocorticoid resistance and dependency in Crohn's disease", vol. 35, pp. 360-362 (1994).
Munschauer et al., "Natalizumab significantly increase the cumulative probability of sustained improvement in physical disablity". World Congress on Treatment and Research in Mulitple Sclerosis, Sep. 17-20, 2008.
O'Connor et al., "Return of disease activity after cessation of natalizumab therapy in patients with multiple sclerosis", $25^{th}$ Congress of the European Committee for Treatment and Research in Multiple Sclerosis, Sep. 9-12, 2009.
Panzara and Sandrock, Natalizumab therapy in patients with multiple sclerosis, $25^{th}$ Congress of the European Committee for Treatment and Research in Multiple Sclerosis, Sep. 9-12, 2009, Dusseldorf, Germany.
Paul et al., "Monoclonal antibodies against LFA-1 and VLA-4 inhibit graft vasculitis in rat cardiac allografts", Transplantation Proceedings 25(1):813-814, 1993.
Parker & Waichman, "Overview: Tysabri", Oct. 18, 2005, pp. 1.
Piraino et al.,"Prolonged reversal of chronic experimental allergic encephalomyelitis using a small molecule inhibitor of α4 integrin". Journal of Neuroimmunology 131:147-159, 2002.
Pleiss et al., "Discovery of a novel binding epitope for the α4 integrin based on sequence homology between VCAM-1 and the third heavy chain complementary determining region of anti-α4 antibodies", Society for Neuroscience 26, Abstract No. 126.18, 2000.
Postigo et al., "Increased binding of synovial T lymphocytes from rheumatoid arthritis to endothelial-leukocyte adhesion molecule-1 (ELAM-1) and vascular cell adhesion molecule-1 (VCAM-1)", J. Clin. Invest 89:1445-1452, 1992.
Postigo et al., "The α4β1/VCAM-1 adhesion pathway in physiology and idsease", Res. Immunol., vol. 144, pp. 723-735 (1993).
Podolsky et al., "Attenuation of colitis in the cotton-top tamarinby anti-α4 integrin monoclonal antibody", J. Clin. 192:372-380, 1993.
Polman et al., "A randomized, placebo-controlled trial of natalizumab for relapsing multiple sclerosis", New England J Medicine 354(9):889-910, 2006.
Press Release issued by Elan Corporation, Biogen and Elan Present Promising Data for Antegren(R) (Natalizumab) in Multiple Sclerosis at Ectrims Congress, Sep. 15, 2001.
Pretolani et al., "Antibody to very late activation antigen 4 prevents antigen-induced bronchial hyperreactivity and cellular infiltration in the guinea pig airways", J. Exp. Med. 180(3):795-805, 1994.
Racke et al., "Long-term treatment of chronic relapsing experimental allergic encephalomyelitis by transforming growth factor-β2", J. Neuroimmunology 46:175-184, 1993.
Robinson, M. "Optimizing therapy for inflammatory bowel disease", American J. Gastroenterology 92(12):12S-17S, 1997.
Sadiq et al., "Demyelinating diseases", Merritt's textbook for Neurology pp. 804-829.
Sandborn, W.J., "Transcending conventional therapies: the role of biologic and other novel therapies", Inflammatory Bowel Diseases 7 (suppl.1): S9-16, 2001.
Sandborn et al., "Biologic therapy of inflammatory bowel disease", Gastroenterology 122:1592-1608, 2002.
Salmi et al., "Dual binding capacity of mucosal immunoblasts to mucosal and synovial endothelium in humans: dissection of the molecular mechanisms", J. Exp. Med. 181:137-149, 1995.
Sassevile et al., "Monocyte adhesion to endothelium in simian immunodeficiency virus-induced AIDS encephalitis is mediated by vascular cell adhesion molecule-1/α4β1 integrin interactions", Am. J. Pathology 144(1):27-40, 1994.

(56) References Cited

OTHER PUBLICATIONS

Schreiber et al., Increased Activation of Isolated Intestinal Lamina Propria Mononuclear Cells in Inflammatory Bowel Disease, Gastroenterology, vol. 101, pp. 1020-1030 (1991).

Sheremata et al., "A safety and pharmacokinetic study of intravenous natalizumab in patients with Multiple Sclerosis", American Academy of Neurology1072-1074, 1999.

Sheremata et al., "A placebo-controlled safety, tolerability dose escalation, PK study of various doses of intravenous antegren in patients with multiple sclerosis", Neurology 50:A63-A64, 1998.

Simmons, "Herpesvirus and multiple sclerosis", Herpes 8(3) :60-63, 2001.

Sorbera et al., "Natalizumab", Drugs of the Future 25(9):917-927, 2000.

Stein et al., Surg. Clin. North Am., "Medical Therapy for Crohn's Disease: The State of the Art", vol. 81, pp. 71-101 (1991).

Steinhart, "Clinical perspectives—biologies in IBD: Whats's all the fuss?", Canadian Journal of Gastroenterology 15(12):799-8004, 2001.

Supplementary Partial European Search Report completed on Nov. 29, 2005, in EP 03 70 9277.

Tak et al., "Expression of adhesion molecules in early rheumatoid synovial tissue", Clinical Immunology and Immunopathology 77(3):236-242, 1995.

Tans et al., "Absence of HHV-6 and HHV-7 in cerebrospinal fluid in relapsing remitting multiple sclerosis", Acta Neurol Scand 101(4):224-228, 2000.

Teitelbaum et al., "Synthetic copolymer 1 inhibits human T-cell lines specific for myelin basic protein", Proc. Natl. Acad. Sci. USA 89:137-141, 1992.

Theien et al., "Discordant effects of anti-VLA-4 treatment before and after onset of relapsing experimental autoimmune encephalomyelitis", J. Clinical Investigation 107(8):995-1006, 2001.

Third Party Observations pursuant to Article 115 EPC filed on Nov. 30, 2015, in EP 10 012 871.9.

Tilley et al., "VLA-4 Antagonists", Drugs of the Future 26(10):985-998, 2001.

Tsukamoto et al., "Administration of monoclonal antibodies against vascular cell adhesion molecule-1/very late antigen-4 abrogates predisposing autoimmune diabetes in NOD mice", Cellular Immunology 165(2):193-201, 1995.

Tubridy et al., "The effect of anti-α 4 integrin antibody on brain lesion activity in MS", Neurology 53(3):466-472, 1999.

Tysabri (natalizumab) injection http://www.tysabri.com/pdfs/161061-13_PI.pdf, pp. 1-31, revised:Apr. 2013.

Van Assche et al., "Antiadhesion molecule therapy in inflammatory bowel disease", Inflammatory Bowel Diseases 8(4):291-300, 2002.

Van Assche et al., "Progressive multifocal leukoencephalopathy after natalizumab therapy for Crohn's disease", N. Engl. J. Med. 353(4):362-368, 2005.

Van Dinther-Janssen et al., "The VLA-4/VCAM-1 pathway is involved in lymphocyte adhesion to endothelium in rheumatoid synovium", Journal of Immunology 147(12):4207-4210, 1991.

Van Dinther-Janssen et al., "Role of the CS1 adhesion motif of fibronectin in T cell adhesion to synovial membrane and peripheral lymph node endothelium", Annals of the Rheumatic Diseases 52:672-676, 1993.

Van Bekkum, D.W. "Stem cell transplantation in experimental models of autoimmune disease", Journal of Clinical Immunology 20(1)10-16, 2000.

Wang et al., "Effect of antibody against integrin α4 on bleomycin-induced pulmonary fibrosis in mice", Biochemical Pharmacology 60(12):1949-1958, 2000.

Washington et al., "Expression of immunologically relevant endothelial cell activation antigens on isolated central nervous system microvessels from patients with multiple sclerosis", Ann Neurol. 35:89-97,1994.

Weg, et al., "A monoclonal antibody recognizing very late activation antigen-4 inhibits eosinophil accumulation in vivo", J. Exp. Med. 177(2):561-566, 1993.

Weiner et al., "Double-blind pilot trial of oral tolerization with myelin antigens in multiple sclerosis", Science 259:1321-1324, 1993.

Weilbach et al., Disease modifying treatments for multiple sclerosis—what is on the horizon? CNS Drugs 2:133-157, 1999.

Xiang et al., "Evidence that anti-VIL-4 attenuates leukocyte/endothelial interactions in experimental autoimmune encephalomyelitis", FASEB Journal16 abstract.A847, 642.14, 2002.

Yednock et al., "Prevention of experimental autoimmune encephalomyelitis by antibodies against α4β1 integrin", Nature 3546:63-66, 1991.

Zivadinov et al., "Natalizumab (Tysabri) promotes remyelination in patients with multiple sclerosis", Neurology 72(Suppl 3):P03.071, A140.

* cited by examiner

Summary of Serum Natulizimab Concentrations for 3.0 mg/kg Natulizimab

Month 0

| Patient | Pre-infusion | 60 min. | 2 hrs | 24 hrs | Week 1 | Week 2 | Week 3 | Month 1 |
|---|---|---|---|---|---|---|---|---|
| | | | 74.7 µg/ml | 43.4 µg/ml | 11.6 µg/ml | 4.6 µg/ml | 4.9 µg/ml | 2.3 µg/ml |
| 01 | <0.13 | 65.0 | 74.7 | 43.4 | 11.6 | 4.6 | 4.9 | 2.3 |
| 02 | <0.13 | 56.1 | 72.2 | 39.2 | 17.7 | 11.2 | ND | 3.6 |
| 03 | <0.13 | 58.5 | 60.0 | 34.4 | 10.6 | 5.8 | 3.6 | 1.3 |
| 04 | <0.13 | 77.9 | 97.3 | 54.1 | 16.2 | 7.2 | 2.3 | 0.2 |
| 05 | <0.13 | 75.6 | 67.5 | 42.0 | 17.3 | 10.7 | 8.0 | 5.4 |
| 06 | <0.13 | 72.0 | 73.7 | ND | 10.7 | 4.0 | 1.5 | 1.6 |
| 07 | <0.13 | 16.9 | 30.7 | 23.7 | 13.0 | ND | ND | 3.5 |
| 08 | <0.13 | 54.3 | 58.4 | 49.0 | 15.7 | 9.9 | 6.7 | 4.0 |
| 09 | <0.13 | 82.7 | 74.2 | 62.6 | 18.6 | ND | 3.5 | 2.2 |
| 10 | <0.13 | 84.3 | 84.1 | 64.2 | 22.7 | 10.7 | 7.3 | 3.9 |
| 11 | <0.25 | 62.5 | 72.6 | 42.0 | 14.3 | 6.8 | 4.1 | 2.2 |
| 12 | <0.25 | 102.7 | 80.6 | 82.1 | 25.5 | 13.7 | 5.8 | 3.5 |
| 13 | <0.13 | 76.0 | 67.8 | 44.3 | 13.7 | 8.6 | 5.3 | 2.7 |
| 14 | <0.13 | 66.4 | 70.2 | 36.5 | 11.0 | 6.3 | 3.9 | 2.0 |

Month 0

| | Pre-infusion | 60 min. | 2 hrs | 24 hrs | Week 1 | Week 2 | Week 3 | Month 1 |
|---|---|---|---|---|---|---|---|---|
| N | 14 | 14 | 14 | 13 | 14 | 12 | 12 | 14 |
| Mean | 0.0 | 67.9 | 70.3 | 47.5 | 15.6 | 8.3 | 4.7 | 2.7 |
| SD | 0.00 | 19.60 | 14.96 | 15.18 | 4.50 | 2.98 | 1.97 | 1.33 |

FIG. 3A

Summary of Serum Natulizimab Concentrations for 3.0 mg/kg Natulizimab

| Patient | Month 2 | Month 3 | Month 4 | Pre-infusion | 60 min. | 2 hrs | 24 hrs |
|---|---|---|---|---|---|---|---|
| | | | | Month 5 | | | |
| 01 | 2.4 µg/ml | 1.4 µg/ml | 1.9 µg/ml | ND | ND | ND | ND |
| 02 | 7.1 | 8.0 | 11.1 | 7.8 | 65.1 | 82.3 | 50.5 |
| 03 | 2.3 | 2.9 | 2.7 | 1.2 | 53.9 | 54.7 | 40.6 |
| 04 | <0.13 | <0.13 | <0.13 | <0.13 | 24.6 | 21.4 | 2.5 |
| 05 | 8.1 | 11.4 | 1.8 | 0.2 | ND | ND | ND |
| 06 | 1.4 | 1.8 | 1.9 | 2.0 | 81.9 | 90.3 | 51.9 |
| 07 | 1.7 | 2.5 | 2.2 | 2.6 | 36.0 | 62.7 | 22.2 |
| 08 | 4.5 | 5.7 | 2.0 | 4.7 | 76.0 | 65.0 | ND |
| 09 | 3.4 | 3.9 | 3.3 | 3.3 | 59.7 | 64.8 | 48.5 |
| 10 | 2.9 | 3.3 | 6.1 | 4.5 | 82.0 | 79.6 | 59.9 |
| 11 | 2.7 | 4.6 | 5.5 | 3.0 | 82.6 | 79.3 | 55.6 |
| 12 | 2.0 | 1.9 | 1.9 | 3.6 | 68.8 | ND | 65.2 |
| 13 | 4.3 | 4.3 | 3.6 | 5.0 | 74.9 | 55.4 | 47.0 |
| 14 | 2.1 | 1.6 | 1.9 | 3.0 | 70.3 | 63.0 | 35.5 |

| SRN | Month 2 | Month 3 | Month 4 | Pre-infusion | 60 min. | 2 hrs | 24 hrs |
|---|---|---|---|---|---|---|---|
| | | | | Month 5 | | | |
| N | 14 | 14 | 14 | 13 | 12 | 11 | 11 |
| Mean | 3.2 | 3.8 | 3.3 | 3.1 | 64.7 | 65.3 | 43.6 |
| SD | 2.19 | 2.98 | 2.74 | 2.11 | 18.51 | 18.61 | 18.03 |

FIG. 3B

Summary of Serum Natulizimab Concentrations for 3.0 mg/kg Natulizimab

| Patient | Week 21 | Week 22 | Week 23 | Month 6 | Month 7 | Month 8 | Month 9 | Month 10 | Month 12 |
|---|---|---|---|---|---|---|---|---|---|
| 01 | ND | ND | ND | ND | ND | ND | ND | ND | ND |
| 02 | 33.8 | 21.4 | 10.3 | 8.1 | 0.4 | <0.13 | <0.13 | ND | ND |
| 03 | 21.3 | 9.4 | 4.7 | 5.1 | <0.25 | <0.13 | <0.13 | ND | ND |
| 04 | <0.13 | <0.13 | <0.13 | <0.13 | <0.25 | <0.13 | <0.13 | ND | ND |
| 05 | ND | ND | ND | 0.2 | <0.25 | <0.13 | <0.13 | ND | ND |
| 06 | 21.5 | 7.6 | 3.9 | 2.4 | <0.13 | <0.13 | <0.13 | ND | ND |
| 07 | ND | 11.0 | 6.2 | 3.7 | 0.3 | <0.13 | <0.13 | ND | ND |
| 08 | 19.1 | 13.2 | 9.6 | 5.3 | 0.4 | <0.13 | <0.13 | <0.13 | ND |
| 09 | 33.7 | 13.1 | 6.1 | 3.8 | <0.13 | ND | ND | ND | ND |
| 10 | 29.9 | 16.8 | ND | 7.4 | 0.5 | ND | ND | ND | ND |
| 11 | ND | 18.4 | 10.5 | 6.6 | 0.7 | <0.13 | ND | ND | ND |
| 12 | ND | 9.9 | 6.3 | 3.5 | <0.13 | <0.13 | ND | ND | ND |
| 13 | 22.1 | 13.3 | 9.1 | 4.6 | <0.13 | <0.13 | ND | ND | ND |
| 14 | 14.1 | 8.2 | 9.4 | 4.7 | <0.13 | ND | ND | ND | ND |
| SRN | | | | | | | | | |
| N | 9 | 12 | 11 | 13 | 13 | 10 | 6 | 1 | 0 |
| Mean | 21.7 | 11.9 | 6.9 | 4.3 | 0.2 | 0.0 | 0.0 | 0.0 | |
| SD | 10.57 | 5.61 | 3.25 | 2.44 | 0.25 | 0.00 | 0.00 | | |

FIG. 3C

Summary of Serum Natulizimab Concentrations for 6.0 mg/kg Natulizimab

Month 0

| Patient | Pre-infusion | 60 min. | 2 hrs | 24 hrs | Week 1 | Week 2 | Week 3 | Month 1 |
|---|---|---|---|---|---|---|---|---|
| 01 | <0.25 | 104.8 | 155.3 µg/ml | 110.0 µg/ml | 36.3 µg/ml | 16.8 µg/ml | 11.4 µg/ml | 11.0 µg/ml |
| 02 | <0.13 | 102.8 | 135.0 | 81.8 | 37.5 | 18.7 | 11.0 | 3.9 |
| 03 | <0.13 | 121.1 | 96.3 | 68.4 | 22.9 | 19.9 | 11.4 | 6.6 |
| 04 | <0.13 | 136.0 | 141.2 | 86.6 | 26.0 | 20.9 | 13.7 | 9.8 |
| 05 | <0.13 | 163.8 | 138.6 | 84.4 | 29.4 | 17.5 | 14.0 | 9.6 |
| 06 | <0.13 | 145.7 | 173.7 | 94.8 | 29.3 | 16.5 | 14.0 | 9.7 |
| 07 | <0.25 | 173.5 | 164.0 | 110.0 | 33.9 | ND | ND | ND |
| 08 | <0.13 | 135.8 | 143.0 | 105.8 | 20.9 | 17.6 | 15.0 | 10.9 |
| 09 | <0.13 | 97.3 | 127.9 | 66.8 | 27.0 | 8.3 | 7.8 | 4.8 |
| 10 | <0.13 | 149.2 | 111.2 | 103.2 | 37.0 | 21.4 | 11.9 | 4.8 |
| 11 | <0.25 | 111.6 | 142.5 | 88.9 | 20.8 | 20.7 | 9.7 | 8.6 |
| 12 | <0.13 | 147.6 | 135.0 | 95.5 | 43.9 | 28.0 | 19.4 | 9.9 |
| 13 | <0.25 | 183.9 | 168.6 | 113.2 | 52.0 | 31.7 | 20.9 | 12.1 |
| 14 | <0.13 | 140.2 | 129.2 | 109.9 | 36.9 | 21.0 | 12.2 | 7.9 |

Month 0

| | Pre-infusion | 60 min. | 2 hrs | 24 hrs | Week 1 | Week 2 | Week 3 | Month 1 |
|---|---|---|---|---|---|---|---|---|
| N | 14 | 14 | 14 | 14 | 14 | 13 | 13 | 13 |
| Mean | 0.0 | 136.7 | 140.1 | 94.2 | 32.4 | 19.9 | 13.3 | 8.4 |
| SD | 0.00 | 26.72 | 21.18 | 15.38 | 8.97 | 5.61 | 3.63 | 2.64 |

FIG. 4A

Summary of Serum Natulizimab Concentrations for 6.0 mg/kg Natulizimab

| Patient | Month 2 | Month 3 | Month 4 | Pre-infusion | Month 5 60 min. | 2 hrs | 24 hrs |
|---|---|---|---|---|---|---|---|
| | 10.7 µg/ml | ND µg/ml | 2.4 µg/ml | | | | |
| 01 | ND | ND | ND | ND | ND | ND | ND |
| 02 | 6.8 | 8.2 | 9.6 | 10.3 | ND | ND | ND |
| 03 | 8.6 | 9.9 | 10.5 | 7.8 | 92.6 | 97.5 | 85.9 |
| 04 | 11.8 | 16.4 | 17.1 | 15.8 | 200.1 | 161.1 | 135.6 |
| 05 | 9.3 | 11.6 | 16.9 | 19.5 | 190.4 | 168.3 | 104.4 |
| 06 | 11.7 | 14.5 | 16.8 | 18.2 | 171.3 | 153.0 | 112.7 |
| 07 | ND | ND | ND | ND | ND | ND | ND |
| 08 | 14.6 | 12.9 | 14.2 | 18.4 | 145.2 | 172.5 | 99.2 |
| 09 | 8.5 | 8.4 | 12.0 | ND | 103.0 | 107.5 | 44.9 |
| 10 | 9.0 | 16.3 | 18.1 | 10.9 | 114.3 | 141.4 | 103.0 |
| 11 | 11.8 | 14.2 | 13.3 | 14.5 | 135.7 | 109.4 | 93.8 |
| 12 | 11.7 | ND | ND | ND | ND | ND | ND |
| 13 | 1.6 | <0.13 | 1.9 | 7.5 | 187.0 | 141.8 | 124.6 |
| 14 | 11.2 | 12.6 | 12.8 | 11.8 | 152.4 | 124.0 | 114.6 |

| SRN | Month 2 | Month 3 | Month 4 | Pre-infusion | Month 5 60 min. | 2 hrs | 24 hrs |
|---|---|---|---|---|---|---|---|
| N | 13 | 11 | 12 | 10 | 10 | 10 | 10 |
| Mean | 9.8 | 11.4 | 12.1 | 13.5 | 149.2 | 137.7 | 101.9 |
| SD | 3.18 | 4.71 | 5.39 | 4.43 | 37.96 | 26.82 | 24.75 |

FIG. 4B

Summary of Serum Natulizimab Concentrations for 6.0 mg/kg Natulizimab

| Patient | Week 21 | Week 22 | Week 23 | Month 6 | Month 7 | Month 8 | Month 9 | Month 10 | Month 12 |
|---|---|---|---|---|---|---|---|---|---|
| 01 | ND | ND | ND | ND | ND | ND | ND | ND | ND |
| 02 | ND | ND | ND | ND | ND | ND | ND | ND | ND |
| 03 | 43.2 | 17.2 | 15.5 | 10.1 | 1.3 | <0.13 | <0.13 | ND | ND |
| 04 | 59.1 | 38.6 | 25.1 | 19.3 | 3.4 | 0.2 | <0.13 | ND | ND |
| 05 | 46.0 | 29.3 | 21.3 | 24.8 | 6.5 | 0.3 | 0.2 | ND | ND |
| 06 | 78.9 | 42.9 | 25.1 | 17.4 | 2.9 | <0.13 | <0.13 | ND | ND |
| 07 | ND | ND | ND | ND | ND | ND | ND | ND | ND |
| 08 | 50.1 | 26.0 | 24.7 | 21.2 | ND | 0.7 | <0.13 | <0.13 | ND |
| 09 | 32.2 | 30.2 | 16.6 | 9.3 | 1.1 | <0.13 | <0.13 | ND | ND |
| 10 | 50.7 | 34.3 | 17.0 | 13.1 | 2.1 | <0.13 | <0.13 | <0.13 | ND |
| 11 | 34.0 | 30.0 | 23.7 | 22.5 | 4.6 | <0.13 | ND | ND | ND |
| 12 | ND | ND | ND | ND | ND | ND | ND | ND | ND |
| 13 | 48.1 | 31.9 | 19.3 | 13.6 | ND | ND | ND | ND | ND |
| 14 | 44.8 | 32.3 | 15.5 | 13.6 | 2.6 | ND | ND | ND | ND |
| | Week 21 | Week 22 | Week 23 | Month 6 | Month 7 | Month 8 | Month 9 | Month 10 | Month 12 |
| N | 10 | 10 | 10 | 9 | 8 | 7 | 7 | 2 | 0 |
| Mean | 48.7 | 31.3 | 20.4 | 16.8 | 3.1 | 0.2 | 0.0 | 0.0 | |
| SD | 13.20 | 6.93 | 4.08 | 5.56 | 1.79 | 0.26 | 0.08 | 0.00 | |

FIG. 4C

Levels of receptor saturation maintained in the MS study

| Visit | Sampling Time | Statistic | Placebo (n=71) | 3.0 mg/kg Antegren (n=68) | 6.0 mg/kg Antegren (n=74) |
|---|---|---|---|---|---|
| Month 0 | Pre-infusion | N | 14 | 13 | 14 |
| | | Mean | 9.82 | 8.06 | 7.56 |
| | | SD | 5.331 | 2.192 | 3.135 |
| | | Median | 8.3 | 7.7 | 6.7 |
| | | Minimum | 4.7 | 5.9 | 3.1 |
| | | Maximum | 24.9 | 14.4 | 13.3 |
| Month 0 | 2-Hr Post infusion | N | 14 | 14 | 14 |
| | | Mean | 8.21 | 99.11 | 100.97 |
| | | SD | 3.567 | 10.557 | 4.884 |
| | | Median | 7.5 | 102.4 | 102.1 |
| | | Minimum | 5.2 | 74.9 | 93.2 |
| | | Maximum | 18.6 | 110.8 | 110.7 |

| Visit | Sampling Time | Statistic | Placebo (n=71) | 3.0 mg/kg Antegren (n=68) | 6.0 mg/kg Antegren (n=74) |
|---|---|---|---|---|---|
| Month 0 | 24-Hr Post infusion | N | 12 | 12 | 13 |
| | | Mean | 9.30 | 99.09 | 98.93 |
| | | SD | 7.328 | 9.052 | 12.079 |
| | | Median | 6.7 | 99.9 | 97.4 |
| | | Minimum | 5.6 | 81.5 | 81.2 |
| | | Maximum | 31.9 | 109.4 | 117.5 |
| Week 1 | | N | 14 | 14 | 14 |
| | | Mean | 7.92 | 93.41 | 99.61 |
| | | SD | 2.579 | 5.656 | 12.011 |
| | | Median | 8.3 | 94.3 | 94.9 |
| | | Minimum | 3.5 | 82.8 | 83.5 |
| | | Maximum | 13.3 | 100.9 | 120.8 |

FIG. 5A

Levels of receptor saturation maintained in the MS study

| Visit | Sampling Time | Statistic | Placebo (n=71) | 3.0 mg/kg Antegren (n=68) | 6.0 mg/kg Antegren (n=74) |
|---|---|---|---|---|---|
| Week 2 | | N | 12 | 14 | 13 |
| | | Mean | 8.98 | 88.28 | 97.37 |
| | | SD | 2.991 | 7.494 | 14.377 |
| | | Median | 8.4 | 88.0 | 97.9 |
| | | Minimum | 4.1 | 75.9 | 78.3 |
| | | Maximum | 13.4 | 101.4 | 131.7 |
| Week 3 | | N | 13 | 13 | 12 |
| | | Mean | 8.17 | 80.99 | 92.79 |
| | | SD | 2.242 | 19.150 | 9.767 |
| | | Median | 8.8 | 85.5 | 92.3 |
| | | Minimum | 4.9 | 24.5 | 74.7 |
| | | Maximum | 12.0 | 99.3 | 110.9 |

| Visit | Sampling Time | Statistic | Placebo (n=71) | 3.0 mg/kg Antegren (n=68) | 6.0 mg/kg Antegren (n=74) |
|---|---|---|---|---|---|
| Month 1 | | N | 14 | 13 | 13 |
| | | Mean | 8.87 | 82.48 | 85.58 |
| | | SD | 3.808 | 11.272 | 8.491 |
| | | Median | 8.4 | 84.1 | 84.6 |
| | | Minimum | 3.1 | 56.1 | 68.6 |
| | | Maximum | 17.3 | 100.2 | 96.1 |
| Month 2 | | N | 12 | 14 | 13 |
| | | Mean | 9.41 | 79.15 | 93.21 |
| | | SD | 3.846 | 22.779 | 9.194 |
| | | Median | 9.4 | 87.1 | 94.0 |
| | | Minimum | 4.7 | 7.3 | 75.8 |
| | | Maximum | 19.5 | 96.6 | 104.2 |

FIG. 5B

Levels of receptor saturation maintained in the MS study

| Visit | Sampling Time | Statistic | Placebo (n=71) | 3.0 mg/kg Antegren (n=68) | 6.0 mg/kg Antegren (n=74) |
|---|---|---|---|---|---|
| Month 3 | | N | 12 | 14 | 12 |
| | | Mean | 6.97 | 79.47 | 83.32 |
| | | SD | 2.720 | 23.459 | 18.333 |
| | | Median | 6.5 | 81.6 | 88.9 |
| | | Minimum | 3.3 | 8.9 | 29.2 |
| | | Maximum | 11.4 | 104.5 | 96.3 |
| Month 4 | | N | 10 | 14 | 11 |
| | | Mean | 8.38 | 77.81 | 95.51 |
| | | SD | 3.400 | 25.375 | 15.794 |
| | | Median | 7.1 | 76.0 | 93.6 |
| | | Minimum | 4.9 | 7.9 | 78.3 |
| | | Maximum | 16.9 | 117.4 | 139.0 |

| Visit | Sampling Time | Statistic | Placebo (n=71) | 3.0 mg/kg Antegren (n=68) | 6.0 mg/kg Antegren (n=74) |
|---|---|---|---|---|---|
| Month 5 | Pre-infusion | N | 9 | 13 | 11 |
| | | Mean | 9.48 | 70.88 | 91.94 |
| | | SD | 2.606 | 26.535 | 10.720 |
| | | Median | 9.1 | 75.1 | 94.8 |
| | | Minimum | 6.1 | 9.0 | 75.4 |
| | | Maximum | 15.6 | 115.0 | 106.9 |
| Month 5 | 2-Hr Post infusion | N | 9 | 11 | 10 |
| | | Mean | 11.03 | 92.09 | 99.19 |
| | | SD | 6.203 | 8.267 | 10.200 |
| | | Median | 7.6 | 95.0 | 97.4 |
| | | Minimum | 4.9 | 79.7 | 82.5 |
| | | Maximum | 21.7 | 103.4 | 114.6 |

FIG. 5C

Levels of receptor saturation maintained in the MS study

| Visit | Sampling Time | Statistic | Placebo (n=71) | 3.0 mg/kg Antegren (n=68) | 6.0 mg/kg Antegren (n=74) |
|---|---|---|---|---|---|
| Month 5 | 24-Hr Post infusion | N | 8 | 12 | 10 |
| | | Mean | 7.50 | 92.04 | 89.08 |
| | | SD | 2.660 | 15.256 | 32.364 |
| | | Median | 6.4 | 94.6 | 95.9 |
| | | Minimum | 4.7 | 49.5 | 4.8 |
| | | Maximum | 12.8 | 106.4 | 123.2 |
| Week 21 | | N | 8 | 12 | 11 |
| | | Mean | 8.06 | 80.25 | 92.27 |
| | | SD | 2.217 | 24.078 | 11.557 |
| | | Median | 8.2 | 86.2 | 88.9 |
| | | Minimum | 4.3 | 5.1 | 77.3 |
| | | Maximum | 11.7 | 94.6 | 112.9 |

| Visit | Sampling Time | Statistic | Placebo (n=71) | 3.0 mg/kg Antegren (n=68) | 6.0 mg/kg Antegren (n=74) |
|---|---|---|---|---|---|
| Week 22 | | N | 7 | 12 | 10 |
| | | Mean | 8.67 | 84.98 | 90.44 |
| | | SD | 2.471 | 25.744 | 18.174 |
| | | Median | 8.7 | 90.5 | 81.6 |
| | | Minimum | 5.1 | 6.2 | 73.5 |
| | | Maximum | 12.0 | 101.7 | 127.8 |
| Week 23 | | N | 7 | 10 | 10 |
| | | Mean | 9.16 | 82.89 | 97.24 |
| | | SD | 2.950 | 27.649 | 23.374 |
| | | Median | 8.7 | 90.2 | 90.9 |
| | | Minimum | 4.6 | 6.1 | 78.8 |
| | | Maximum | 14.0 | 100.5 | 154.8 |

FIG. 5D

Levels of receptor saturation maintained in the MS study

| Visit | Sampling Time | Statistic | Placebo (n=71) | 3.0 mg/kg Antegren (n=68) | 6.0 mg/kg Antegren (n=74) |
|---|---|---|---|---|---|
| Month 6 | | N | 10 | 13 | 9 |
| | | Mean | 8.65 | 67.32 | 80.59 |
| | | SD | 3.574 | 29.838 | 27.738 |
| | | Median | 8.2 | 80.2 | 85.4 |
| | | Minimum | 4.4 | 6.4 | 10.0 |
| | | Maximum | 16.7 | 102.5 | 106.2 |
| Month 7 | | N | 10 | 12 | 8 |
| | | Mean | 7.69 | 42.10 | 80.46 |
| | | SD | 1.281 | 24.011 | 27.664 |
| | | Median | 7.7 | 41.1 | 67.2 |
| | | Minimum | 5.1 | 4.7 | 62.5 |
| | | Maximum | 10.4 | 88.0 | 145.2 |

| Visit | Sampling Time | Statistic | Placebo (n=71) | 3.0 mg/kg Antegren (n=68) | 6.0 mg/kg Antegren (n=74) |
|---|---|---|---|---|---|
| Month 8 | | N | 10 | 13 | 8 |
| | | Mean | 7.60 | 14.09 | 34.16 |
| | | SD | 1.726 | 10.214 | 21.619 |
| | | Median | 6.9 | 12.1 | 29.6 |
| | | Minimum | 6.0 | 6.2 | 11.8 |
| | | Maximum | 10.7 | 45.0 | 59.6 |
| Month 9 | | N | 5 | 7 | 7 |
| | | Mean | 9.52 | 5.88 | 9.45 |
| | | SD | 2.701 | 2.246 | 4.644 |
| | | Median | 9.0 | 5.6 | 7.7 |
| | | Minimum | 6.3 | 3.7 | 5.5 |
| | | Maximum | 13.5 | 10.4 | 18.0 |

FIG. 5E

Levels of receptor saturation maintained in the MS study

| Visit | Sampling Time | Statistic | Placebo (n=71) | 3.0 mg/kg Antegren (n=68) | 6.0 mg/kg Antegren (n=74) |
|---|---|---|---|---|---|
| Month 10 | | N | 2 | 3 | 4 |
| | | Mean | 7.78 | 8.65 | 9.17 |
| | | SD | 2.029 | 0.635 | 1.655 |
| | | Median | 7.8 | 8.6 | 9.3 |
| | | Minimum | 6.3 | 8.0 | 7.1 |
| | | Maximum | 9.2 | 9.3 | 11.0 |
| Month 12 | | N | 1 | 1 | 1 |
| | | Mean | 8.80 | 6.04 | 6.61 |
| | | SD | | | |
| | | Median | 8.8 | 6.0 | 6.6 |
| | | Minimum | 8.8 | 6.0 | 6.6 |
| | | Maximum | 8.8 | 6.0 | 6.6 |

| Visit | Sampling Time | Statistic | Placebo (n=71) | 3.0 mg/kg Antegren (n=68) | 6.0 mg/kg Antegren (n=74) |
|---|---|---|---|---|---|
| Early Termination | | N | 0 | 1 | 1 |
| | | Mean | | 94.51 | 32.29 |
| | | SD | | | |
| | | Median | | 94.5 | 32.3 |
| | | Minimum | | 94.5 | 32.3 |
| | | Maximum | | 94.5 | 32.3 |

FIG. 5F

ADMINISTRATION OF AGENTS FOR THE TREATMENT OF INFLAMMATION

This application is a continuation of U.S. Ser. No. 15/586,724, filed May 4, 2017, now abandoned, which is a continuation of U.S. application Ser. No. 14/613,821, filed Feb. 4, 2015, now abandoned, which is a continuation of U.S. application Ser. No. 12/846,350 filed Jul. 29, 2010, now abandoned, which is a divisional of U.S. application Ser. No. 11/540,640, filed Oct. 2, 2006, now U.S. Pat. No. 7,807,167, which is a divisional of U.S. application Ser. No. 10/372,111, filed Feb. 25, 2003, now abandoned, which claims priority under 35 U.S.C. § 119 to U.S. Provisional Application Ser. No. 60/374,501 entitled ADMINISTRATION OF AGENTS FOR THE TREATMENT OF INFLAMMATION filed Apr. 23, 2002, and Provisional Application No. 60/360,134, entitled ADMINISTRATION OF AGENTS FOR THE TREATMENT OF INFLAMMATION filed on Feb. 25, 2002, the entire contents of each of which are hereby incorporated by reference in their entirety for all purposes.

SEQUENCE LISTING

The instant application contains a Sequence Listing which has been filed electronically in ASCII format and is hereby incorporated by reference in its entirety. Said ASCII copy, created on Jan. 20, 2020, is named P1070US008_SL.txt and is 2,883 bytes in size.

FIELD OF THE INVENTION

This invention relates generally to agents that specifically bind to and inhibit an integrin receptor comprising an alpha-4 ($\alpha$4) subunit, and therapeutic uses of the same.

BACKGROUND OF THE INVENTION

Inflammation is a response of vascularized tissues to infection or injury and is affected by adhesion of leukocytes to the endothelial cells of blood vessels and their infiltration into the surrounding tissues. In normal inflammation, the infiltrating leukocytes release toxic mediators to kill invading organisms, phagocytize debris and dead cells, and play a role in tissue repair and the immune response. However, in pathological inflammation, infiltrating leukocytes are over-responsive and can cause serious or fatal damage. See, e.g., Hickey, *Psychoneuroimmunology II* (Academic Press 1990).

The integrins are a family of cell-surface glycoproteins involved in cell-adhesion, immune cell migration and activation. Alpha-4 integrin is expressed by all circulating leukocytes except neutrophils, and forms heterodimeric receptors in conjunction with either the beta1 or beta7 integrin subunits; both alpha-4 beta-1 ($\alpha$4$\beta$1) and alpha-4 beta-7 ($\alpha$4$\beta$7) dimers play a role in the migration of leukocytes across the vascular endothelium (Springer et al., 1994 *Cell* 76: 301-14; and Butcher et al., 1996 *Science* 272: 60-6) and contribute to cell activation and survival within the parenchyma (Damle et al., 1993 *J. Immunol.* 151: 2368-79; Koopman et al., 1994 *J. Immunol.* 152: 3760-7; and Leussink et al., 2002 *Acta Neuropathol.* 103:131-136).

Specifically, alpha-4 beta-1 (also known as very late antigen-4 (VLA-4)), binds to vascular cell adhesion molecule-1 (VCAM-1)(Lobb et al., 19941 *J. Clin. Invest.* 94:1722-8), which is expressed by the vascular endothelium at many sites of chronic inflammation (Bevilacqua et al., 1993 *Annu. Rev. Immunol.* 11: 767-804; and Postigo et al., 1993 *Res. Immunol.* 144:723-35). The alpha-4 beta-7 dimer interacts with mucosal addressin cell adhesion molecule (MAdCAM-1), and mediates homing of lymphocytes to the gut (Farstad et al., 1997 *Am. J. Pathol.* 150: 187-99; and Issekutz et al., 1991 *J. Immunol.* 147: 4178-84). Expression of MAdCAM-1 on the vascular endothelium is also increased at sites of inflammation in the intestinal tract of patients with inflammatory bowel disease (IBD) (Briskin et al., 1997 *Am. J. Pathol.* 151: 97-110).

Adhesion molecules such as alpha-4 integrins are potential targets for therapeutic agents. For instance, the VLA-4 receptor, of which alpha-4 integrin is a subunit, is an important target because of its interaction with a ligand residing on brain endothelial cells. Diseases and conditions resulting from brain inflammation have particularly severe consequences. In another example, the alpha-4 beta-7 integrin dimer is an important target due to its involvement in lymphocyte homing and pathological inflammation in the gastrointestinal tract.

Alpha-4 beta-1 integrin is expressed on the extracellular surface of activated lymphocytes and monocytes, which have been implicated in the pathogenesis of acute inflammatory brain lesions and blood brain barrier (BBB) breakdown associated with multiple sclerosis (MS) (Coles et al., 1999 *Ann. Neurol.* 46(3): 296-304). Agents against alpha-4 integrin have been tested for their anti-inflammatory potential both in vitro and in vivo in animal models. See Yednock et al., 1992 *Nature* 356: 63-66; U.S. Pat. No. 5,840,299 issued to Bendig, et al. on Nov. 24, 1998, and U.S. Pat. No. 6,001,809 issued to Thorsett et al. on Dec. 14, 1999. The in vitro experiments demonstrate that alpha-4 integrin antibodies block attachment of lymphocytes to brain endothelial cells. Experiments testing the effect of alpha-4 integrin antibodies on animals having an artificially induced condition simulating multiple sclerosis, experimental autoimmune encephalomyelitis (EAE), have demonstrated that administration of anti-alpha-4 integrin antibodies prevents inflammation of the brain and subsequent paralysis in the animals. Collectively, these experiments identify anti-alpha-4 integrin antibodies as potentially useful therapeutic agents for treating multiple sclerosis and other inflammatory diseases and disorders.

In another specific example of pathological inflammation involving alpha-4 integrins, Crohn's disease (CD) is a chronic, incurable, relapsing, transmural inflammation of the intestinal tract. The disease is characterized by inappropriate immune cell migration and activation in the intestinal mucosa involving T cells, macrophages and neutrophils (Schreiber et al., 1991 *Gastroenterology* 101: 1020-30). First-line medical therapies for Crohn's disease include 5-aminosalicylates (5-ASAs), which have low efficacy, and corticosteroids, which have various short- and long-term side effects (Munkholm et al., 1994 *Gut* 35: 360-2). Patients refractory to first-line therapies are treated with immunosuppressive agents such as azathioprine, 6-mercaptopurine, and methotrexate, but these agents have a slow onset of action and potentially serious side effects (Stein et al., 2001 *Surg. Clin. North Am.* 81: 71-101, viii). More recently, biologic agents with a faster onset of action have been introduced for use in treating Crohn's disease, but such agents are similarly plagued by issues such as long-term efficacy and side effects.

SUMMARY OF THE INVENTION

The present invention provides methods of chronically reducing pathological inflammation in a patient via the chronic administration of an agent that selectively binds to alpha-4 integrin. The chronic dosage regime of an alpha-4 agent is designed such that (1) the agent specifically binds to alpha-4 integrin or an integrin, dimer comprising alpha-4 integrin, and (2) the agent is administered repeatedly to maintain alpha-4 integrin receptor saturation at a sufficient level to suppress pathological inflammation. The agent of the invention can be useful in the suppression of inflammation via binding and inhibition of all integrin dimers comprising the alpha-4 subunit, or it can be designed to bind to a specific dimer, e.g., alpha-4 beta-1.

In one embodiment, the efficacy of a chronic dosage regime can be determined by the measurement of saturation of a specific integrin dimer. In a particular example, it is believed that alpha-4 beta-1 integrin dimer is involved in multiple sclerosis, and thus the level of saturation required for an efficacious chronic administration regime can be measured via measurement of the saturation of the alpha-4 beta-1 dimer receptor.

In another embodiment, where multiple integrin dimers are believed to be involved in a pathological inflammation, saturation of a combination of dimer receptors can be measured to determine the efficacy of a chronic administration regime. In a specific example, both the alpha-4 beta-1 and the alpha-4 beta-7 dimers are believed to have involvement in pathological inflammation associated with inflammatory bowel disease. Thus, measurement of both alpha-4 beta-1 and alpha-4 beta-7 saturation levels may be beneficial in determining the efficacy of a particular chronic administration regime.

In one embodiment, the success of a chronic dosage regime can be determined by assessing a physiological marker of the pathological inflammation. For example, in a chronic dosage regime administered for MS, the success of the dosage regime can be confirmed by detection of the levels of brain lesions using an imaging technique, e.g.; magnetic resonance imaging (MRI). In another example, in a chronic dosage regime administered for CD, the success of the dosage regime can be confirmed by detection of the levels of serum C-reactive protein levels in a patient. In yet another example, the success of the dosage regime can be determined using a set group of criteria associated with wellness, e.g., reduction in CDAI in a CD patient.

Another embodiment of the invention contemplates the treatment of an inflammatory disease of the gastrointestinal tract (e.g., Crohn's disease, ulcerative colitis and inflammatory bowel disease) of a subject comprising administering a therapeutically effective amount of a composition comprising natalizumab sufficient to treat or ameliorate said inflammatory disease of the gastrointestinal tract in said subject.

In a specific embodiment, the invention features a dosage regime wherein repeated administration of an agent is provided to provide a level of alpha-4 integrin receptor saturation of 65-100% in a patient, thereby providing chronic suppression of pathological inflammation in the patient. In another specific embodiment, the agent is repeatedly administered to provide levels of at least about 75-100% in a patient. In yet another specific embodiment, the agent in repeatedly administered to provide levels of at least about 80-100% in a patient.

A feature of the invention is that undesirable effects of pathological inflammation can be suppressed long-term in a patient, e.g., over a period of six months, one year, two years, or more.

An aspect of the method of the invention is that sufficient levels of an anti-alpha-4 integrin agent are maintained over long periods to suppress pathological inflammation over those periods.

A feature of the invention is that the dosage form provides lower levels of pathological inflammation over longer periods as compared to a single dose.

An advantage of the invention is that agents used in the methods of the invention are well tolerated and have low toxicity.

These and other objects, advantages, and features of the invention will become apparent to those persons skilled in the art upon reading the details of the methods and formulations as more fully described below.

BRIEF DESCRIPTIONS OF THE DRAWINGS

FIGS. 3A-C and 4A-C show the serum concentrations of natalizumab following the dosage regime time points in an MS study. FIGS. 3A-C show the levels for the 3-mg/kg study; FIGS. 4A-C show the levels for the 6-mg/kg study.

FIGS. 5A-F illustrates the levels of receptor saturation maintained in the MS study. Levels shown are percentage values.

Figure 6:
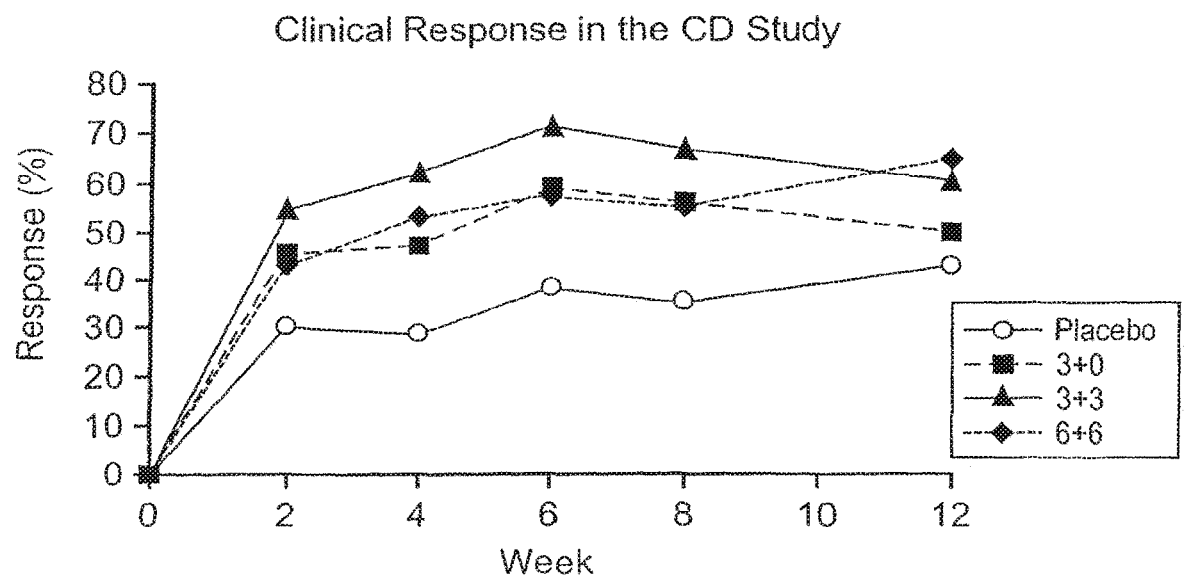
Figure 7:
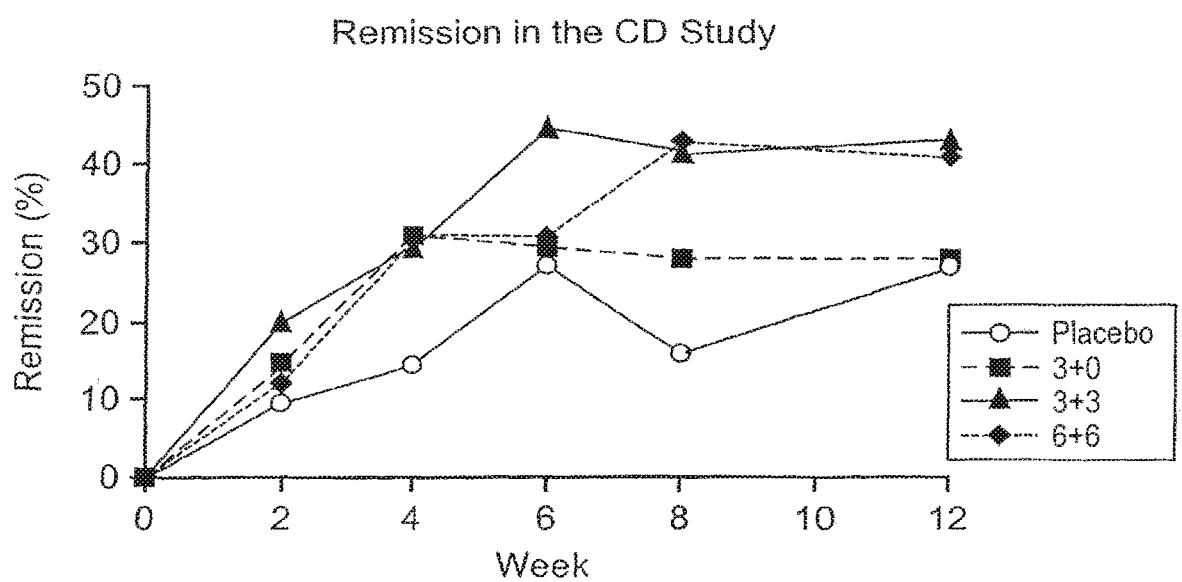

FIGS. 6 and 7 show the percentage of Patients Achieving Predefined Criteria of Clinical Response (FIG. 6) or Remission (FIG. 7) following dosing in the CD study.

Figure 8:
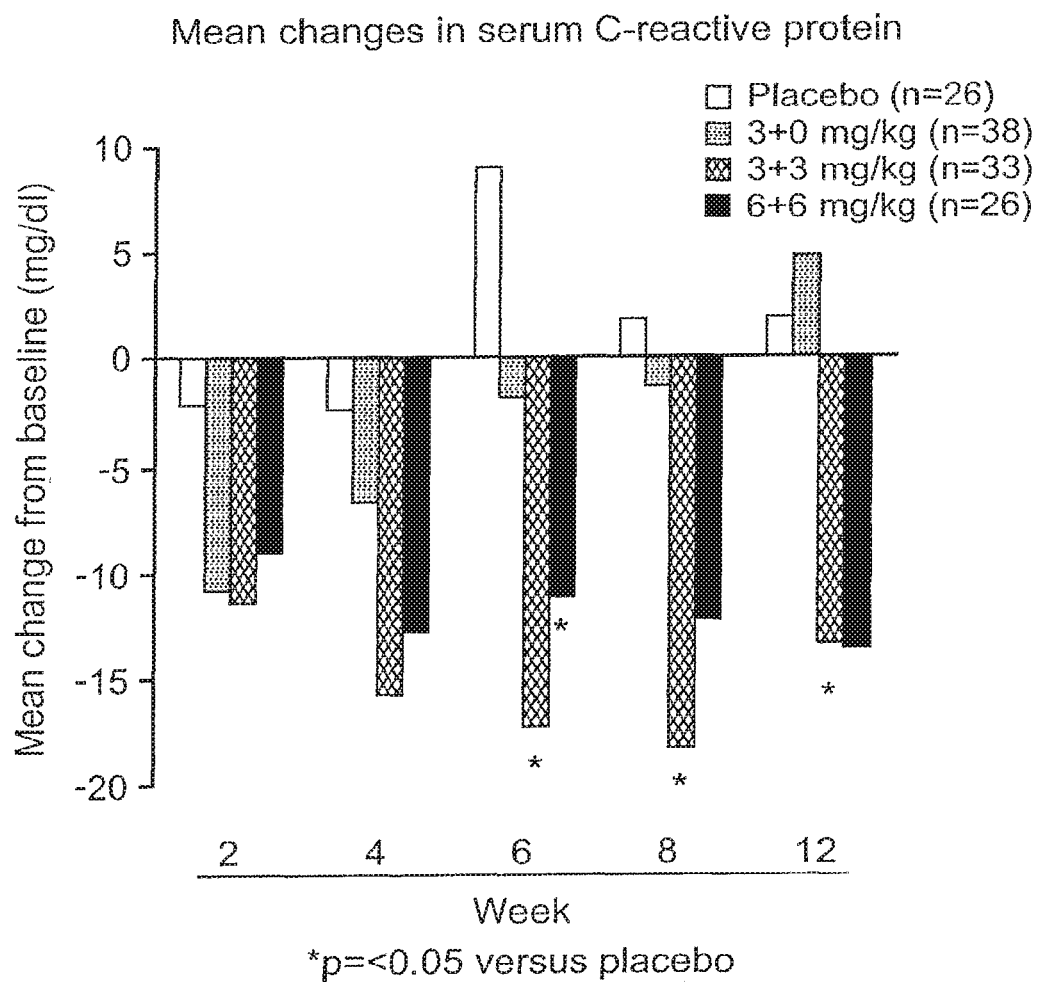

FIG. 8 illustrates mean changes in serum C-reactive protein in a subset of patients who had elevated C-reactive protein at base-line in the CD study. Base-line values were (in mg/l): Placebo, 38.44 (N=26); 3+0 mg/kg Group, 32.35 (N=38); 3+3 mg/kg Group, 41.16 (N=33); and 6+6 mg/kg Group, 333 (N=26).

Figure 9A:
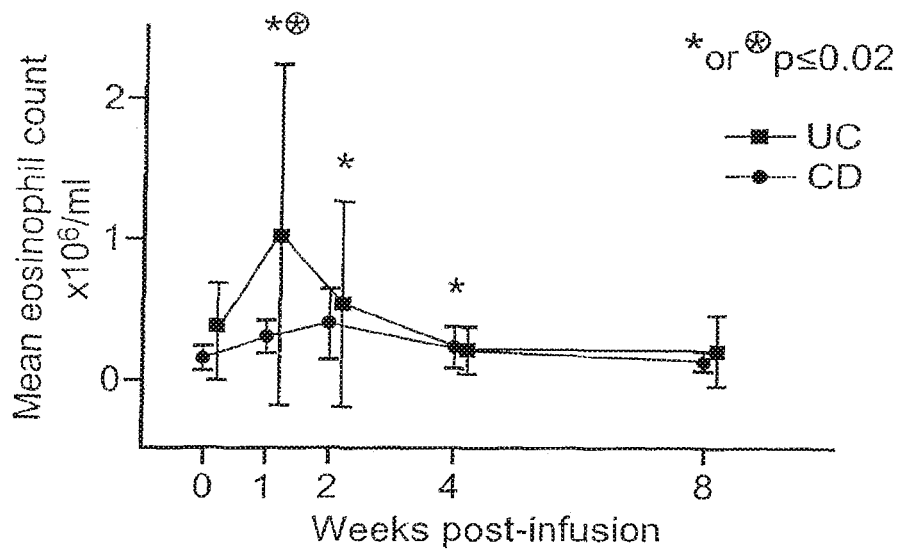
Figure 9B:
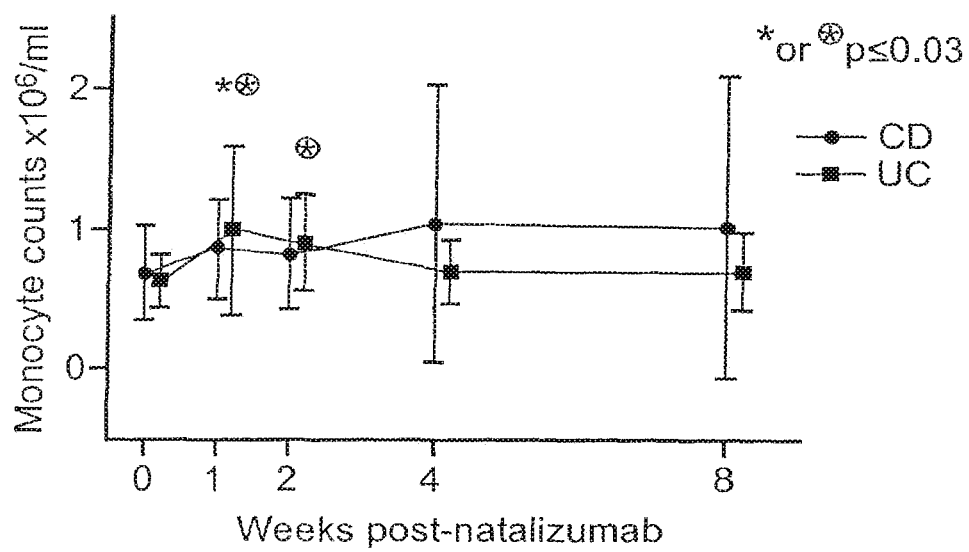
Figure 10A:
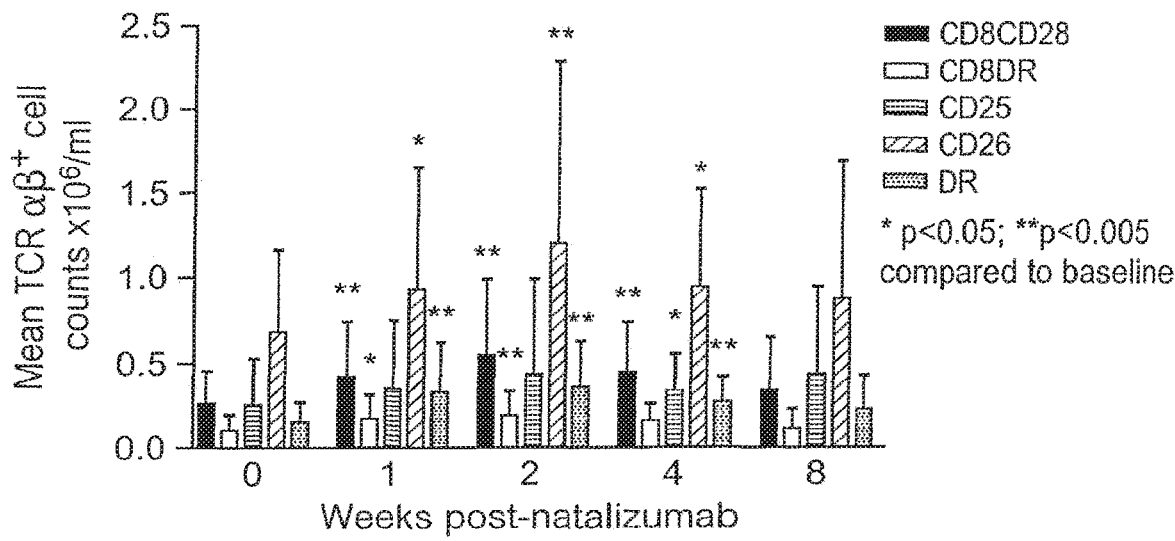
Figure 10B:
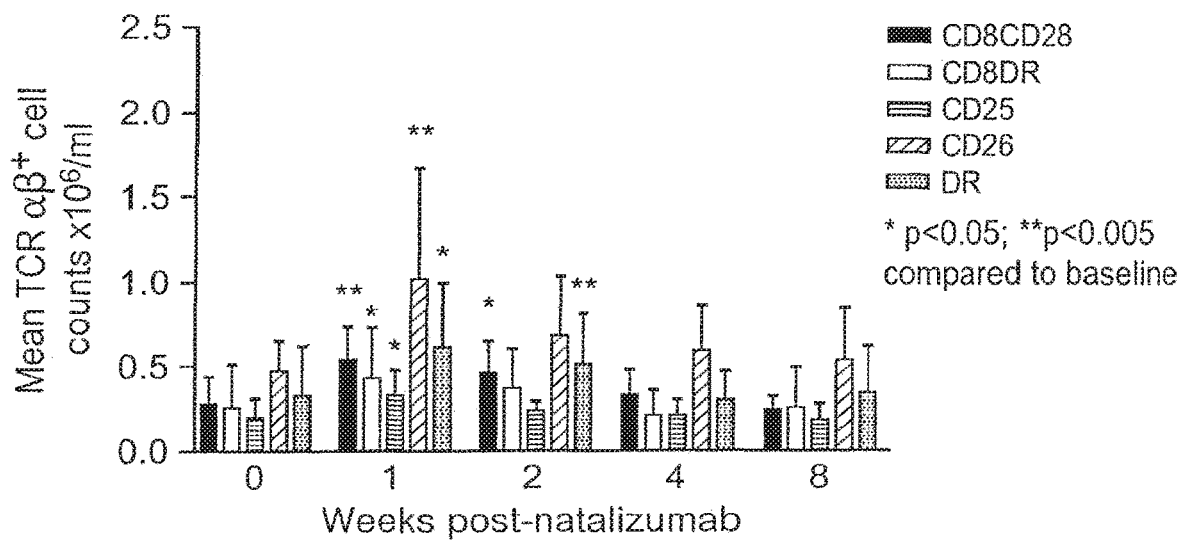
Figure 10C:
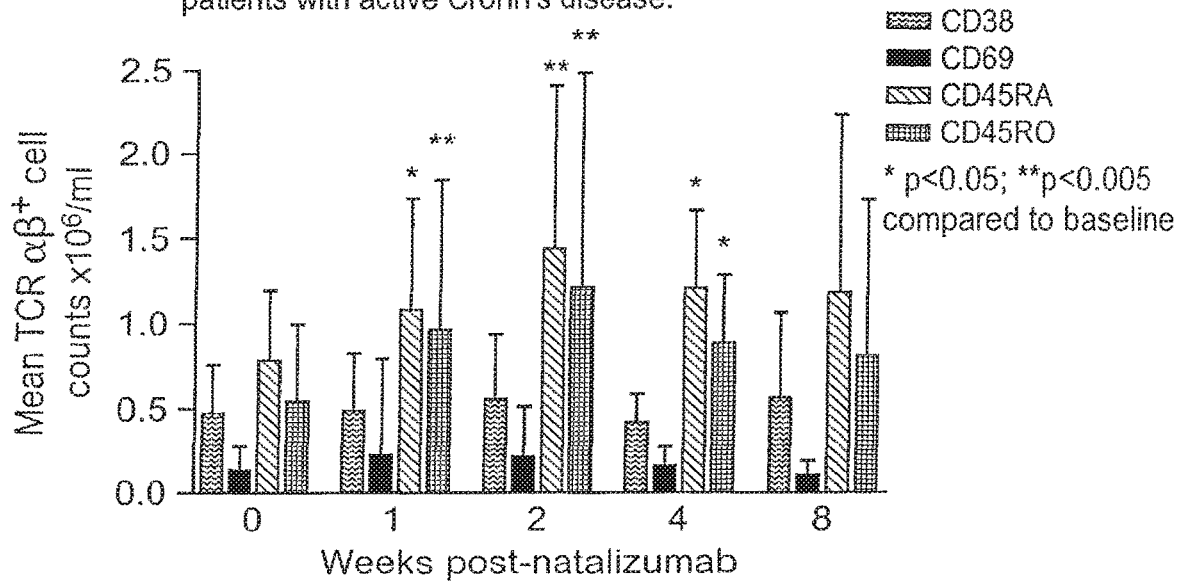
Figure 10D:
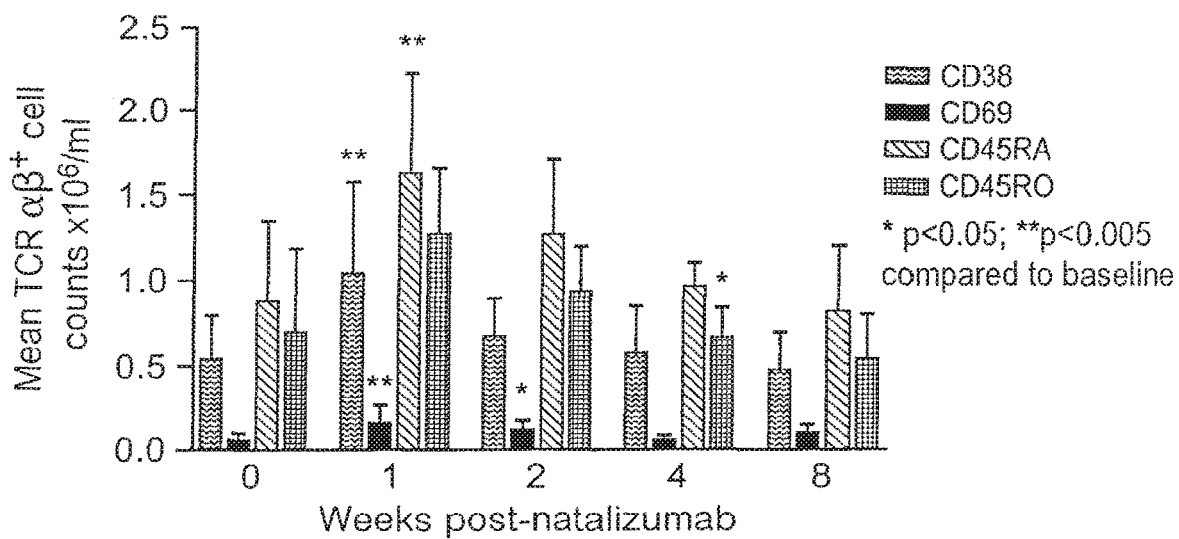

FIGS. 9 A-B demonstrate respectively the effects of natalizumab on circulating eosinophils in patients with active Crohn's disease (CD) and ulcerative colitis (UC). FIG. 9A demonstrates that natalizumab significantly increased circulating eosinophil counts in Crohn's disease (n=18) and ulcerative colitis patients (n=12) after 3 mg/kg natalizumab infusion. FIG. 9B shows that administration of natalizumab significantly increased monocyte counts in active Crohn's disease and ulcerative colitis patients after 3 mg/kg natalizumab infusion.

FIGS. 10 A-D demonstrate the impact of natalizumab administration on TCR$\alpha\beta^+$ cells expressing activation antigen. Panel A demonstrates the effect of natalizumab in patients with active Crohn's disease, i.e., a significant increase of TCR$\alpha\beta^+$ cells expressing CD26, HLA-DR, CD8CR and CD8 CD28 to at least four weeks post 3 mg/kg natalizumab infusion. Panel B demonstrates the effects of natalizumab on TCR$\alpha\beta^+$ cells expressing activation antigens in patients with activated ulcerative colitis, i.e., significant increase in TCR$\alpha\beta^+$ cells expressing CD26, HLA-DR, CD8DR and CD8CD28 to at least four weeks post 3 mg/kg natalizumab in fusion. Panel C demonstrates the effects of natalizumab administration on TCR$\alpha\beta^+$ cells expressing activation antigens and memory and naïve markers in patients with active Crohn's disease, i.e., significant increase of memory (CD45RO) and naïve (CD45RA) TCR$\alpha\beta^+$ cells to at least four weeks post-natalizumab infusion. Panel B shows the effects of natalizumab on TCR$\alpha\beta^+$ cells expressing activation antigens, memory and naïve markers in patients with active ulcerative colitis, i.e., significant increase of memory (CD45RO), naïve (CD45RA), CD69 and CD38 TCRαβ+ cells at one week post natalizumab administration.

Figure 11A:
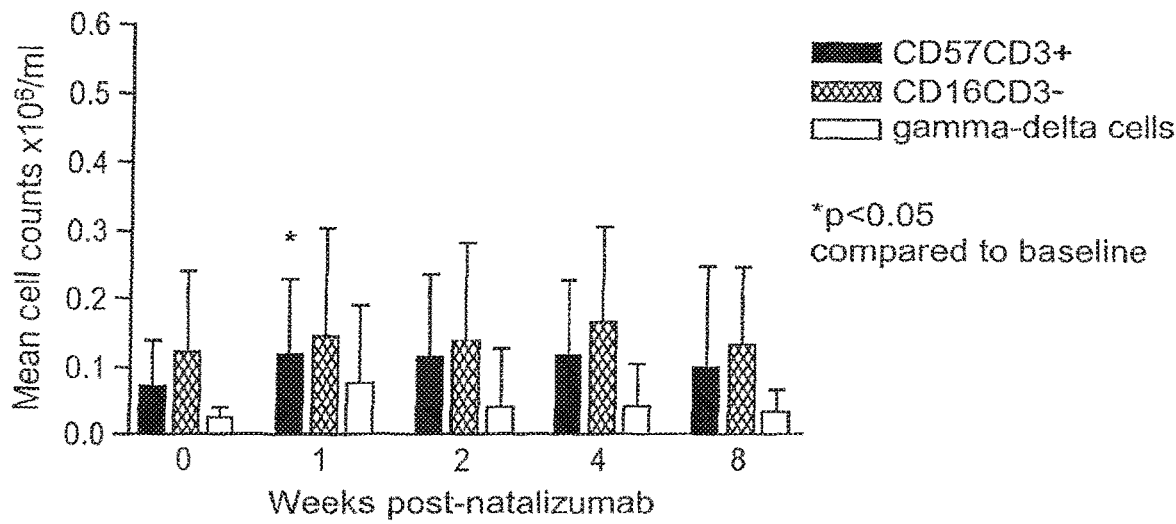
Figure 11B:
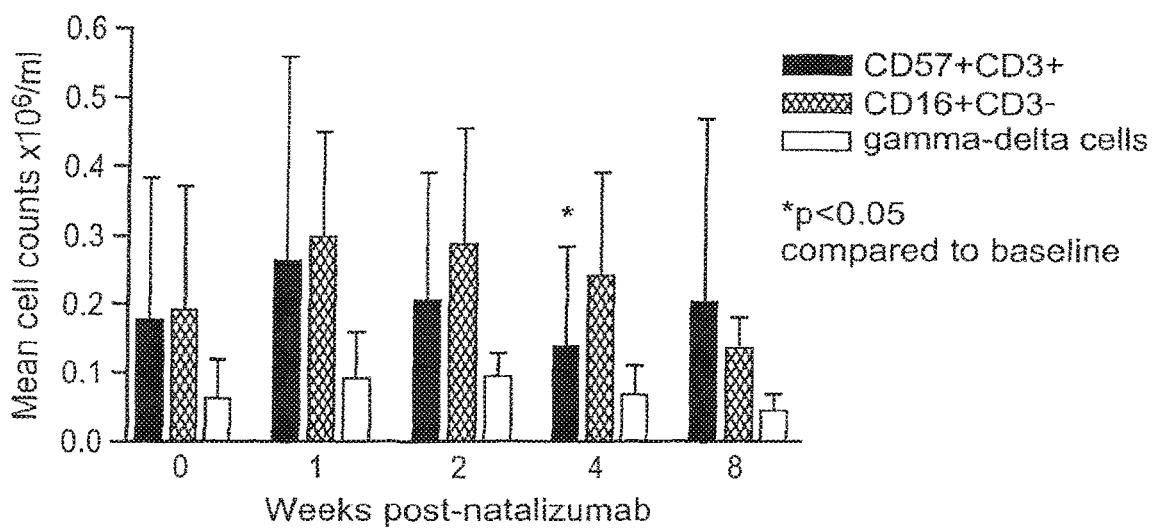

FIGS. 11 A-B demonstrate the effect of natalizumab on circulating TCRαβ+ and NK-type cells in patients with active Crohn's disease and with ulcerative colitis respectively.

DETAILED DESCRIPTION OF TILE INVENTION

Before the present methods and therapeutic agents are described, it is to be understood that this invention is not limited to particular methods and therapeutic agents described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "anti-alpha-4 agent" as used herein refers to any agent, which binds specifically to an integrin comprising an alpha-4 subunit and inhibits activity of the integrin. This includes agents that specifically bind to alpha-4 integrin, as well as agents that bind to an integrin dimer that comprises the alpha-4 integrin, e.g., alpha-4 beta-1 (α4β1) or alpha-4 beta-7 (α4β7). The term "agents" is meant to include synthetic and recombinant molecules (e.g., antibodies, small molecules, peptides, or other synthetically produced molecules or compounds, as well as recombinantly produced gene products) as well as naturally-occurring compounds (e.g., polypeptides, antibodies, and the like).

The term "efficacy" as used herein in the context of a chronic dosage regime refers to the effectiveness of a particular treatment regime. Efficacy can be measured based on change the course of the disease in response to an agent of the present invention. For example, in the treatment of MS, efficacy can be measured by the frequency of relapses in relapsing-remitting MS, and by the presence or absence of new lesions in the central nervous system as detected using methods such as MRI.

The term "success" as used herein in the context of chronic treatment regimes refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce the most favorable patient outcome.

The terms "specifically binds" or "binds specifically" as used herein refer to the situation in which one member of a specific binding pair will not show any significant binding to molecules other than its specific binding partner (e.g., an affinity of about 1,000× or more for its binding partner). In the present invention, the anti-alpha-4 integrin agent will not show significant binding to any polypeptide other than an alpha-4 integrin or a receptor comprising an alpha-4 integrin. For example, antibodies used in the methods of the invention that bind to an alpha-4 integrin with a binding affinity of $10^7$ mole/l or more, preferably $10^8$ mole/liters or more, are said to bind specifically to an alpha-4 integrin.

The term "substantially homologous" as used herein is intended to mean any polypeptide that has an alteration in the sequence such that a functionally equivalent amino acid is substituted for one or more amino acids in the polypeptide, thus producing a change that has no or relatively little effect on the binding properties of the polypeptide. For example, one or more amino acid residues within the sequence can be substituted by another amino acid of a similar polarity.

The terms "elicits an immune response" and "elicits a host immune response" as used herein refer to the production of an immunological response to a receptor comprising an alpha-4 integrin in a subject upon introduction of an agent of the invention to the subject. An immune response in the subject can be characterized by serum reactivity with an alpha-4 integrin receptor that is at least twice that of an untreated subject, more preferably three times the reactivity of an untreated subject, and even more preferably at least four times the reactivity of an untreated subject, with serum immunoreactivity measured using a serum dilution of approximately 1:100.

The term "excipient material" is intended to mean any compound forming a part of the formulation that is intended to act merely as a carrier, i.e. not intended to have biological activity itself.

The term "adjuvant" as used herein refers to a composition additive that augments the immune response to an agent of the invention but which will not on its own elicit an immune response. Adjuvants may augment the immune response using a variety of biological mechanisms, including hut not limited to lymphocytic recruitment, T cell stimulation, B cell stimulation, and macrophage stimulation.

The terms "treating", and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease and/or its symptoms or conditions. The invention is directed towards treating a patient's suffering from disease related to pathological inflammation. The present invention is involved in preventing, inhibiting, or relieving adverse effects attributed to pathological inflammation over long periods of time and/or are such caused by the physiological responses to inappropriate inflammation present in a biological system over long periods of time.

The term "pathological inflammation" as used herein refers to an inappropriate and chronic inflammation associated with disorders including, but not limited to, asthma, atherosclerosis, AIDS dementia, diabetes, inflammatory bowel disease, rheumatoid arthritis, transplant rejection, graft versus host disease, multiple sclerosis (especially to inhibit further demyelination), tumor metastasis, nephritis, atopic dermatitis, psoriasis, myocardial ischemic, chronic prostatitis, complications from sickle cell anemia, lupus erythematosus, and acute leukocyte mediated lung injury. Such inflammation is characterized by a heightened response of inflammatory cells, including infiltrating leukocytes. Over time, such pathological inflammation often results in damage to tissue in the region of inappropriate inflammation.

By "Antegren®" is meant to include the antibody also known as AN100226 (antibody code number) or natalizumab (USAN name). Antegren® is a recombinant, humanized anti-alpha-4 integrin antibody. Preferably the disease or condition being treated in the mammal is one which is modulated when a therapeutically effective dose of Antegren® is administered.

General Aspects of the Invention

The present invention is based on the surprising result that chronic administration of an emerging class of new compounds known as selective adhesion molecule inhibitors (SAMIs) is sufficient to provide the maintenance of chronic suppression of inflammation in disorders involving integrin dimers. Upon cessation of the repeated dosage regime, the suppression of the inflammation is reversed (see, e.g., FIG. 2). Previous treatments of inflammatory inhibitors have approached the dosage regimes quite differently, in the belief that the administration of an inflammatory inhibitor would cause a reaction of the body's own response system, which would in turn lead to a recognition of the inflammation as pathological and a resulting chronic relief of the pathological inflammation. What the inventors have shown herein is that a chronic dosage regime is not only more effective than a short-term dosage regime, but in fact it is required to maintain the suppression of pathological inflammation. Thus, in order to realize some of the more important advantages of the invention, the levels of an anti-alpha-4 integrin agent need to be maintained over a number of months or even years.

The present invention is based on the results of a large, randomized, placebo-controlled trial of an anti-alpha-4 integrin antibody, natalizumab, in patients with relapsing MS or with moderate to severely active CD. Natalizumab is a recombinant, humanized, monoclonal antibody antagonist against alpha-4 integrin. Results from these two trials have shown that treatment with natalizumab improved the signs and symptoms of patients with MS and CD. The invention is also intended to include other chimeric antibodies, including Primatized™ antibodies.

In a general sense the method of the invention does not involve any particular mode of administration, since the mode of administration is dependent upon the form of the active agent and the formulation developed to administer the active agent(s). However, the specific examples described here were obtained using parenteral administration of natalizumab. Although the present invention is described using an antibody that specifically binds to alpha-4 integrin, it is also intended to include chronic administration of, for example, bivalent or multivalent antibodies that recognize both partners of an integrin dimer, provided the dimer comprises an alpha-4 integrin.

The general concept of the invention relates to introducing relatively constant amounts of an active agent to a patient's circulatory system over a period of months or years. This chronic introduction of an agent that selectively binds to alpha-4 integrin or a dimer comprising alpha-4 integrin results in suppression of pathological inflammation being maintained at a constant level over a period of time. By maintaining therapeutic levels of an active agent for a period of time, pathological inflammation can be chronically suppressed in the patient.

In a very specific sense, the invention involves obtaining and maintaining a receptor saturation level in a human patient of a dimer comprising alpha-4 integrin in a range of from about 65% to about 100%, more preferably between about 75% to about 100%, and even more preferably between about 80% to about 100%. These receptor saturation levels are maintained at these levels chronically (e.g., over a period of 6 months or so) to allow for continued suppression of pathological inflammation.

Agents that Selectively Bind to Alpha-4 Integrins

Various types of agents with the ability to bind to and inhibit alpha-4 integrin activity can be used in the practice of the invention. Many such agents have been identified and characterized, and specific agents are described below. Given the teachings disclosed herein, it is well within the skill of one in the art to identify other agents that will be able to inhibit the alpha-4-comprising integrin dimers in a manner that biologically mimics or is similar to the specifically described agents, and the present invention is intended to include the chronic administration of such agents and combinations of such agents.

Antibodies

In one specific embodiment, the agents of the invention are antibodies or immunologically active fragments thereof that selectively bind to an alpha-4 integrin or a dimer comprising alpha-4, such as alpha-4 beta-1 or alpha-4 beta-7.

When the agent of the invention is an antibody, a monoclonal antibody is preferred. In contrast to polyclonal antibody preparations, which typically include different antibodies directed against different epitopes, each monoclonal antibody is directed against a single epitope on the antigen. A second advantage of monoclonal antibodies is that they are synthesized by means that are uncontaminated by other immunoglobulins, e.g., by phage display or isolation from a hybridoma. Although the present invention intends to encompass both polyclonal and monoclonal antibodies as agents of the invention, monoclonal antibodies are preferred as they are highly specific, and the invention is thus discussed primarily in terms of monoclonal antibodies.

In addition, other antibodies can be identified using techniques available in the art. For example, monoclonal antibodies of the present invention can be produced using phage display technology. Antibody fragments that selectively bind to an alpha-4 integrin or a dimer comprising an alpha-4 integrin are then isolated. Exemplary preferred methods for producing such antibodies via phage display are disclosed in U.S. Pat. Nos. 6,225,447; 6,180,336; 6,172,197; 6,140,471; 5,969,108; 5,885,793; 5,872,215; 5,871,907; 5,858,657; 5,837,242; 5,733,743; and 5,565,332.

Monoclonal antibodies can also be produced using the conventional hybridoma methods. These methods have been widely applied to produce hybrid cell lines that secrete high levels of monoclonal antibodies against many specific antigens, and can also be used to produce monoclonal antibodies of the present invention. For example, mice (e.g., Balb/c mice) can be immunized with an antigenic alpha-4 integrin epitope by intraperitoneal injection. After sufficient time has passed to allow for an immune response, the mice are sacrificed, and the spleen cells obtained and fused with myeloma cells, using techniques well known in the art. The resulting fused cells, hybridomas, are then grown in a selective medium, and the surviving cells grown in such medium using limiting dilution conditions. After cloning and recloning, hybridomas can be isolated that secrete antibodies (for example, of the IgG or IgM class or IgG1 subclass) that selectively bind to the target, alpha-4 integrin or a dimer comprising an alpha-4 integrin. To produce agents specific for human use, the isolated monoclonal can then be used to produce chimeric and humanized antibodies.

Antibodies of the invention include, but are not limited to, polyclonal, monoclonal, multispecific, human, humanized or chimeric antibodies, single chain antibodies (e.g., scFv), Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. Most preferably the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments that can comprise any combination of variable region(s) with a hinge region, CH1, CH2, and CH3 domains. The antibodies of the invention may be from any animal origin including birds and mammals. Preferably, the antibodies are human, murine (e.g., mouse and rat), donkey, sheep, monkey, rabbit, goat, guinea pig, pig, camel, horse, or chicken (or other avian). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

Chimeric and humanized antibodies can be produced from non-human antibodies, and can have the same or similar binding affinity as the antibody from which they are produced. Techniques for producing chimeric antibodies (Morrison et al., 1984 Proc. Natl. Acad. Sci. 81: 6851; Neuberger et al., 1984 Nature 312: 604; Takeda et al., 1985 Nature 314: 452) include splicing the genes from, e.g., a mouse antibody molecule of appropriate antigen specificity together with genes from a human antibody molecule of appropriate biological activity; such antibodies are within the scope of this invention. For example, a nucleic acid encoding a variable (V) region of a mouse monoclonal antibody can be joined to a nucleic acid encoding a human constant (C) region, e.g., IgG1 or IgG4. The resulting antibody is thus a species hybrid, generally with the antigen binding domain from the non-human antibody and the C or effector domain from a human or primate antibody.

Humanized antibodies are antibodies with variable regions that are primarily from a human antibody (i.e., the acceptor antibody), but which have complementarity determining regions substantially from a non-human antibody (the donor antibody). See, e.g., Queen et al., Proc. Nat'l. Acad. Sci USA 86: 10029-10033 (1989); WO 90/07861, U.S. Pat. Nos. 6,054,297; 5,693,761; 5,585,089; 5,530,101; and 5,224,539. The constant region or regions of these antibodies are generally also from a human antibody. The human variable domains are typically chosen from human antibodies having sequences displaying a high homology with the desired non-human variable region binding domains. The heavy and light chain variable residues can be derived from the same antibody, or a different human antibody. In addition, the sequences can be chosen as a consensus of several human antibodies, such as described in WO 92/22653.

A "Primatized™ antibody" is a recombinant antibody containing primate variable sequences or antigen binding portions, and human constant domain sequences. See Newman, Biotechnology, 1992, 10: 1455-60. Primatization of antibodies results in the generation of antibodies that contain monkey variable domains and human constant sequences. For more details see U.S. Pat. No. 6,113,898. This technique modifies antibodies such that they are not rejected upon administration in humans because they are antigenic. This technique relies on immunization of cynomolgus monkeys with human antigens or receptors. This technique was developed to create high affinity monoclonal antibodies directed to human cell surface antigens.

Specific amino acids within the human variable region are selected for substitution based on the predicted conformation and antigen binding properties. This can be determined using techniques such as computer modeling, prediction of the behavior and binding properties of amino acids at certain locations within the variable region, and observation of effects of substitution. For example, when an amino acid differs between a non-human variable region and a human variable region, the human variable region can be altered to reflect the amino acid composition of the non-human variable region.

In a specific embodiment, the antibodies used in the chronic dosage regime of the present invention are humanized antibodies as disclosed in U.S. Pat. No. 5,840,299, which is incorporated herein by reference.

In another embodiment, transgenic mice containing human antibody genes can be immunized with an antigenic alpha-4 integrin structure and hybridoma technology can be used to generate human antibodies that selectively bind to alpha-4 integrin.

Chimeric, human and/or humanized antibodies can be produced by using recombinant expression, e.g., expression in human hybridomas (Cole et al., *Monoclonal Antibodies and Cancer Therapy*, Alan R. Liss, p. 77 (1985)), in myeloma cells or in Chinese hamster ovary (CHO) cells. Alternatively, antibody coding sequences can be incorporated into transgenes for introduction into the genome of a transgenic animal and subsequent expression in the milk of the transgenic animal. See e.g., U.S. Pat. Nos. 6,197,946; 5,849,992; 5,565,362; 5,336,894; and 5,304,489. Suitable transgenes include transgenes having a promoter and/or enhancer from a mammary gland specific gene, for example casein or β-lactoglobulin.

Small Molecules

Small molecules for use in the present invention encompass numerous chemical classes, though typically they are organic molecules, preferably small organic compounds having a molecular weight of more than 50 and less than about 4,000 Daltons. Candidate agents comprise functional groups necessary for structural interaction with proteins, particularly hydrogen bonding, and typically include at least an amine, carbonyl, hydroxyl or carboxyl group, preferably at least two of functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

The small molecules can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Anti-Alpha-4 Integrin Peptides

The methods of the invention can be performed with any peptide that is capable of binding to an alpha-4 integrin or a dimer comprising an alpha-4 subunit. Included in the methods of the invention are peptides that are substantially homologous to a region of the extracellular matrix or a natural ligand of the specific alpha-4 integrin receptor or receptors targeted. For example, for the chronic inhibition of alpha-4 beta-1 receptor, peptides can be used that comprise at least a portion of the fibronectin IIICS region (e.g., peptides comprising at least a portion of the CS-1 peptide sequence or a sequence substantially homologous to the CS-1 sequence) can be used to bind to a receptor and inhibit the activity of the alpha-4 comprising integrin. See for example U.S. Ser. No. 08/452,098, which is incorporated by reference in its entirety.

Agents that Elicit an Immune Response

In a specific embodiment, the agents of the invention are peptides or peptidomimetics that comprise an immunogenic fragment of an alpha-4 integrin. An immunogenic fragment is any fragment that comprises an epitope of alpha-4, and generally has at least 3, 5, 7, 10, 15, 17 or 20 contiguous amino acids from a naturally occurring mammalian alpha-4 protein. The peptide sequence of both human and murine alpha-4 is accessible from GenBank (Accession Nos. AA59613 and NP_034706). One skilled in the art can readily design a peptide agent of the invention based on the amino acid sequence of alpha-4 or using the wild-type nucleotides that encode them (e.g., GenBank Accession Nos. L12002 and NM_01056, respectively). Once an appropriate peptide is designed, it can be initially screened against antibodies known to have the desired immunogenic activity, e.g., antibodies that selectively bind to an alpha-4 structure and are characterized by the ability to inhibit the activity of an integrin comprising alpha-4.

The immunogenic fragment may also be designed to have amino acid analogs or other structural elements that will enhance the immunogenic response. In particular, peptide fragments may have altered C- or N-terminal ends that enhance overall immunogenicity of the molecules while not impeding their ability to elicit an immune response. Examples of such analogs include, but are not limited to: alpha, alpha-disubstituted amino acids, N-alkyl amino acids, lactic acid, 4-hydroxyproline, gamma-carboxyglutamate, gamma-N,N,N,-trimethyllysine, gamma-N-acetyllysine, O-phosphoserine, N-acetylserine, N-formylmethionine, 3-methylhistidine, and 5-hydroxylysine. Other useful analogs can be found in Sigma, *Biochemicals and Reagents*, Sigma-Aldrich (2001). The fragment may also be detectably labeled to allow for tracking of the molecule within a subject following administration to a subject.

Peptides, analog structures, peptidomimetics and the like can be isolated from natural sources, and then optionally processed (e.g., via peptide cleavage) or alternatively synthesized by conventional techniques known in the art such as solid phase synthesis or recombinant expression. See, e.g., Sambrook et al., *Molecular Cloning: A Laboratory Manual* (Cold Spring Harbor Press, New York, $2^{nd}$ edition 1989). Automatic peptide synthesis can be performed using a commercially available apparatus from manufacturers such as Applied Biosystems (Foster City, Calif.), and methods of doing so are well established. Recombinant production of the proteins may be in prokaryotic, such as phage or bacterial cells or eukaryotic systems, such as yeast, insect, or mammalian cells. Alternatively, proteins can be produced using cell-free in vitro systems known in the art.

In another example, phage peptide display libraries can be used to express large numbers of peptides that can be screened in vitro to identify peptides that specifically bind to alpha-4 or a dimer comprising an alpha-4 integrin. Phage display technology provides a means for expressing a diverse population of random or selectively randomized peptides. Various methods of phage display and methods for producing diverse populations of peptides are well known in the art. For example, Ladner et al. (U.S. Pat. No. 5,223,409), describes methods for preparing diverse populations of binding domains on the surface of a phage. Ladner et al. describe phage vectors useful for producing a phage display library, as well as methods for selecting potential binding domains and producing randomly or selectively mutated binding domains. Screening of a phage display library generally involves in vitro palming of the library using a purified target molecule. Phage that bind the target molecule can be recovered; individual phage can be cloned, and the peptide expressed by a cloned phage can be determined.

Similarly, Smith and Scott (*Meth. Enzymol.* 217: 228-257 (1993) and *Science* 249: 386-390 (1990)) describe methods of producing phage peptide display libraries, including vectors and methods of diversifying the population of peptides that are expressed (see, also, Huse, WO 91/07141 and WO 91/07149). Phage display technology can be particularly powerful when used, for example, with a codon based mutagenesis method, which can be used to produce random peptides or desirably biased peptides (see, e.g., U.S. Pat. No. 5,264,563). These and other well known methods can be used to produce a phage display library, which can be subjected to the in vivo panning method of the invention in order to identify a peptide that homes to one or a few selected organs.

The molecules of a peptide phage display library also can be present as a conjugate, which can facilitate recovery or identification of the peptide of interest. As used herein, the term "conjugate" means a peptide or peptidomimetic of the library linked to a physical, chemical or biological moiety such as but not limited to a solid substrate, a plastic microbead, an oligonucleotide or a bacteriophage, and the like. The moiety can provide a means to identify or recover an agent.

Some agents used to elicit an immune response mimic the appropriate epitope for inducing an immune response against alpha-4 integrin but are too small to be immunogenic on their own. In this situation, a peptide agent can be linked to a suitable carrier to facilitate an immune response. Suitable carriers include serum albumins, keyhole limpet hemocyanin (KLH), immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers include T-cell epitopes that bind to multiple MHC alleles, e.g., at least 75% of all human MHC alleles. Such carriers are sometimes known in the art as "universal T-cell epitopes." Examples of universal T-cell epitopes include:

| | |
|---|---|
| Influenza Hemagluttinin: $HA_{307-319}$ | PKYVKQNTLKLAT (SEQ ID NO: 1) |
| PADRE | AKXVAAWTLKAAA (SEQ ID NO: 2), where X is preferably cyclohexylalanine, tyrosine, or phenylalanine |
| Malaria CS: T3 epitope | EKKIAKMEKASSVFNV (SEQ ID NO: 3) |
| Hepatitis B surface antigen: $HBsAg_{19-28}$ | FFLLTRILTI (SEQ ID NO: 4) |
| Heat Shock Protein 65: $hsp65_{153-171}$ | DQSIGDLIAEAMDKVGNEG (SEQ ID NO: 5) |
| bacille Calmette-Guerin | QVHFQPLPPAVVKL (SEQ ID NO: 6) |
| Tetanus toxoid: $TT_{830-844}$ | QYIKANSKFIGITEL (SEQ ID NO: 7) |
| Tetanus toxoid: $TT_{947-967}$ | FNNFTVSFWLRVPKVSASHLE (SEQ ID NO: 8) |
| HIV gp120 T1 | KQIINMWQEVGKAMYA. (SEQ ID NO: 9) |

Other carriers for stimulating or enhancing an immune response include cytokines such as IL-1, IL-1 α and β peptides, IL-2, γ-INF, IL-10, GM-CSF, and chemokines, such as macrophage inflammatory protein (MIP)1α and β and RANTES (i.e., regulation upon activation normal T cell expressed and secreted). Immunogenic agents can also be linked to peptides that enhance transport across tissues, as described in WO 97/17613 and WO 97/17614.

Immunogenic agents can be linked to carriers by chemical cross-linking. Techniques for linking an agent to a carrier include but are not limited to the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and a peptide cysteine that resides on one protein and an amide linkage through the ε-amino on a lysine, or other free amino group in other amino acids. A variety of such disulfide/amide-forming agents are described in *Immun. Rev.* 62: 185 (1982). Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, and 4-(N-maleimidomethyl)cyclohexane-1-carboxylic acid. The carboxyl groups can be activated by combining them with succinimide or 1-hydroxyl-2-nitro-4-sulfonic acid sodium salt.

Peptide agents can also be expressed as fusion proteins with carriers (i.e., heterologous peptides). The peptide agent can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N- and C-termini of the peptide. Some carrier peptides serve to induce a helper T-cell response against the carrier peptide. The induced helper T-cells in turn induce a B-cell response against the immunogenic peptide linked to the carrier peptide.

Whether the agent is an antibody, polypeptide, peptide, small molecule or other pharmaceutically useful compound according to the present invention that is to be given to an individual, administration is via a chronic dosage regime. The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's *Pharmaceutical Sciences,* 18th edition, Osol, A. (ed.), 1990.

Pharmaceutical Compositions

The present invention also provides pharmaceutical compositions for the reduction of chronic pathological inflammation in a subject susceptible to such and/or suffering from a disorder associated with pathological inflammation.

Pharmaceutical formulations of the invention preferably contain an agent in a concentration from about 0.1 to about 10% of the formulation. They may also be used in appropriate association with other pharmaceutically active compounds. The following methods and excipients are merely exemplary and are in no way meant to be limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

When the agent is an antibody, the formulation is preferably administered in a parenteral dosage form. The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like. Also included may be carrier molecules such as proteoglycans. Specific examples of such carrier molecules include, but are not limited to, glycosaminoglycans such as heparin sulfate, hyaluronic acid, keratan-sulfate, chondroitin 4-sulfate, chondroitin 6-sulfate, heparan sulfate and dermatin sulfate, perlecan, and pentopolysulfate.

Antibodies of the invention can be administered as injectionable dosages of a solution or as a suspension of the substance in a physiologically acceptable diluent with a pharmaceutical carrier that can be a sterile liquid such as water and oils with or without the addition of a surfactant. Other pharmaceutically preparations are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. The agents of this invention can be administered in a sustained release form, for example a depot injection, implant preparation, or osmotic pump, which can be formulated in such a manner as to permit a sustained release of the active ingredient.

In addition, agents of the invention that are antibodies may be provided by administering a polynucleotide encoding a whole or partial antibody (e.g., a single chain Fv) to a subject. The polynucleotide is administered to a subject in an appropriate vehicle to allow the expression of the antibody in the subject in a therapeutically effective amount.

The agents of the invention can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol. The formulations may also contain conventional additives such as solubilizers, isotonic agents, suspending agents, emulsifying agents, stabilizers and preservatives.

The agents can be utilized in aerosol formulation to be administered via inhalation or pulmonary delivery. The agents of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The agents of the present invention can be administered rectally via a suppository. The suppository can include vehicles such as cocoa butter, carbowaxes and polyethylene glycols, which melt at body temperature, yet are solidified at room temperature.

Administration of an agent of the invention may be accomplished by any convenient means, including parenteral injection, and may be systemic or localized in delivery. The agents of this invention can be incorporated into a variety of formulations for therapeutic administration. More particularly, the agents of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the agents can be achieved in various ways, including oral, buccal, rectal, parenteral, intraperitoneal, intradermal, transdermal, intratracheal, intranasal, gastric, intramuscular, intracranial, subdermal etc., administration. The active agent may be systemic after administration or may be localized by the use of regional administration, intramural administration, or use of an implant that acts to retain the active dose at the site of implantation.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more agents of the present invention. Similarly, unit dosage forms for injection or intravenous administration may comprise the agent of the present invention in a composition as a solution in sterile water, normal saline or another pharmaceutically acceptable carrier.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant is placed in proximity to the site of protein deposits (e.g., the site of formation of amyloid deposits associated with neurodegenerative disorders), so that the local concentration of active agent is increased at that site relative to the rest of the body.

A typical dosage unit for administration of a subject includes, but is not limited to: a solution suitable for intravenous administration; a tablet taken from two to six times daily; or a one time-release capsule or tablet taken once a day and containing a proportionally higher content of active ingredient, etc. The time-release effect may be obtained by capsule materials that dissolve at different pH values, by capsules that release slowly by osmotic pressure or by any other known means of controlled release.

Certain agents of the invention, including antibodies and peptides, are sometimes administered in combination with an adjuvant. A variety of adjuvants can be used in combination with an anti alpha-4 integrin agent to elicit an immune response. Preferred adjuvants augment the intrinsic response to an agent without causing conformational changes in the agent that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540, (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., 1997 *N. Engl. J. Med.* 336: 86-91). Another adjuvant is CpG (WO 98/40100). Alternatively, an agent can be coupled to an adjuvant. However, such coupling should not substantially change the conformation of the desired alpha-4 epitope so as to affect the nature of the host immune response. Adjuvants can be administered as a component of a therapeutic composition with an active agent or can be administered separately, before, concurrently with, or after administration of the therapeutic agent.

A preferred class of adjuvants for administration is aluminum salts (alum), such as aluminum hydroxide, aluminum phosphate, and aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™, or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphoryl lipid A, trehalose dimycolate (TDM), and cell wall skeleton (CWS), preferably MPL+CWS (Detox™). Another class of preferred adjuvants is saponin adjuvants, such as Stimulon™ (QS-21; Aquila, Framingham, Mass.) or particles generated therefrom, such as ISCOMs (immunostimulating complexes) and ISCOMATRIX. Other adjuvants include Complete and Incomplete Freund's Adjuvant (IFA), cytokines, such as interleukins (IL-1, IL-2, and IL-12), macrophage colony stimulating factor (M-CSF), and tumor necrosis factor (TNF). Such adjuvants are generally available from commercial sources.

An adjuvant can be administered with an agent as a single composition, or can be administered before, concurrent with or after administration of the agent. The agent and an adjuvant can be packaged and supplied in the same vial or can be packaged in separate vials and mixed before use. The agent and adjuvant are typically packaged with a label indicating the intended therapeutic application. If the agent and adjuvant are packaged separately, the packaging typically includes instructions for mixing before use. The choice of an adjuvant and/or carrier depends on such factors as the stability of the formulation containing the adjuvant, the route of administration, the dosing schedule, and the efficacy of the adjuvant for the species being vaccinated. In humans, a preferred pharmaceutically acceptable adjuvant is one that has been approved for human administration by pertinent regulatory bodies. Examples of such preferred adjuvants for humans include alum, MPL and QS-21. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., 1998 *Advanced Drug Delivery Reviews* 32: 173-186), optionally in combination with any of alum, QS-21, and MPL and all combinations thereof.

Chronic Administration Dosage Regimes

The chronic treatment regimes of the present invention provides anti-alpha-4 integrin agent at a level that will maintain sufficient receptor saturation to suppress pathological inflammation in a patient in need of such. The methods of the invention entail administration once per every two weeks or once a month to once every two months, with repeated dosings taking place over a period of at least six months, and more preferably for a year or longer. The methods of the invention involve obtaining and maintaining a receptor saturation level in a human patient of a dimer comprising alpha-4 integrin (e.g., VLA-4) in a range of from about 65% to 100%, more preferably between about 75% to about 100%, and even more preferably between about 80% to about 100%. These receptor saturation levels are maintained at these levels chronically (e.g., over a period of 6 months or so) to allow for continued suppression of pathological inflammation.

In a specific embodiment, the anti-alpha-4 agent is an antibody, preferably a humanized or human antibody (e.g., natalizumab), and the dosing is on a monthly basis. Levels of receptor saturation can be monitored to determine the efficacy of the dosing regime, and physiological markers measured to confirm the success of the dosage regime. As a confirmation, serum levels of the antibody can be monitored to identify clearance of the antibody and to determine the potential effect of half-life on the efficacy of the treatment.

The amount of agent administered in a dosage unit may depend on whether adjuvant is also administered, with higher dosages generally being required in the presence of adjuvant. For immunization with an agent of the invention, the dosage ranges from about 0.0001 to about 100 mg/kg, and more usually about 0.01 to 5 mg/kg, of the host body weight. For example, dosages can be about 1 mg/kg body weight or about 10 mg/kg body weight. Dosage and frequency may vary depending on the half-life of the agent in the patient. The dosage and frequency of administration can vary depending on whether the treatment is prophylactic or therapeutic. For antibody administration, each dosing injection is generally between about 2.0 to about 8.0 mg/kg. In accordance with the teachings provided herein, effective dosages can be monitored by obtaining a fluid sample from the patient, generally a blood serum or cerebrospinal fluid sample, and determining the integrin receptor saturation using methods well known in the art. Ideally, a sample is taken prior to initial dosing; subsequent samples are taken and measured prior to and/or after each immunization. A particularly preferred amount is a 3 mg per kg of patient per month of natalizumab or an immunologically active fragment equivalent thereof.

When adjuvant is being administered, the dosage level is increased in accordance with the particular adjuvant and the level of immunogenicity of the anti-alpha-4 agent. Doses for individual agents, selected in accordance with the present invention, are determined according to standard dosing methods, taken in conjunction with the teachings provided herein.

As an alternative to chronic administration comprised of repeated individual dosings, an anti-alpha-4 agent can be administered as a sustained release formulation, provided the dosage is such that the levels of receptor saturation remain sufficient to suppress inflammation. For example, controlled release systems can be used to chronically administer an anti-alpha-4 agent within the scope of this invention. Discussions of appropriate controlled release dosage forms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems. Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

The methods of the invention can be used to treat a patient that is affected with a disorder involving or arising from pathological inflammation, or to prophylactically treat a patient at risk for a particular disorder. The dosage regimes that are necessary for prophylactic versus therapeutic treatment can vary, and will need to be designed for the specific use and disorder treated.

In some methods, two or more agents (e.g., monoclonal antibodies with different binding specificities) are administered simultaneously, in which case the dosage of each agent administered falls within the ranges indicated. Intervals can also be irregular as indicated by measuring receptor saturation levels or by following other indicia of the disease process.

Those of skill will readily appreciate that dose levels can vary as a function of the specific agent, the severity of the symptoms and the susceptibility of the subject to side effects. Some of the specific agents are more potent than others. Preferred dosages for a given agent are readily determinable by those of skill in the art by a variety of means. A preferred means is to measure the physiological potency of a given agent.

Therapeutic Indications

The controlled release formulations of the present invention can be used to obtain a wide range of desirable effects. Particularly the formulations of the invention are useful in treating essentially any disease state or symptom that is treatable by long term administration of anti-inflammatories that target pathological inflammation.

The invention also provides methods of treatment that exploit the ability of anti-alpha-4 integrin agents to block alpha-4-dependent interactions. The alpha-4-dependent interaction with the VCAM-1 ligand on endothelial cells is an early event in many inflammatory responses, including those of the central nervous system. Undesired diseases and conditions resulting from inflammation and having acute and/or chronic clinical exacerbations include multiple sclerosis (Yednock et al., 1992 *Nature* 356: 63; Baron et al., 1993. *J. Exp. Med.* 177: 57), meningitis, encephalitis, stroke, other cerebral traumas, inflammatory bowel disease (IBD) including ulcerative colitis and Crohn's disease (CD) (Hamann et al., 1994 *J. Immunol.* 152: 3238), (Podolsky et al., 1993 *J. Clin. Invest.* 92: 372), rheumatoid arthritis (van Dinther-Janssen et al., 1991 *J. Immunol.* 147: 4207; van Dinther-Janssen et al., 1993 *Annals Rheumatic Diseases* 52: 672); Elices et al., 1994 *J. Clin. Invest.* 93: 405); Postigo et al., 1992 *J. Clin. Invest.* 89: 1445), asthma (Mulligan et al., 1993 *J. Immunol.* 150: 2407) and acute juvenile onset diabetes (Type 1) (Yang et al., 1993 *PNAS* 90: 10494); Burkly et al., 1994 *Diabetes* 43: 529); Baron et al., 1994 *J. Clin. Invest.* 93: 1700), AIDS dementia (Sasseville et al., 1994 *Am. J. Path.* 144: 27); atherosclerosis (Cybulsky et al., 1991 *Science* 251: 788-91, Li et al., 1993 *Arterioscler. Thromb.* 13: 197), nephritis (Rabb et al., 1995 *Springer Semin. Immunopathol.* 16: 417-25), retinitis, atopic dermatitis, psoriasis, myocardial ischemia, chronic prostatitis, complications from sickle cell anemia, lupus erythematosus, and acute leukocyte-mediated lung injury such as occurs in adult respiratory distress syndrome.

Inflammatory bowel disease is a collective term for two similar diseases referred to as Crohn's disease (CD) and ulcerative colitis. CD is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of joints. See e.g., Paul, *Immunology* (3d ed., Raven Press, 1993).

Another indication for chronic dosage of anti alpha-4 agents is in treatment of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD8^+$ cells, $CD4^+$ cells and monocytes are all involved in the rejection of transplant tissues. Antibodies directed to alpha-4 integrin are useful, inter alia, to block alloantigen-induced immune responses in the donee thereby preventing such cells from participating in the destruction of the transplanted tissue or organ. See, e.g., Paul et al., 1996 *Transplant International* 9: 420-425; Georczynski et al., 1996 *Immunol.* 87: 573-580); Georczynski et al., 1995 *Transplant. Immunol.* 3: 55-61); Yang et al., 1995 *Transplantation* 60: 71-76); Anderson et al., 1994 *APMIS* 102: 23-27.

A related use for anti alpha-4 agents is in modulating the immune response involved in "graft versus host" disease (GVHD). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of anti alpha-4 agents of the invention is inhibiting tumor metastasis. Several tumor cells have been reported to express alpha-4 integrin and antibodies to alpha-4 integrin have been reported to block adhesion of such cells to endothelial cells (Steinback et al., 1995 *Urol. Res.* 23: 175-83); Orosz et al., 1995 *Int. J. Cancer* 60: 867-71); Freedman et al., 1994 *Leuk. Lymphoma* 13: 47-52); Okahara et al., 1994 *Cancer Res.* 54: 3233-6).

A further use of the anti-alpha-4 agents is in treating multiple sclerosis. Multiple sclerosis (MS) is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against alpha-4 beta-1 integrin have been shown to block the adhesion of leukocytes to the endothelium, and thus prevent inflammation of the central nervous system and subsequent paralysis in the animals.

The onset of MS may be dramatic or so mild as to not cause a patient to seek medical attention. The most common symptoms include weakness (in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

The course of MS is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia in individual patients. In one aspect of the invention, patients will preferably be treated when the patient is in remission rather then in a relapsing stage of the disease.

Short-term use of either adrenocorticotropic hormone (ACTH) or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and Copaxone® (formerly known as copolymer 1). These three drugs have been shown to significantly reduce the relapse rate of the disease. These drugs are typically self-administered intramuscularly or subcutaneously.

None of the currently available treatments inhibit demyelination or MS. One aspect of the invention contemplates treating MS with agents disclosed herein either alone or in combination with other standard treatment modalities. Standard treatment modalities include but are not limited to the following. Additional treatment modalities not discussed herein for use in treating MS in combination with the methods and compositions disclosed herein depending on the state of disease in the patient would be evident to the skilled practitioner. Such additional treatment modalities for MS other pathological inflammation would include other immunomodulators or immunosupressants.

The agents and pharmaceutical compositions discussed supra can be chronically administered for prophylactic and/or therapeutic treatments of the previously listed inflammatory disorders, including multiple sclerosis, inflammatory bowel disease, asthma, atherosclerosis, rheumatoid arthritis, organ or graft rejection and graft versus host disease. In therapeutic applications, compositions are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose.

In prophylactic applications, pharmaceutical compositions are chronically administered to a patient susceptible to, or otherwise at risk of, a particular disease in an amount sufficient to eliminate or reduce the risk or delay the outset of the disease. Such an amount is defined to be a prophylactically effective dose. In patients with multiple sclerosis in remission, risk may be assessed by NMR imaging or, in some cases, by presymptomatic indications observed by the patient.

Effective dosage regimes of the compositions of the present invention, for the treatment of the above described conditions will vary depending upon many different factors, including means of administration, target site, physiological state of the patient, and other medicaments administered. Thus, treatment dosages will need to be titrated to optimize safety and efficacy. In general, each administration of the dosage regime will range from about 0.0001 to 100 mg/kg, and more usually 0.01 to 5 mg/kg of the host body weight. One preferred dosage regimen is 300 mg administered once per month for a period of at least 6 months, more preferably 12 months and perhaps over the course of several years. Another dosage regimen that is preferred is a 3 mg per kilogram of patient weight per month. Such a regimen may be preferable for pediatric or adolescent patients in need of therapy.

Combination Therapies

The anti-alpha-4 agents of the invention can be used with effective amounts of other therapeutic agents against acute and chronic inflammation. Such agents include other antagonists of adhesion molecules (e.g., other integrins, selectins, and immunoglobulin (Ig) super family members (see Springer, 1990 *Nature* 346: 425-433; Osborn, 1990 *Cell* 62: 3; Hynes, 1992 *Cell* 9: 11). Integrins are heterodimeric transmembrane glycoproteins consisting of an α chain (120-180 kDa) and a β chain (90-110 kDa), generally having short cytoplasmic domains. For example, three important integrins (i.e., LFA-1, Mac-1 and P150,95) have different alpha subunits, designated CD11a, CD11b and CD11c, and a common beta subunit designated CD18. LFA-1 ($\alpha_L\beta_2$) is expressed on lymphocytes, granulocytes and monocytes, and binds predominantly to an Ig-family member counter-receptor termed ICAM-1 and related ligands. ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1. The third β2 integrin, P150,95 ($\alpha_x\beta_2$), is also found on neutrophils and monocytes. The selectins consist of L-selectin, E-selectin and P-selectin.

Other anti-inflammatory agents that can be used in combination with the anti-alpha-4 agents include antibodies and other antagonists of cytokines, such as interleukins IL-1 through IL-13, tumor necrosis factors α and β, interferons α, β and γ, tumor growth factor beta (TGF-β), colony stimulating factor (CSF) and granulocyte monocyte colony stimulating factor (GM-CSF). Other anti-inflammatory agents include antibodies and other antagonists of chemokines such as MCP-1, MIP-1α, MIP-1β, RANTES, exotaxin and IL-8. Other anti-inflammatory agents include NSAIDS, steroids and other small molecule inhibitors of inflammation. Formulations, routes of administration and effective concentrations of agents for combined therapies are as described above for the humanized antibodies against alpha-4 integrin.

Additional agents for use in combination with agents which mediate alpha-4 integrin or dimers comprising alpha-4 integrin and treat inflammatory bowel disease (IBD), Crohn's Disease (CD) and ulcerative colitis (UC), include but are not limited to 5-aminosalicylates, glucocorticoids, thioguanine derivatives, methotrexate (MTX), cyclosporine, antibiotics, and infliximab.

5-Aminosalicylates include sulfasalazine (also known as Azulfidine) which is a conjugate of mesalamine linked to sulfapyridine by a diazo bond and is usually administered in an amount of 500 mg/day to about 6 g/day. 5-Aminosalicylates can also be co-administered with a glucocorticoid. Preferably, a 5-aminosalicylate is used in combination therapy with one of the other agents discussed herein to treat ulcerative colitis, however it can also be used to treat Crohn's disease. Non-sulfonamide containing formulations of mesalamine include but are not limited to ASACOL®, CLAVERSA, SALOFALK, PENTASA®, DIPENTUM®, COLAZIDE and ROWASA®.

Glucocorticoids have been a mainstay of treatment for acute severe exacerbations of IBD since 1955, when they first where shown to be efficacious in UC. Oral prednisone can be administered in conjunction with any of the agents disclosed herein. Typically, 20 to 40 mg of oral prednisone is administered once a day. Glucocorticoids can also be administered intravenously and via enemas in combination with or concurrently with or within a short time before/after an anti-alpha-4 integrin agent is administered. For example, hydrocortisone is available as a retention enema (100 mg/GO mL) and the usual dose is one 60-mL enema per night for 2 to 3 weeks. This can be altered when used in combination with the therapies and agents discussed herein as would be understood by the artisan of ordinary skill. Other steroids that can be used include, but are not limited to, prednisolone methasulfobenzoate, tixocortol pivalate, fluticasone propionate, beclomethasone dipropionate, and budesonide.

Thioguanine derivatives are also useful in the treatment of IBD, CD and UC. These include but are not limited to 6-mercaptopurine (6-MP) and azathioprine (IMURAN). The two drugs can be used interchangeably in combination with any of the alpha-4 integrin modulating agents discussed herein.

Methotrexate (MTX) is also contemplated for use in combination with the alpha-4 integrin regulatory agents discussed herein. Preferably, MTX is administered via intramuscular injection (i.m.) to the subject in combination with an anti-alpha-4 integrin agent. MTX is effective in steroid-dependent CD, but not as useful in UC. MTX can be administered in amounts of about 15 to about 25 mg per week per subject or as necessary as determined by the artisan of ordinary skill.

Cyclosporines (e.g., SANDIMMUNE®, NEORAL®) can also be used in combination with the alpha-4 integrin modulating agents discussed herein to treat pathological inflammation of the bowel. This can be used to treat acute, severe UC, which does not respond to glucocorticoids.

Infliximab (i.e., REMICADE®) can also be used to treat CD in combination with the alpha-4 integrin modulating agents indicated herein. Infliximab is an immunoglobulin that binds to TNF and thereby neutralizes its activity. Other anti-TNF antibodies, such as CDP571, can also be used in combination with the alpha-4 integrin modulating agents disclosed herein.

Antibiotics are also contemplated for use in combination with the alpha-4 integrin modulating agents indicated herein to modulate UC, IBD and CD. For example, patients can be treated with metronidazole or ciprofloxacin (or pharmacological equivalents thereof) in combination with an alpha-4 integrin mediating agent or in the form of an admixture.

Also contemplated is the use of supportive therapies for IBD, CD and UC in conjunction with agents that mediate alpha-4 integrin or dimers comprising alpha-4 integrin and treat inflammatory bowel disease, Crohn's Disease and ulcerative colitis. Supportive therapies include, but are not limited to, analgesics, anticholinergic and antidiarrheal agents. Combining such supportive therapies can be useful in the beginning of a treatment regimen in reducing a patient's symptoms and improving their quality of life. Supportive therapies include administering oral iron, folate, and vitamin $B_{12}$. Antidiarrheal agents include, but are not limited to diphenoxylate, codeine, loperamide, and anticholinergics (or pharmacological equivalents thereof), which can be administered to patients with mild disease to reduce the frequency of bowel movements and relive rectal urgency. Cholestyramine can be used in patients to prevent bile salt-induced colonic secretion in patients who have already undergone limited ileocolic resections prior to treatment with the chronic regimens described herein. Anticholinergic agents include, but are not limited to, clidinium bromide, dicyclomine hydrochloride, tincture of belladonna and the like, and are useful to reduce abdominal cramps, pain and rectal urgency.

For treatment of MS, the anti-alpha-4 integrin agents (e.g., anti-alpha-4 integrin antibodies, small compound alpha-4 integrin antagonists and the like) can be combined with other compounds or compositions used to treat, ameliorate or palliate symptoms associated with MS.

Other agents utilized to treat, ameliorate or palliate symptoms associated with MS, include but are not limited to: muscle relaxants (e.g., Diazepam, cyclobenzaprine, Clonazepam, clonidine, primidone, and the like), anticholinergics (e.g., propantheline, dicyclomine, and the like), central nervous system stimulants (e.g., Pemoline), non-steroidal anti-inflammatory agents (NS such as ibuprofen, naproxen and ketoprofen), interferons, immune globulin, glatiramer (Copaxone®), mitoxantrone (Novantrone®), misoprostol, tumor necrosis factor-alpha inhibitors (e.g., Pirfenidone, infliximab and the like) and corticosteroids (e.g., glucocorticoids and mineralocorticoids).

Common agents for treating multiple sclerosis include interferon beta-1b (Betaseron®), interferon beta-1a (Avonex®), high-dose interferon beta-1a (Rebif), Glatiramer (Copaxone®), immune globulin, mitoxantrone (Novantrone®), corticosteroids (e.g., prednisone, methylprednisolone, dexamethasone and the like). Other corticosteroids may also be used and include but are not limited to cortisol, cortisone, fludrocortisone, prednisolone, 6α-methylprednisolone, triamcinolone, and betamethasone.

Dosage forms of the agents to be used in combination with the compounds and compositions disclosed herein would vary depending on the subject and drug combination being utilized. For example, interferons are typically administered as follows: Interferon beta-1a (Avonex®) is administered 30 µg once a week; interferon beta-1a is administered at about 22 µg or 44 µg three times a week; and interferon beta-1b (Betaseron®) is administered at 250 µg on alternate days (Durelli et al., *Lancet* 359: 1453-60, 2002). Typically the interferons are administered for relapsing or remitting multiple sclerosis. Thus in combination with the anti-alpha-4 integrin agents disclosed herein, preferred ranges of interferons may include about 0.1 µg to about 250 µg and more preferably about 0.5 µg to about 50 µg, depending on the manner in which the agent is administered in conjunction with the other anti-alpha-4 integrin compounds and compositions disclosed herein.

NS or NSAIDs contemplated for use with this invention include but are not limited to non-selective COX inhibitors and selective COX-2 inhibitors. Non-selective COX inhibitors include but are not limited to salicylic acid derivatives (e.g., aspirin, sodium salicylates, choline magnesium trisalicylate, salsalate, diflunisal, sulfasalazine, and olsalazine), para-aminophenol derivatives (e.g., acetaminophen), indole and indene acetic acids (e.g., tolmetin, diclofenac, and ketorolac), heteroaryl acetic acids (e.g., abuprofen, naproxen, flurbiprofen, ketoprofen, fenprofen, and oxaprozin), anthranilic acids or fenamates (e.g., mefenamic acid and meclofenamic acid), enolic acids (e.g., oxicams such as piroxicam and meloxicam), and alkanones (e.g., nabumetone). Selective COX-2 inhibitors include diaryl-substituted furanoses (e.g., rofecoxib), diaryl-substituted pyrazoles (e.g., celecoxib), indole acetic acids (e.g., etodolac), and sulfonanilides (e.g., nimesulide). NS are oftentimes administered in combination with interferon to lessen the flu-like symptoms experienced by patients receiving, for example, Avonex®. Common NS agents include naproxen, ibuprofen and ketoprofen. Paracetamol is also frequently administered to patients. See, Reess et al., 2002 *Mult. Scler.* 8: 15-8.

Glatiramer acetate (GA, Copaxone®) is a synthetic molecule that inhibits activation of myelin basic protein-reactive T cells and induces a T-cell repertoire characterized by anti-inflammatory effects. Moreover, Glatiramer can access the central nervous system (CNS), whereas interferon-beta cannot (Dhib-Jalbut, 2002 *Neurology* 58: S3-9; Weinstock-Guttman et al., 2000 *Drugs* 59: 401-10).

Mitoxantrone is an anthracenedione synthetic agent, which has been shown to be effective for treating secondary progressive multiple sclerosis (SP-MS). However, use of this drug is again limited by its cumulative cardiotoxicity (Weinstock-Guttman et al., 2000).

Tumor necrosis factor-alpha (TNF-α) may be a key cytokine in demyelination (Walker et al., 2001 *Mult. Scler.* 7: 305-12). Thus use of agents that antagonize TNF-α function or inhibit its synthesis may be useful in combination with the agents and compounds disclosed herein. This can include anti-TNF-α antibodies (e.g., infliximab) as well as agents such as pirfenidone. Pirfenidone is a non-peptide drug, which has been shown to decrease synthesis of TNF-α and to block receptors for TNF-α. Id.

The long mainstay in most demyelinating conditions and diseases has been the use of ACTH, glucocorticoids and corticoid steroids. These agents are used for their anti-edema and anti-inflammatory effects. ACTH is commonly administered to a subject at 80 U given intravenously in 500 mL of 5% dextrose and water over 6-8 hours for 3 days. It may also be administered at 40 U/ml intramuscularly at a dose of 40 U every 12 hours for 7 days, with the dose then reduced every 3 days. See, S. Hauser, "Multiple sclerosis and other demyelinating diseases," in *Harrison's Principles of Internal Medicine* 2287-95 (13$^{th}$ ed., Isselbacher et al., ed. 1994).

Methylprednisolone is typically administered slowly in 500 ml D5W over 6 hours, preferably in the morning. Common dosages include 1000 mg daily for 3 days, 500 mg daily for 3 days and 250 mg daily for 3 days. Id. A methylprednisolone-prednisone combination is also commonly administered. Typically about 1,000 mg of intravenous methylprednisolone is administered over three days followed by oral prednisone at 1 mg/kg per day for 14 days. Thus, for use in combination with the compounds and compositions disclosed herein, the steroids may be administered in amounts ranging from about 1 to about 1,000 mg/kg over about 1 to 14 days, as needed.

A side effect in demyelinating conditions such as MS, is fatigue and decreased cognitive function. Agents such as amantadine hydrochloride and pemoline have been frequently used to treat fatigue associated with MS (Geisler et al., 1996 *Arch. Neurol.* 53: 185-8).

The benefit of such combination therapies is that it may lessen the class-specific and agent-specific side effects currently encountered with some of the drugs. Class-specific side effects of interferon-beta include fever, chills, myalgias, arthralgias and other flu-like symptoms beginning 2-6 hours after injection and typically resolving 24 hours post injection. Occasionally interferon-beta also induces transient worsening of preexisting MS symptoms. Agent specific side effects include injection site reactions with interferon beta-1b. Management of these effects can be accomplished by tailoring the dose and time of administration, prescribing appropriate combinations of acetaminophen, non-steroidal anti-inflammatory drugs (NS or NSAIDS) and steroids. See Munschauer et al., 1997 *Clin. Ther.* 19: 883-93.

Thus, combinations of drugs that can lessen the quantity of a particular drug administered may reduce adverse side effects experienced by a patient.

When administered in combination, the small compound alpha-4-integrin antagonists may be administered in the same formulation as these other compounds or compositions, or in a separate formulation. When administered in combination, the anti-alpha-4-antibodies are generally administered in a separate formulation than the other compounds and compositions. When administered in combinations, the anti-alpha-4 agents may be administered prior to, following, or concurrently with the other compounds and compositions used to treat, ameliorate, or palliate symptoms.

EXAMPLES

The following examples are put forth so as to provide those of ordinary skill in the art with a complete disclosure and description of representative examples of how to make and use embodiments of the present invention, and are not intended to limit the scope of what the inventors regard as their invention, nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Controlled Trial of Natalizumab in Relapsing Multiple Sclerosis

Patient Population

Twenty-six clinical centers in the United States, Canada, and the United Kingdom enrolled 213 patients from September 1999 until May 2000. The institutional review board or central and local ethics committee approved the protocol. All patients gave written informed consent. Study oversight was provided by an independent safety data monitoring committee.

Eligible subjects were required to be age 18 through 65 years, with Poser criteria defined clinically or laboratory supported definite MS, either relapsing-remitting or secondary progressive, (Poser et al., 1983 *Ann. Neurol.* 13: 227-31; Lublin et al., 1996 *Neurology* 46: 907-11), a history of at least two relapses within the previous two years, a base-line Kurtzke Expanded Disability Status Score (EDSS) (Kurtzke, 1983 *Neurology* 33: 1444-52) between 2 and 6.5, and a minimum of three lesions on $T_2$-weighted brain MRI. Patients were excluded if they received immunosuppressive or immunomodulating treatments within the past 3 months, or experienced a relapse, or received systemic corticosteroids within the past 30 days.

Study Design and Randomization

Patients were randomly assigned to one of three treatment groups: 3 mg/kg natalizumab, 6 mg/kg natalizumab, or placebo according to a computer-generated block randomization schedule. Patients received six intravenous infusions at 28-day intervals and then had six months of safety follow-up. The investigator, all other study personnel, and patients were blinded to treatment assignment.

Study Procedures and Endpoints

Unenhanced proton density $T_2$-weighted and Gd-enhanced $T_1$-weighted MRI brain scans were obtained during the screening phase (month-1), immediately before each treatment (month 0-5), and one month after the last treatment (month 6). Follow-up MRI scans were obtained at months 9 and 12. Forty-six contiguous, 3-mm thick, axial slices through the brain were acquired. MRI analysis was performed by a single center blinded to patient treatment and history. Lesions were identified on hard copy images by two experienced clinicians working by consensus.

The prospective primary outcome measure was the number of new Gd-enhancing lesions over the 6-month treatment period, defined as the period following the first infusion to one month after the last infusion. Other MRI parameters evaluated included: the number of persistent Gd-enhancing lesions (enhancing lesions that had also enhanced on the previous monthly scan); the volume of Gd-enhancing lesions (measured by a semiautomated local thresholding method; Grimaud et al., 1996 *Magn. Reson. Imaging* 14: 495-505); the number of new active lesions (i.e., new Gd-enhancing lesions plus new or enlarging, non-enhancing T2 lesions); and the number of active scans (i.e., containing one or more new Gd-enhancing lesions).

Clinical endpoints included relapse frequency and changes in EDSS, and a self-reported global assessment using a visual-analog scale (VAS). All adverse events were recorded. Patients were examined at scheduled quarterly intervals, and at unscheduled visits for suspected relapses, by the treating and evaluating neurologists who were both unaware of the patient's treatment assignment. The treating neurologist performed a medical history and examination, and recorded adverse events. The evaluating neurologist assessed neurological status and assigned an EDSS score without knowledge of the patient's history or prior EDSS scores.

An objective relapse was defined as the occurrence of an acute episode of new or worsening MS symptoms lasting at least 48 hours following a stable period of at least 30 days. It was also accompanied by an increase of at least one point in the EDSS score, an increase of at least one point on two functional system scores (FSS), or an increase of at least two points on one FSS compared with base-line, as determined by the evaluating neurologist. Neurological symptoms that did not meet the above criteria for relapse, but were assessed by the treating neurologist to constitute a relapse, were also recorded (total relapses).

On a visual analog scale (VAS), patients marked a location along a 10-cm line that reflected their assessment of their overall well-being at base-line and after 3 and 6 months treatment, with higher scores reflecting greater well-being.

Patients were followed clinically to month 12. Patients who discontinued treatment, but who did not reach the endpoint, were encouraged to return for follow-up assessments.

Statistical Analysis

Sample size estimates were based on the number of new Gd-enhancing lesions observed during the first 12 weeks following the first infusion in a previous clinical trial of natalizumab (Tubridy et al., 1999 Neurology 53: 466-72). Based on the results of this previous trial, and using sample size methodology appropriate for a two-sided, two-group comparison at the 5 percent level of significance, based on the Wilcoxon-Mann-Whitney statistic (Noether, 1987 J. Amer. Stat. Assoc. 82: 645-7), it was calculated that approximately 73 patients were needed in each group for 80 percent power.

The primary comparison of the number of Gd-enhancing lesions between 6 mg/kg natalizumab and placebo as well as Gd-enhancing volumes were evaluated with the Wilcoxon-Mann-Whitney rank-sum test. Missing values due to one or more MRI scans not being performed were imputed by replacing the missing value with the average number of lesions on available scans for that patient. MRI scans obtained from patients who received systemic corticosteroids within the previous 30 days were discarded and treated as missing values. The Cochran-Mantel-Haenszel correlation statistic, using equally spaced scores for the groups and rank scores for the primary outcome variable, was used to test for a dose-response relationship using data from all three groups.

Pearson's chi-square test was used to compare proportions of patients with relapses. Changes from baseline in EDSS and VAS were analyzed using a two-way ANOVA with study center and treatment groups as independent variables.

All analyses included all randomized patients and followed the intention-to-treat principle. All reported P values are two-tailed. There were no significant differences in demographic characteristics, MS disease history, entry EDSS, and MRI parameters among the three groups at base-line (Table 1).

TABLE 1

DEMOGRAPHIC AND BASELINE CHARACTERISTICS OF RANDOMIZED PATIENTS

| CHARACTERISTIC | | PLACEBO (N = 71) | Natalizutuab 3 MG/KG (N = 68) | 6 MG/KG (N = 74) |
|---|---|---|---|---|
| Age, years | Mean | 42.9 | 42.8 | 44.9 |
| | Range | 22-66 | 22-65 | 30-63 |
| Gender N (%) | Male | 25 (35.2) | 21 (30.9) | 15 (20.3) |
| | Female | 46 (64.8) | 47 (69.1) | 59 (79.7) |
| MS category N (%) | R-R | 45 (63.4) | 47 (69.1) | 52 (70.3) |
| | S-P | 26 (36.6) | 21 (30.9) | 22 (29.7) |
| EDSS | Mean | 4.40 | 4.21 | 4.32 |
| | Range | 2.0-6.5 | 1.0-6.5 | 0.0-6.5 |
| Disease duration | Mean | 10.2 | 11.6 | 13.1 |
| Years | Range | 1-32 | 0-40 | 2-39 |
| Number of relapses | Mean | 3 | 2.9 | 3.1 |
| In past 2 years | Range | 2-12 | 2-10 | 2-8 |
| Time since last relapse | Mean | 6.5 | 7.2 | 6 |
| Months | Range | 2-17 | 2-24 | 2-22 |
| Screening T$_1$-weighted MRI (Month 1) | | | | |
| Number (%) of scans with one or more Gd-enhancing lesion(s) | | 28 (40) | 29 (43) | 29 (40) |
| Number of Gd-enhancing brain lesions | | | | |
| | Mean | 1.6 | 1.5 | 1.7 |
| | Range | 0-42 | 0-18 | 0-23 |
| Baseline T$_1$-weighted MRI (Month 0) | | | | |
| Number (%) of scans with one or more new Gd-enhancing lesion(s) | | 22 (31) | 29 (43) | 32 (43) |
| Number of new Gd-enhancing brain lesions | | | | |
| | Mean | 1.3 | 1.3 | 1.4 |
| | Range | 0-28 | 0-32 | 0-12 |

Primary Outcome

Figure 1:
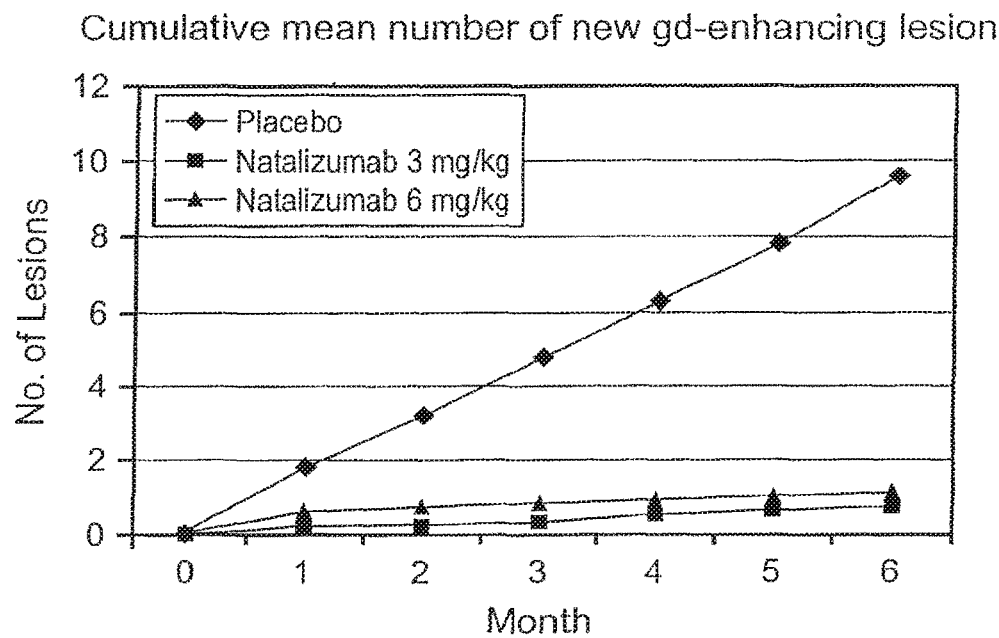
FIG. 1 is a line graph illustrating the cumulative mean number of new Gd-enhancing lesions in MS patients following dosing with natalizumab.

Patients in the placebo group exhibited an average of 9.6 new Gd-enhancing lesions during the six-month treatment period. The corresponding values in the groups receiving natalizumab were 0.7 for the 3 mg/kg group (P<0.0001) and 1.1 for the 6 mg/kg group (P<0.0001)(see Table 2). This difference constituted a 93% and an 88% reduction in new Gd-enhancing lesions in the 3 mg/kg and 6 mg/kg groups, respectively. A difference between treatment groups compared with placebo was apparent after the first infusion (FIG. 1).

TABLE 2

SUMMARY OF MRI ACTIVITY DURING TREATMENT (MONTHS 1-6) AND FOLLOW-UP (MONTHS 9 AND 12)

| | PLACEBO | 3 MG/KG | 6 MG/KG | P VALUE* |
|---|---|---|---|---|
| New enhancing lesions M1- | | | | |
| Mean | 9.6 | 0.7 | 1.1 | (i) <0.0001 |
| Median | 2.0 | 0 | 0 | (ii) <0.0001 |
| SD | 27.4 | 2.1 | 2.7 | |
| Persistent enhancing lesions M1-6 | | | | |
| Mean | 3.6 | 0.8 | 1.3 | <0.0001 |
| Median | 1 | 0 | 0 | |
| SD | 6.5 | 1.9 | 2.6 | |

TABLE 2-continued

SUMMARY OF MRI ACTIVITY DURING TREATMENT
(MONTHS 1-6) AND FOLLOW-UP (MONTHS 9 AND 12)

|  | PLACEBO | 3 MG/KG | 6 MG/KG | P VALUE* |
|---|---|---|---|---|
| New active lesions M1-6 |  |  |  |  |
| Mean | 9.7 | 0.8 | 1.1 | <0.0001 |
| Median | 2.0 | 0 | 0 |  |
| SD | 27.4 | 2.2 | 3 |  |
| Active scans M1-6 (%) | 39% | 9% | 11% | (i) <0.0001 |
|  |  |  |  | (ii) <0.0001 |
| Enhancing lesion volume M1-6(mm³) |  |  |  |  |
| Mean | 1169.0 | 156 | 279.0 | (i) 0.005 |
| Median | 266 | 0 | 0 | (ii) 0.01 |
| SD | 2666 | 359.0 | 632.0 |  |
| New enhancing lesions M9 and 12. |  |  |  |  |
| Mean | 2.5 | 2.6 | 2.1 | (i) 0.90 |
| Median | 1.0 | 0.5 | 0 | (ii) 0.59 |
| SD | 4.37 | 4.58 | 4.96 |  |
| Persistent enhancing lesions M9 and 12 |  |  |  |  |
| Mean | 0.2 | 0.1 | 0.1 | 0.029 |
| Median | 0 | 0 | 0 |  |
| SD | 0.64 | 0.32 | 0.3 |  |
| New active lesions M9 and 12 |  |  |  |  |
| Mean | 2.7 | 2.8 | 2.3 | 0.424 |
| Median | 1.0 | 0.5 | 1.0 |  |
| SD | 4.49 | 5.69 | 5.11 |  |
| Active scans M9 and 12 (%) | 42% | 40% | 35% |  |
| Enhancing lesion volume M9 and 12(mm³) |  |  |  |  |
| Mean | 427.0 | 323 | 233 | 0.260 |
| Median | 88.0 | 31.0 | 0 |  |
| SD | 797.0 | 591.0 | 686 |  |

*(i) comparison of placebo vs. 3 mg/kg natalizumab;
(ii) comparison placebo vs. 6 mg/kg natalizumab.

Secondary MRI Outcomes

Figure 2:
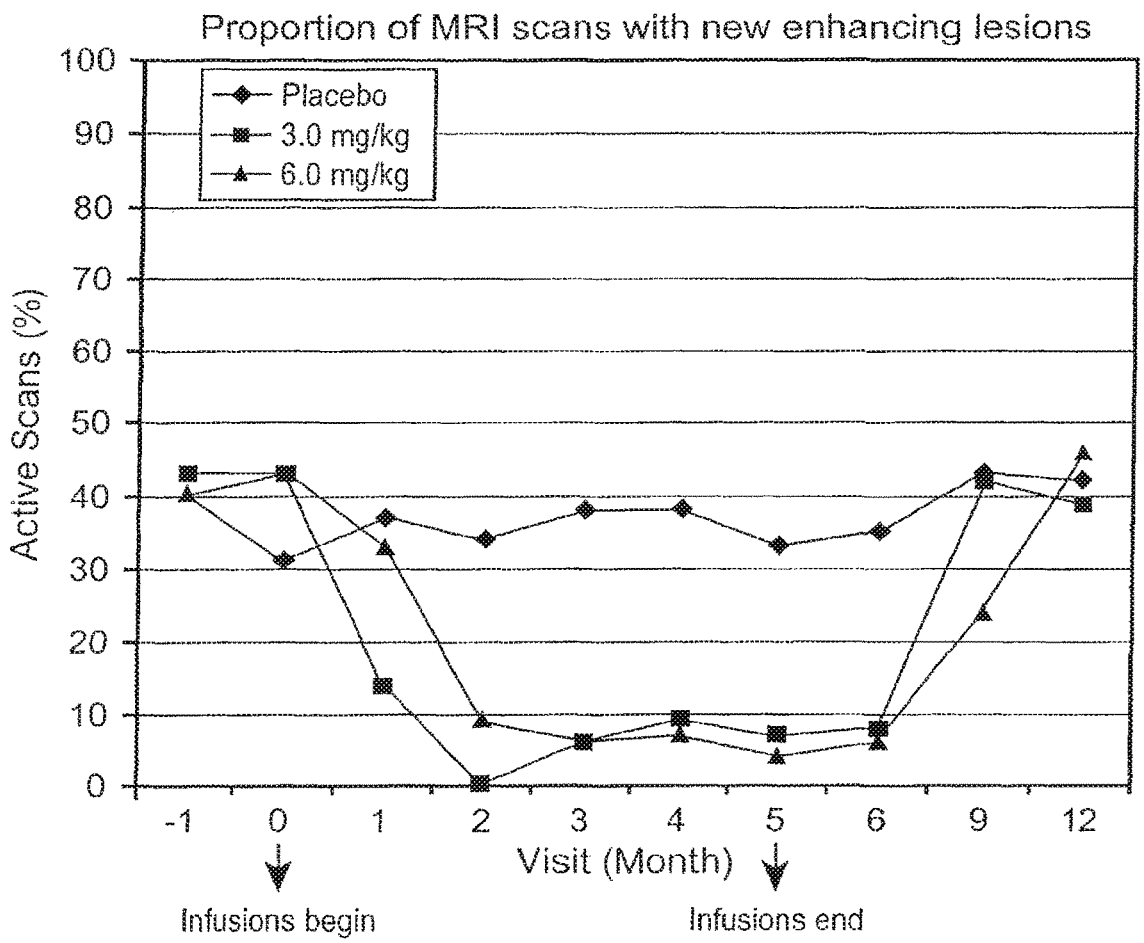
FIG. 2 shows the percentage of active scans at each time point during the natalizumab MS study. Active scans are those containing one or more new Gd-enhancing lesions.

There was a significant and marked reduction in the cumulative number of persistent enhancing lesions, new active lesions, total volume of enhancing lesions, and percentage of active scans from months 1-6 (Table 2; FIG. 2).

Clinical Efficacy Outcomes

During the six month treatment period, a total of 35 relapses were reported in 26 of the 71 placebo patients; 18 relapses were reported in 13 of the 68 patients receiving 3 mg/kg natalizumab, and 15 relapses were reported in 14 of the 74 patients receiving 6 mg/kg (P=0.05, placebo vs. all natalizumab-treated patients). Applying the more stringent objective relapse criteria, the effect was equally strong: 18 relapses in 15 placebo patients; 3 relapses in 3 patients receiving 3 mg/kg natalizumab; 8 relapses in 8 patients receiving 6 mg/kg natalizumab (P=0.05). More relapses in the placebo group required steroid treatment than in the treated arms (22 in placebo, 5 in the 3 mg/kg natalizumab, and 7 in the 6 mg/kg natalizumab groups, P=0.007, placebo vs. all natalizumab-treated patients).

On the VAS, patients in the placebo group reported no change, while those in the natalizumab groups reported an improvement in well-being by month 6, at which time the difference between groups was significant (P=0.033, placebo vs. all natalizumab-treated patients). No significant changes in EDSS were observed in any group during treatment.

Antibody Concentration and Receptor Saturation

Serum samples were collected from patients at each visit and analyzed quantitatively for antibodies directed specifically against natalizumab using an enzyme linked immunosorbant assay (ELISA). Natalizumab serum levels and receptor occupancy by natalizumab were also measured in a subgroup of 12 to 14 patients per treatment group before each infusion and at 2 hours, 24 hours, 1, 2, and 3 weeks after the first and last infusions.

Serum antibody concentrations were determined using an ELISA assay. In brief, a 2.0 µg/mL solution of a capture antibody that binds specifically to natalizumab was prepared in a solution containing sodium bicarbonate to pH 8.3. 100 µL of the antibody solution was added to each well of a Costar 96-well microtiter plate. The plate was covered with plate sealing tape and incubated at ambient temperature for 12-26 hours. The plate was aspirated, 200 µL of blocking buffer (0.25% casein in PBS, pH 7.4) added to each well, and incubated for an additional hour at ambient temperature. Plates were then either dessicated and stored for later use, or washed once with 300 µL wash buffer (TBS, pH 7.5 containing 0.05% Tween-20). If plates were dessicated, they were rehydrated just prior to use by adding 300 µL wash buffer to each well and incubating for 1-2 minutes. Plates were aspirated and inverted onto tissue paper to absorb excess moisture.

Test samples were diluted in casein diluent prior to the ELISA (0.25% casein in PBS, with 0.05% Tween 20, pH 7.4). Typically, two or three dilutions of each sample are tested to ensure the natalizumab values were accurate. Dilution control samples were also prepared using known quantities of natalizumab to monitor the accuracy of the remaining steps.

100 µL of reference standard, test sample, or dilution control sample was added to each well, and the plate incubated between 60-75 minutes at ambient temperature. The plates were washed three times with wash buffer and remaining moisture removed. 100 µL freshly diluted mouse anti-human IgG4-alkaline phosphatase conjugate was added to each well, and the plates were incubated for an additional 60 minutes at ambient temperature. Following incubation, plates were washed four times with wash buffer, and remaining moisture removed. 100 µL fluorescent substrate A was added using a calibrated multichannel pipetter, and the plates incubated 45-60 minutes at ambient temperature. The levels in each well were determined using an fmax Fluorescence Microplate Reader using the SOFTmax Pro Version 1.3.1 protocol file conc102.ppr.

The results are as shown in FIGS. 3 and 4. As shown in these figures, levels of natalizumab decreased between dosings, and by month 7 or 8 (i.e., 2 to 3 months following the final dosing) the antibody was undetectable in the majority of patients.

As well as measuring serum antibody concentration, levels of receptor saturation, and specifically levels of VLA-4 saturation, were determined during the dosing study using FACS analysis. Determination of VLA-4 saturation was determined by an indirect immunoassay using flow cytometry.

Approximately 1 mL of a blood sample from a patient was aliquoted into two 15 mL polypropylene tubes, and cold wash buffer (human serum (Scantibodies Laboratory, Inc. Part 3SH341) diluted to 3% in PBS) added to the 14 mL mark on the tube. The tubes are centrifuged at 2,200 rpm for 5 minutes at 10-15° C., and the liquid aspirated and discarded. The cell pellet is resuspended in cold wash buffer to a total of 1 mL.

500 μg/mL of a natalizumab stock reference standard is prepared in wash buffer. 20 μL of the diluted natalizumab stock reference was added to the first tube, and 20 μL wash buffer was added to the second tube. Both tubes were incubated on ice for 30 minutes in the dark. After incubation, the tubes were filled with wash buffer up to the 14 mL mark, and centrifuged at 2,200 rpm for 5 minutes in the cold. The supernatant was aspirated, and the wash step repeated a second time. Following the second wash, the cells were resuspended in wash buffer to the 1 mL mark.

10 μL of R-Phycoerythrin (PE)-conjugated anti-human CDw49d antibody (Pharmingen, Cat. 431475X) was added to each tube and the tubes vortexed gently. The tubes were incubated at 2-8° C. for 10-15 minutes in the dark. Following incubation, 2 mL 1× lysing solution, pH 7.4, was added and each tube gently vortexed. The tubes were incubated on ice for 10-15 minutes at 2-8° C., centrifuged 5 minutes in the cold, and the supernatant aspirated from the cell pellet. The cell pellet was resuspended in 4 mL cold staining buffer, and the tubes centrifuged again at 2,200 rpm in the cold. The supernatant was then very carefully removed, 0.5 mL of a fixative solution (Ortho's Fixative pH 7.6) added, and the tubes immediately vortexed to ensure that cells were resuspended in the fixative. The tubes were covered with aluminum foil until FACS assay.

Each sample was then for VLA-4 receptor saturation in the samples with and without analyzed natalizumab using the FACS Calibur flow cytometer and CellQuest™ software. The CellQuest™ software allows acquisition and analysis of data from the flow cytometer.

Receptor saturation levels are shown in FIG. 5. The levels of receptor saturation for months 1-4 were determined prior to that month's dosing. The levels of receptor saturation produced by one month dosage intervals were consistently fairly high, and these chronic levels were sufficient to maintain a suppression of the pathological inflammation and associated physiological hallmarks of the disease. On average, the levels of saturation were maintained for a month at a mean of at least 67% and a median of at least 75%. These levels were sufficient for the suppression of brain lesions in the treated patients (see FIG. 1). The minimum level of saturation determined in the study preinfusion from month 2 to month 5 (and week 21 following administration at month 5) is particularly low as compared to the mean and median values due to a single patient with an antibody response to natalizumab.

As the receptor saturation levels dropped in the patients, so did the efficacy of the treatment. Mean receptor saturation levels of 42% and median receptor saturation levels of 41% receptor saturation in the treated population were not associated with suppression of brain lesions in the patient population (See FIGS. 2 and 5), and thus a chronic receptor saturation level above this is necessary for effective suppression of pathological inflammation using agents such as alpha-4 inhibitors.

Safety and Tolerability

Repeated natalizumab treatment, at either the 3 or 6 mg/kg dose, appeared well tolerated by patients with MS over a six month treatment period. Similar numbers of patients from each group experienced treatment-emergent adverse events. Though not significant, certain adverse events occurred more commonly with natalizumab compared to placebo (Table 3). A sustained mild lymphocytosis was seen in the natalizumab arms over the six month treatment period.

TABLE 3

ADVERSE EVENTS REPORTED MORE COMMONLY IN NATALIZUMAB-TREATED PATIENTS VERSUS PLACEBO*

|  | PLACEBO (71) | 3 MG/KG (68) | 6 MG/KG (74) |
|---|---|---|---|
| Total number of patients with adverse events | 68 (96%) | 62 (91%) | 70 (95%) |
| Body as whole |  |  |  |
| Infection | 10 (14%) | 14 (21%) | 14 (19%) |
| Digestive system |  |  |  |
| Flatulence | 0 | 4 (6%) | 0 (0%) |
| Nervous system |  |  |  |
| Circumoral parasthesia | 1 (1.0%) | 5 (7%) | 2 (3%) |
| Respiratory system |  |  |  |
| Sinusitis | 3 (4%) | 7 (10%) | 3 (4%) |
| Pharyngitis | 8 (11%) | 10 (15%) | 15 (20%) |
| Skin and appendages |  |  |  |
| Rash | 4 (6%) | 6 (9%) | 8 (11%) |
| Urogenital system |  |  |  |
| Infection | 10 (14%) | 14 (21%) | 11 (15%) |

*To be included in the Table, a difference of at least 5 percent in the incidence of adverse events was required between the placebo arm and one of the natalizumab arms.

There were no significant differences in the number of serious adverse events (SAEs) reported in the placebo and treatment arms (i.e., 7 placebo-treated patients reported 11 SAEs, 5 patients receiving natalizumab 3 mg/kg reported 5 SAEs, and 3 patients receiving natalizumab 6 mg/kg reported 4 SAEs). Of these, four were considered to be immune-mediated and related to study drug. There was one anaphylactic reaction with urticaria and bronchospasm in the 3 mg/kg group, which was rapidly reversed with antihistamines and steroid treatment. There were three reports of serum sickness, one in each group including placebo. Only one event was accompanied by a change in complement levels and all occurred at the same investigative site. Overall, these events complicated fewer than one in 250 infusions.

There were no differences in the number of patients that discontinued treatment due to an adverse event between groups (i.e., 3 in the placebo group, 4 in the 3 mg/kg group and 3 in the 6 mg/kg group). There was one death in the study secondary to pleural carcinomatosis complicated by hemothorax in a placebo patient.

Rate of antibody formation was also assessed. Overall, 15 natalizumab-treated patients (11 percent) developed anti-natalizumab antibodies: 13 during the treatment period, and 2 during the post-treatment follow-up period. The clinical relevance, if any, of the presence of anti-natalizumab antibodies is not currently known.

Maximal serum concentrations of natalizumab were dose dependent and there was no significant accumulation observed with repeated dosing. The patients receiving natalizumab at 3 mg/kg exhibited greater than 80% saturation of the VLA-4 receptor during the treatment period; receptor occupancy was higher (approximately 90%) and more prolonged in patients receiving natalizumab 6 mg/kg.

Post-Treatment Follow-Up: Months 6-12

The cumulative number of new enhancing lesions and active scans (months 9 and 12 combined) were similar in all three groups (Table 2). There was a trend to less activity in the 6 mg/kg group at month 9. There was no significant difference in the total number of reported clinical relapses between the three groups: 24 in the placebo group, 24 in the 3 mg/kg group, and 26 in the 6 mg/kg group or in the number of relapses as determined by the predefined objective criteria.

This study is the first to provide strong MRI and clinical evidence in humans that selective inhibition of alpha-4 integrin-mediated leukocyte adhesion and trafficking is an effective approach to the chronic treatment of MS. Both dose levels of the alpha-4 integrin-specific humanized monoclonal antibody natalizumab demonstrated highly statistically significant effects compared with placebo on suppression of new Gd-enhancing inflammatory brain lesions in patients with MS over the six month treatment period. A reduction of these lesions in natalizumab-treated patients was observed one month after the first infusion and was sustained throughout the treatment period. For both dose levels, the reduction was approximately 90 percent, an effect greater than the 50 to 70 percent reduction reported with beta-interferons (MS/MRI Analysis Group, 1995 *Neurology* 4: 1277-1285; Jacobs et al., 1996 *Ann. Neurol.* 39: 285-294; and PRISMS (Prevention of Relapses and Disability by Interferon beta-1a Subcutaneously in Multiple Sclerosis) Study Group, 1998 *Lancet* 352: 1498-1504).

Moreover, the effects of natalizumab on MRI outcomes in this trial are supported by clinical observations. This study was not prospectively powered to show effects on clinical outcomes. Nonetheless, treatment with natalizumab resulted in a significant reduction in relapse rate and a perception of increased well-being among patients. When all reported clinical relapses are considered, both natalizumab groups experienced significantly fewer relapses than the placebo group during six months of treatment. A significant reduction in these episodes was also observed using predefined relapse criteria; a more stringent measure, because it requires a change in objective signs. The effect of natalizumab on relapses exceeds that of the currently approved treatments for MS, which display approximately 30 percent effect (MS/MRI Analysis Group, supra; Jacobs et al., supra; PRISMS Study Group, supra; Johnson et al., 1995 *Neurology* 45: 1268-76).

Importantly, no rebound effects on new MRI lesions or relapses were observed in the natalizumab groups after termination of treatment. Further, monthly infusions of natalizumab for six months were well tolerated, and associated with a safety profile similar to placebo and acceptable for chronic treatment of MS.

The results of this study provide further support for the role of alpha-4 integrin, and the immune cells that express it, in the pathogenesis of acute inflammatory brain lesions in patients with MS. The reduction in new Gd-enhancing lesions was evident after one month of treatment. This observation suggests natalizumab acts early in lesion development by preventing the appearance of new lesions.

In summary, natalizumab has demonstrated strong effects on clinically meaningful parameters in this placebo-controlled trial in patients with relapsing MS. Therapy was well tolerated during this six-month trial. The beneficial effects of natalizumab on the appearance of new inflammatory CNS lesions, the occurrence of clinical relapses and improvement in patient well-being observed in this study indicate the potential for observing effects on disability in the longer term studies currently in progress.

Example 2

Controlled Trial of Natalizumab in Crohn's Disease

Methods

In a double-blind, placebo-controlled trial, 248 patients with moderate to severely active Crohn's disease (CD) were randomized to receive two infusions of placebo or infusion of natalizumab at 3 mg/kg followed by placebo; or two infusions of natalizumab at 3 mg/kg or 6 mg/kg, at a 4-week interval. Outcome measures included the Crohn's Disease Activity Index (CDAI), health-related quality of life (QOL), and serum C-reactive protein levels.

Natalizumab increased the rates of clinical remission and clinical response, and improved QOL in patients with active CD, while demonstrating a safety profile acceptable for treatment of this disease.

Patient Population

After receiving approval from the local ethics committee, each center screened male and female patients of at least 18 years of age who had clinical evidence of moderate to severely active CD defined as a CDAI of at least 220 but less than or equal to 450. Of 311 patients screened, 248 were randomized at thirty-five study centers in Belgium, the Czech Republic, Denmark, Germany, Israel, the Netherlands, Sweden, and the United Kingdom from September 1999 to August 2000. All patients gave informed, written consent. Patients who received methotrexate, cyclosporin, or any investigational agents within 3 months were excluded; patients receiving azathioprine or 6-mercaptopurine were required to have been on a stable dose for at least 4 months. Other exclusions included prior antibody treatment; current use of oral prednisolone at a dose greater than 25 mg/day; current use of an elemental diet or parenteral nutrition; infectious or neoplastic diseases of the bowel; bowel surgery within 3 months; presence of a colostomy, ileostomy, or a colorectostomy with ileorectal anastomosis; symptoms due mainly to the presence of fibrotic strictures; and clinical impression that the patient was likely in the near term to require emergency abdominal surgery.

Study Design and Randomization

Eligible patients were randomly assigned to one of four treatment regimens according to a computer-generated block randomization schedule. Each group received two intravenous infusions spaced by a 4-week interval. The four treatment regimens were two infusions of placebo; one infusion of natalizumab at 3 mg/kg followed by placebo infusion; and two infusions of natalizumab at 3 or 6 mg/kg. The investigator, all other study personnel, and patients were blinded to treatment assignment.

Study Procedures and Endpoints

The primary efficacy endpoint was the proportion of patients in remission (CDAI<150) at week 6. The CDAI incorporates eight related variables: number of liquid or very soft stools per day, severity of abdominal pain or cramping, general well-being, presence of extraintestinal manifestations of disease, presence of an abdominal mass, use of antidiarrheal drugs, hematocrit, and body weight (Best et al., 1976 *Gastroenterology* 70: 439-44]; and Summers et al., 1979 *Gastroenterology* 77: 847-69). Scores less than 150 indicated remission; scores between 150 and 219 indicated mildly active disease, between 220 and 450 indicated moderately active disease, and scores greater than 450 indicated severe activity. Additional prospective endpoints were the proportion of patients demonstrating clinical response (i.e., at least 70 point reduction in CDAI), health-related quality of life, as measured by an inflammatory bowel disease specific questionnaire, the IBDQ (Irvine et al., 1994 *Gastroenterology* 106: 287-96), and serum levels of C-reactive protein.

Safety evaluations including the recording of adverse events and monitoring of clinical laboratories were conducted throughout the study. An independent safety data monitoring committee provided an additional level of monitoring. Serum samples were collected at each visit and analyzed for antibodies against natalizumab by an enzyme linked immunosorbent assay (ELISA).

Statistical Analysis

All efficacy analyses utilized the intent-to-treat (ITT) last observation carried forward (LOCF) population, which comprised all patients randomized (n=248). Patients using rescue medications were classified as treatment failures. The safety population (n=244) comprised those randomized and dosed. Four patients were not dosed due to ineligibility.

All statistical tests were two-sided and at the 5 percent level of statistical significance. Three pair-wise tests of each active treatment compared to placebo were performed. Remission and response rates were analyzed by the Cochran Mantel-Haenszel chi-squared test (general association) (Landis et al., 1978 *Int'l. Stat. Rev.* 46: 237-54) using country as strata. The effect of covariates on remission and response (yes or no) was analyzed at week 6 using logistic regression.

The sample size of 60 subjects per group was calculated to provide 80 percent power at a 5 percent significance level to detect a difference in response rates assuming a 40 percent response rate in the natalizumab groups and a 15 percent response rate in the placebo group.

Two-way analysis of variance models with fixed effects for country and treatment group were used to compare the mean CDAI decreases from base-line. Contrasts comparing each of the active treatment groups to the placebo group were tested.

C-reactive protein and IBDQ data were analyzed using the Wilcoxon-Mann-Whitney test to compare the change from base-line between each of the three active treatment groups and placebo. In a prospectively planned analysis, the C-reactive protein levels were compared for patients with a value above the upper limit of the normal range of 8 mg/l at base-line (week 0).

Results

Demographic characteristics, CDAI scores, site of disease, and medications were comparable among the groups at base-line (Table 4). At the time of the week 0 assessment, most patients were receiving other medications for CD including 5-ASA compounds (48 to 64 percent), oral steroids (46 to 63 percent), or azathioprine/6-mercaptopurine (18 to 37 percent) with or without other agents. Twenty-seven patients withdrew from the study prior to completing 12 weeks: 10 in the placebo group, and 6, 5, and 6 in the 3+0, 3+3, and 6+6 mg/kg natalizumab groups, respectively.

TABLE 4

DEMOGRAPHIC CHARACTERISTICS AND MEDICATIONS AT BASE-LINE

| CHARACTERISTIC | PLACEBO | 3 + 0 MG/KG | 3 + 3 MG/KG | 6 + 6 MG/KG |
|---|---|---|---|---|
| Patients randomized | 63 | 68 | 66 | 51 |
| Mean age and range (yr) | 34 (18-68) | 36 (18-66) | 36 (19-64) | 35 (19-62) |
| Mean disease duration and range (yr) | 8.9 (0.3-64.3) | 8.4 (0.5-27.5) | 8.1 (0.5-22) | 7.8 (0.6-29) |
| Mean base-line CDAI and range* | 300 (186-447) | 288 (211-427) | 298 (219-442) | 296 (210-429) |
| Disease site: | | | | |
| Ileal | 15 (24%) | 9 (13%) | 17 (26%) | 12 (24%) |
| Colonic | 11 (17%) | 16 (24%) | 16 (24%) | 16 (31%) |
| Ileocolonic | 37 (59%) | 43 (63%) | 33 (50%) | 23 (45%) |
| Gender: Female | 33 (52%) | 41 (60%) | 36 (55%) | 26 (51%) |
| Mean weight and range(kg) | 68 (42-100) | 66 (41-95) | 64 (44-97) | 69 (44-98) |
| Concomitant Medications | | | | |
| No concomitant medications* for Crohn's disease | 12 (19%) | 11 (16%) | 9 (14%) | 5 (10%) |
| 5 ASA compounds | 30 (48%) | 40 (59%) | 42 (64%) | 30 (59%) |
| Oral steroids | 31 (49%) | 31 (46%) | 37 (56%) | 32 (63%) |
| Azathioprine or 6-MP (±steroids) | 2 (35%) | 25 (37%) | 17 (26%) | 9 (18%) |

*Eight of 248 patients had a CDAI score < 220 at base-line.
Five of these 8 patients were eligible (CDAI ≥ 220) on the basis of their screening hematocrit, which was the value available at randomization, but had scores < 220 when subsequently recalculated using the base-line hematocrit.
The CDAI scores for the other 3 patients were incorrectly calculated at the time of randomization.
*5 ASAs, steroids, or immunosuppressants.

Clinical Responses, Remissions, and Mean CDAI Scores

The proportion of patients achieving a clinical response (i.e., at least a 70 point reduction in CDAI from base-line) was statistically significantly greater than placebo in all three natalizumab groups at weeks 4, 6, and 8 (Table 5 and FIG. 6), and this effect persisted through week 12 in the two groups that received 2 infusions of natalizumab. Trends for improvement in clinical response rates were observed as early as 2 weeks after the first treatment, and the 3+3 mg/kg natalizumab group demonstrated a statistically significant difference from placebo at this time point. Results for the decrease from base-line in mean CDAI score (Table 6) agree with the response rate findings.

TABLE 5

RATES OF REMISSION AND CLINICAL RESPONSE IN THE ITT POPULATION

| TIME POINT | PLACEBO (N = 63) | 3 + 0 MG/KG NATA-LIZUMAB (N = 68) | 3 + 3 MG/KG NATA-LIZUMAB (N = 66) | 6 + 6 MG/KG NATA-LIZUMAB (N = 51) |
|---|---|---|---|---|
| REMISSION (CDAI < 150) No. OF PATIENTS (%) | | | | |
| Week 2 | 6 (10) | 10 (15) | 13 (20) | 6 (12) |
| P value | | 0.328 | 0.127 | 0.745 |

TABLE 5-continued

RATES OF REMISSION AND CLINICAL RESPONSE IN THE ITT POPULATION

| TIME POINT | PLACEBO (N = 63) | 3 + 0 MG/KG NATA-LIZUMAB (N = 68) | 3 + 3 MG/KG NATA-LIZUMAB (N = 66) | 6 + 6 MG/KG NATA-LIZUMAB (N = 51) |
|---|---|---|---|---|
| Week 4 | 9 (14) | 21 (31) | 19 (29) | 15 (29) |
| P value | | 0.02 | 0.027 | 0.028 |
| Week 6 (prim. endpoint) | 17 (27) | 20 (29) | 29 (44) | 16 (31) |
| P value | | 0.757 | 0.030 | 0.533 |
| Week 8 | 10 (16) | 19 (28) | 27 (41) | 22 (43) |
| P value | | 0.107 | <0.001 | <0.001 |
| Week 12 | 17 (27) | 19 (28) | 28 (42) | 21 (41) |
| P value | | 0.992 | 0.042 | 0.091 |
| RESPONSE (≥70 POINT DROP) No. OF PATIENTS (%) | | | | |
| Week 2 | 19 (30) | 31 (46) | 36 (55) | 22 (43) |
| P value | | 0.081 | 0.004 | 0.136 |
| Week 4 | 18 (29) | 32 (47) | 41 (62) | 27 (53) |
| P value | | 0.029 | <0.001 | 0.006 |
| Week 6 | 24 (38) | 40 (59) | 47 (71) | 29 (57) |
| P value | | 0.022 | <0.001 | 0.039 |
| Week 8 | 22 (35) | 38 (56) | 44 (67) | 28 (55) |
| P value | | 0.018 | <0.001 | 0.028 |
| Week 12 | 27 (43) | 34 (50) | 40 (61) | 33 (65) |
| P value | | 0.503 | 0.033 | 0.018 |

Bold highlights the statistically significant results when compared to placebo.

TABLE 6

DECREASE FROM BASE-LINE IN MEAN CDAI SCORE

| TIME POINT | PLACEBO (N = 63) | 3 + 0 MG/KG NATA-LIZUMAB (N = 68) | 3 + 3 MG/KG NATA-LIZUMAB (N = 66) | 6 + 6 MG/KG NATA-LIZUMAB (N = 51) |
|---|---|---|---|---|
| MEAN DECREASE IN CDAI SCORE FROM BASE-LINE (SD) | | | | |
| Week 2 | 39.3 (73.5) | 63.5 (74.8) | 80.0 (68.9) | 60.5 (68.3) |
| P value vs. placebo | | 0.061 | 0.001 | 0.103 |
| Week 4 | 37.3 (88.8) | 79.9 (89.5) | 100.7 (76.4) | 84.2 (90.5) |
| P value vs. placebo | | 0.004 | <0.001 | 0.003 |
| Week 6 | 49.3 (97.8) | 81.5 (86.1) | 119.4 (79.1) | 97.2 (94) |
| P value vs. placebo | | 0.042 | <0.001 | 0.004 |
| Week 8 | 49.7 (99.5) | 82.4 (87.2) | 117.8 (90.7) | 106.9 (102.9) |
| P value vs. placebo | | 0.053 | <0.001 | 0.001 |
| Week 12 | 63.1 (103.9) | 70.1 (91.7) | 119.2 (111) | 112.5 (96.4) |
| P value vs. placebo | | 0.729 | 0.001 | 0.008 |

Decrease from baseline is defined as (week 0-week n)
SD = standard deviation
Bold highlights the statistically significant results when compared to placebo.

Four weeks after the first treatment, and before patients received the second treatment, all three natalizumab groups had a statistically significantly higher rate of remission compared to patients in the placebo group (Table 5 and FIG. 7). However, at week 6, the prospectively defined primary endpoint, the proportion of patients in clinical remission, was statistically significantly higher only in the 3+3 mg/kg natalizumab group compared to placebo. At week 8, both groups that received two infusions of natalizumab (either 3 or 6 mg/kg) demonstrated statistically significantly higher remission rates compared to placebo. At week 12, the 3+3 mg/kg natalizumab group continued to demonstrate a statistically significant benefit over placebo for clinical remission, while the 6+6 mg/kg group demonstrated a strong trend for benefit over placebo for this outcome.

Predictors of Remission or Response

Using the results at week 6, an analysis was performed to identify base-line variables that may predict remission or clinical response. The variables examined included site of disease, duration of disease, base-line CDAI scores, concomitant use of oral steroids, concomitant use of azathioprine or 6-mercaptopurine, and extraintestinal symptoms. Base-line CDAI score was a significant predictor of remission ($P<0.001$); patients with a higher base-line CDAI were less likely to achieve remission. However, base-line CDAI did not predict the likelihood of response. All other variables analyzed were not significant predictors of remission or response.

Quality of Life

A statistically significant improvement in mean IBDQ scores was observed in all natalizumab treatment groups at week 6 compared to placebo. By week 12, only the treatment groups that received two infusions of natalizumab continued to have IBDQ scores that were significantly higher than the placebo group (Table 7).

TABLE 7

MEAN IBDQ SCORES

| TIME POINT | PLACEBO (N = 63) | 3 + 0 MG/KG NATA-LIZUMAB (N = 68) | 3 + 3 MG/KG NATA-LIZUMAB (N = 66) | 6 + 6 MG/KG NATA-LIZUMAB (N = 51) |
|---|---|---|---|---|
| IBDQ SCORE, MEAN (RANGE) | | | | |
| Week 0 | 130 (66-192) | 130 (52-188) | 136 (79-194) | 123 (55-194) |
| Week 6 | 142 (61-219) | 157 (81-221) | 163 (99-211) | 155 (67-224) |
| P value | | 0.008 | <0.001 | <0.001 |
| Week 12 | 145 (61-217) | 151 (81-221) | 163 (86-221) | 153 (64-215) |
| P value | | 0.486 | 0.021 | 0.014 |

Bold highlights improvements in the IBDQ score when compared to each treatment base-line.

C-Reactive Protein

Patients who had elevated levels of serum C-reactive protein at base-line received periodic assessments of those levels during the trial. Those who received two infusions of natalizumab exhibited a significant decline from base-line in mean serum levels of C-reactive protein compared to patients in the placebo group (FIG. 8). The improvement was maintained through week 12 in patients who received two infusions of 3 mg/kg natalizumab.

Safety and Tolerability

Natalizumab treatment at all dose levels was well tolerated throughout the 12-week study period. Similar numbers of patients from each group withdrew from the study for adverse events (i.e., 2 in the placebo group, 1 in the 3 mg/kg natalizumab group, 2 in the 3+3 mg/kg natalizumab group, and 3 in the 6+6 mg/kg natalizumab group). Overall, 31 patients reported a serious adverse event during the main study phase (i.e., 9 in the placebo group, 8 in the 3 mg/kg natalizumab group, 8 in the 3+3 mg/kg natalizumab group, and 6 in the 6+6 mg/kg natalizumab group). No serious adverse events were assessed as related to study drug and none were fatal; the majority were hospital admissions for complications or symptoms associated with CD. The numbers of patients experiencing treatment-emergent adverse events were similar in the various treatment groups: 52 (83 percent) in the placebo group, 51 (78 percent) in the 3 mg/kg natalizumab group, 57 (88 percent) in the 3+3 mg/kg natalizumab group, and 41 (80 percent) in the 6+6 mg/kg natalizumab group. Table 8 shows adverse events not related to CD with an incidence at least 5 percent greater in a natalizumab group compared to the placebo group. None of these various types of adverse events were statistically significantly different from placebo, and none are deemed to present an unacceptable safety profile for the use of natalizumab in patients with moderate to severe CD.

TABLE 8

ADVERSE EVENTS NOT RELATED TO CROHN'S DISEASE: WITH > 5% INCIDENCE OVER PLACEBO AND OTHER EVENTS OF INTEREST

| PREFERRED TERM | PLACEBO N = 63(%) | 3 + 0 N = 65 | 3 + 3 N = 65 | 6 + 6 N = 51 |
|---|---|---|---|---|
| Chest pain | 0 (0) | 2 (3) | 2 (3) | 4 (8) |
| Conjunctivitis | 0 (0) | 2 (3) | 5 (8) | 0 (0) |
| Dizziness | 0 (0) | 6 (9) | 3 (5) | 0 (0) |
| Fever | 1 (2) | 4 (6) | 3 (5) | 4 (8) |
| Flu syndrome | 6 (10) | 9 (14) | 7 (11) | 10 (20) |
| Headache | 20 (32) | 19 (29) | 27 (42) | 14 (27) |
| Pain | 4 (6) | 4 (6) | 4 (6) | 11 (22) |
| Sinusitis | 0 (0) | 0 (0) | 0 (0) | 3 (6) |
| OTHER EVENTS: | | | | |
| Infusion reaction* | 0 (0) | 0 (0) | 1 (2) | 1 (2) |
| Pts with anti-natalizumab antibodies | 0 (0) | 8 (13) | 4 (6) | 1 (2) |

*Leading to interruption or cessation of infusion.

Anti-natalizumab antibodies were detected in 13 natalizumab-treated patients (7 percent) at week 12. Overall, patients with detectable anti-natalizumab antibodies were no more likely to experience an adverse event or serious adverse event than those who had no detectable anti-natalizumab antibodies.

Two patients experienced infusion reactions; in both, the event occurred during the second infusion. A patient in the 3+3 mg/kg natalizumab group experienced symptoms of mild itching and erythema, and was subsequently found to be positive for anti-natalizumab antibodies. A patient in the 6+6 mg/kg natalizumab group experienced symptoms of mild itching and coughing. These symptoms resolved without treatment, and the patient was subsequently found to be negative for detectable anti-natalizumab antibodies.

Although the prospectively defined primary efficacy endpoint (clinical remission defined as CDAI<150 at week 6) was statistically significantly superior to placebo only for the 3+3 mg/kg natalizumab group, significant benefit over placebo was observed for this outcome at 4 separate time points for the 3+3 mg/kg group (weeks 4, 6, 8, and 12) and two time points for the 6+6 mg/kg group (weeks 4 and 8, with a trend for benefit at week 12). Combined with the findings that the proportions of patients experiencing a clinical response (defined as at least a 70 point drop in CDAI from base-line) were significantly superior to placebo for all three natalizumab groups at the week 4, 6, and 8 time points, and at the week 12 time point for the two treatment groups that received two infusions of natalizumab, these data provide strong evidence for efficacy of natalizumab in the treatment of moderate to severely active CD. Further, the beneficial effects of natalizumab on clinical response and remission rates based on improvements in the CDAI are corroborated by significant improvements in health related QOL, measured by the IBDQ, and improvement in serum C-reactive protein, an acute phase reactant used to quantify generalized inflammation.

The dosage levels of receptor saturation in the CD trial are comparable to the dosages of the MS trial, and thus receptor saturation levels should be comparable in the CD trial. Receptor saturation levels in the CD trial are thus associated with decreased levels of inflammation, as demonstrated by C-reactive protein levels and an improvement in overall patient well-being, as demonstrated by the CDAI.

No serious safety concerns were identified for any of the natalizumab treatment groups. The percentage of patients developing detectable anti-natalizumab antibodies was low, and there were no serious adverse events associated with detectable anti-natalizumab antibodies.

The present study provides compelling evidence for the effectiveness and tolerability of alpha-4 integrin antagonism by natalizumab in the treatment of the clinical signs and symptoms of active moderate to severe CD. In addition, the evidence these data provide that alpha-4 integrin antagonism is an effective mechanism for treating CD raises the possibility that this modality may be more broadly applicable to the treatment of chronic autoimmune and inflammatory diseases.

Example 3

The Effect of Natalizumab on Circulating Activated Leucocytes in Active Inflammatory Bowel Disease The trafficking of leukocyte subsets is involved in the pathogenesis of inflammatory bowel disease (IBD). Because alpha-4 integrins are key mediators of leukocyte migration across the vascular endothelium, being that they are expressed on all leucocytes except neutrophils, the effects of a single 3 mg/kg natalizumab (Antegren®) infusion on basic circulating leukocyte subsets, natural killer (NK) cells and activated T cells in active inflammatory bowel disease patients (IBD). It had also previously been shown that a single 3 mg/kg infusion of natalizumab produced a sustained rise in circulating peripheral blood leucocytes in animals and healthy volunteers ("A six-month weekly intravenous toxicity study with Antegren™ in cynomolgus monkeys with a six-week recovery," *Athena Report* 1998, No. 723-013-098). However, it was unknown whether natalizumab could have differential effects on leukocyte subsets, given that all leucocytes except neutrophils express alpha-4 integrins.

Methods. Leucocytes extracted from peripheral blood of 30 Crohn's disease (CD; 18 natalizumab, 12 placebo) and 10 ulcerative colitis (UC; all received natalizumab—no placebo) patients pre-, 1-, 2-, 4-, 8- and 12-weeks post-infusion were analyzed by fluorescence-activated cell-sorter (FACS). Serum natalizumab levels and disease activity scores were measured at each time-point.

Significant changes compared to baseline (p<0.05) and correlations were tested by Wilcoxon and Spearman tests respectively. Wilcoxon signed rank test for analysis of changes in leukocyte subsets were compared to baseline within treatment groups (p<0.05 denotes significance). Spearman rank correlation tests were used to assess correlation between disease activity parameters, natalizumab levels and leukocyte subsets in those patients receiving natalizumab.

Venous blood was taken immediately prior to natalizumab/placebo infusion and again at one, two, four, eight and twelve weeks post-infusion. The Lymphoprep™ method (Nycomed, Denmark) was used to isolate the peripheral blood lymphocytes (PBLs) prior to analysis by multi-color fluorescence-activated cell sorter (FACS; Becton Dickenson, Oxford, UK) in conjunction with Consort 30 software (Amlot et al., 1996 *Clin. Exp. Immunol.* 105: 176-82). The percentages of PBLs expressing the following markers were measured using FACS analysis: CD I9 (B cell), TCRαβ (T cell), CD3 (pan-T cell), TCRγδ (T cell), CD4 (helper/Th-1 T cell), CD8 (cytotoxic/suppressor T cell) and CD16 (NK cell). The percentages of TCRαβ cells expressing the activation antigens CD38, CD25 chain of interleukin-2 receptor), CD26, CD69 and HLA-DR were measured, in addition to naïve (CD45RA) and memory (CD45RO) T cell subsets and "NK-T cells" (CD57+/CD3+). The percentage of cytotoxic/suppressor T cells (CD8+) expressing the activation antigens CD28 and HLA-DR were also measured.

Results. Eosinophil, monocyte, B and T cell counts were all significantly raised for ≥1 week post-natalizumab. Total lymphocyte counts, both B and T cells, were significantly increased as compared to baseline levels. Neutrophil and basophil counts were unchanged. T cells expressing the activation markers CD25, CD26, HLA-DR, CD8DR, CD8, CD28, CD45RO and CD45RA were significantly raised compared to baseline at ≥4 and 1 week in UC and CD patients respectively. CD38+ and CD69+ T cells were raised at ≥1 week in UC patients only. NK cells were unchanged post-infusion in all patients and NK-type T cells (CD57+) were raised at 1 week in CD patients only. No significant changes in gamma-delta (γδ) T cells were found in CD/UC patients. Changes in T cell subsets did not correlate with disease activity or serum natalizumab levels. The leukocyte changes found post-natalizumab were not detected following placebo.

The lymphocyte counts remained elevated at 4 weeks post-infusion in both Crohn's disease patients (p=0.002) and in those patients with ulcerative colitis (p=0.02), before returning to pre-treatment values at week 8 (Gordon et al., 2002 *Aliment. Pharm. & Ther.* 16: 699-706; and Gordon et al., 2001 *Gastroenterology* 121: 268-74).

The effect of natalizumab on circulating eosinophils and monocytes are shown in FIGS. 9A and 9B. The neutrophil and basophil counts were observed to remain unchanged in all the patient groups studied. FIGS. 10 and 11 demonstrate the effects of natalizumab administration on specific circulating T cell subsets and natural killer cells in Crohn's disease and ulcerative colitis patients. The error bars denote standards of deviation in each chart.

No significant changes in basic leukocyte subsets were detected following placebo infusion. Administration of the placebo to the 11 placebo patients is shown in Table 9. Some changes in lymphocytes expressing activation antigens were detected at isolated time points only in Crohn's patients (Table 10).

TABLE 9

LEUKOCYTE SUBSETS IN PLACEBO-TREATED CROHN'S DISEASE PATIENTS

| Subset Cells × $10^6$/mL | Week 0 Mean | SD | Week 1 Mean | SD | Week 2 Mean | SD | Week 4 Mean | SD | Week 8 Mean | SD |
|---|---|---|---|---|---|---|---|---|---|---|
| Lymphocytes | .60 | .33 | .55 | .36 | .82 | .67 | .48 | .29 | .51 | .31 |
| Neutrophils | .21 | .75 | .18 | .48 | .86 | .36 | .61 | .26 | .91 | .15 |
| Eosinophils | .19 | .16 | .17 | .13 | .15 | .13 | .20 | .12 | .14 | .10 |
| Basophils | .19 | .30 | .14 | .09 | .09 | .07 | .09 | .03 | .08 | .05 |
| Monocytes | .60 | .33 | .55 | .36 | .82 | .67 | .48 | .29 | .51 | .31 |

Mean (SD) leukocyte subset values post-placebo; no significant differences in any group compared to baseline (week 0) values.

TABLE 10

T CELL AND NK MARKERS IN PLACEBO-TREATED CROHN'S DISEASE PATIENTS

| Subset Cells × $10^6$/mL | Week 0 Mean | SD | Week 1 Mean | SD | Week 2 Mean | SD | Week 4 Mean | SD | Week 8 Mean | SD | Week 12 Mean | SD |
|---|---|---|---|---|---|---|---|---|---|---|---|---|
| Lymphocytes | .36 | .57 | .12 | .57 | .83 | .08 | .34 | .98 | .28 | .74 | .62 | .84 |
| TCRαβ+ | .99 | .53 | .81 | .56 | .28 | .88 | .98 | .84 | .95 | .79 | .17 | .81 |
| CD25+ | .18 | .11 | .12 | .07 | .27 | .22 | .17 | .17 | .18 | .15 | .22 | .17 |
| CD26+ | .49 | .32 | .38 | .27 | .80 | .61 | .54 | .49 | .54 | .55 | .58 | .43 |
| CD45RA+ | .74 | .41 | .57 | .39 | .95 | .69 | .68 | .59 | .68 | .57 | .84 | .56 |
| CD45RO+ | .42 | .20 | .31 | *.18* | .50 | .27 | .39 | .24 | .42 | .35 | .50 | .33 |
| CD38+ | .42 | .29 | .31 | *.23* | .46 | *.38* | .35 | .27 | .33 | .25 | .40 | .25 |
| CD69+ | .14 | .20 | .67 | .71 | .13 | .12 | .05 | .04 | .12 | .22 | .10 | .08 |
| HLA-DR+ | .19 | .10 | .15 | .08 | .25 | .20 | .16 | .11 | .17 | .10 | .22 | .16 |
| CD8+ | .11 | .09 | .09 | .06 | .16 | .15 | .09 | .07 | .08 | .05 | .12 | .11 |
| CD8+CD28+ | .21 | .11 | .16 | .11 | .30 | .20 | .22 | .21 | .20 | .18 | .23 | .14 |
| CD8+DR+ | .11 | .09 | .09 | .06 | .16 | .15 | .09 | .07 | .08 | .05 | .12 | .11 |
| CD57+CD3+ | .08 | .06 | .06 | .05 | .10 | .10 | .07 | .04 | .07 | .05 | .10 | .15 |

TABLE 10-continued

T CELL AND NK MARKERS IN PLACEBO-
TREATED CROHN'S DISEASE PATIENTS

| Subset Cells × $10^6$/mL | Week 0 Mean | SD | Week 1 Mean | SD | Week 2 Mean | SD | Week 4 Mean | SD | Week 8 Mean | SD | Week 12 Mean | SD |
|---|---|---|---|---|---|---|---|---|---|---|---|---|
| CD16+CD3− | .11 | .09 | .12 | .09 | .16 | .18 | .09 | .04 | .12 | .12 | .17 | .19 |
| TCRγδ+ | .11 | .16 | .08 | .09 | .18 | .28 | .10 | .13 | .09 | .09 | .11 | .10 |
| KappaMAb+ | .02 | .02 | .03 | .05 | .05 | .08 | .07 | .09 | .03 | .04 | .10 | .01 |

Columns show mean counts (SD) of T cell subsets and NK-type cells of Crohn's study placebo patients compared with baseline values (Wilcoxon signed rank test; p < 0.05). Significant differences compared to baseline are shown in bold. Standard deviations for each mean are shown in italic numbers.

There was no significant correlation between the total lymphocyte counts and disease activity score in either Crohn's disease or ulcerative colitis patients (Tables 11 and 12), nor were any significant correlations found between individual lymphocyte subsets and disease activity. No significant correlation was detected between serum natalizumab levels and changes in leukocyte subsets at one, two or four weeks post-infusion. Natalizumab was undetectable in almost all patients at eight weeks. Thus correlations were not calculated for this time point.

TABLE 11

SPEARMAN R VALUES COMPARING LYMPHOCYTE
SUBSETS AND DISEASE ACTIVITY

| | Crohn's disease | | | Ulcerative colitis | | |
|---|---|---|---|---|---|---|
| Subsets | Week 1 | Week 2 | Week 4 | Week 1 | Week 2 | Week 4 |
| Lymphocytes | 0.16 | −0.37 | −0.01 | −0.63 | −0.19 | 0.03 |
| TCRαβ | 0.26 | −0.29 | 0.05 | −0.59 | −0.39 | 0 |
| CD25 | 0.44 | 0.07 | 0.13 | −0.39 | −0.46 | 0.17 |
| CD26 | 0.31 | −0.22 | −0.11 | −0.39 | −0.29 | 0.10 |
| CD45RA | 0.29 | −0.25 | 0.19 | −0.54 | −0.39 | 0.51 |
| CD45RO | 0.32 | −0.27 | 0.34 | 0.18 | −0.17 | −0.05 |
| CD38 | 0.31 | −0.08 | 0.01 | −0.57 | 0.03 | −0.05 |
| CD69 | −0.32 | 0.12 | 0.12 | −0.15 | 0.28 | 0.12 |
| HLA-DR | 0.19 | −0.05 | −0.01 | 0.12 | −0.13 | 0.15 |
| CD8CD28 | 0.01 | −0.17 | −0.13 | −0.18 | −0.04 | −0.17 |
| CD8DR | 0.11 | −0.19 | −0.18 | −0.1 | 0.07 | 0.24 |
| CD57 | 0.19 | −0.08 | −0.04 | 0.21 | −0.15 | 0.15 |
| CD16 | −0.08 | −0.3 | −0.15 | −0.19 | 0.1 | −0.32 |
| TCRγδ | 0.34 | 0.14 | −0.31 | −0.63 | −0.47 | −0.66 |
| Kappa Mab | −0.11 | −0.02 | −0.2 | 0.05 | −0.27 | 0.19 |

No significant correlation found between lymphocyte subset counts and CDAI (Crohn's disease patients) or Powell-Tuck score (ulcerative colitis).

TABLE 12

SPEARMAN R VALUES COMPARING LYMPHOCYTE
SUBSETS WITH SERUM NATALIZUMAB

| | Crohn's disease | | | Ulcerative colitis | | |
|---|---|---|---|---|---|---|
| Subsets | Week 1 | Week 2 | Week 4 | Week 1 | Week 2 | Week 4 |
| Lymphocytes | 0.03 | 0.49 | 0.64 | 0.1 | −0.02 | 0.18 |
| TCRαβ | −0.11 | 0.35 | 0.51 | −0.04 | 0.28 | −0.11 |
| CD25 | −0.09 | 0.03 | 0.26 | 0.25 | −0.07 | −0.25 |
| CD26 | −0.07 | 0.28 | 0.61 | 0.20 | 0.22 | −0.14 |
| CD45RA | 0.19 | 0.29 | 0.62 | −0.12 | −0.25 | −0.32 |
| CD45RO | −0.16 | 0.32 | 0.34 | 0.37 | 0.08 | 0.39 |
| CD38 | 0.06 | 0.18 | −0.34 | −0.01 | −0.45 | −0.43 |
| CD69 | 0.02 | 0.26 | 0.57 | 0.2 | −0.22 | 0.14 |
| HLA-DR | 0.05 | 0.13 | −0.25 | 0.08 | 0.27 | −0.07 |
| CD8CD28 | −0.18 | 0.16 | 0.41 | 0.25 | 0.07 | 0.32 |
| CD8DR | 0.4 | 0.16 | 0.004 | 0.08 | 0.3 | −0.18 |
| CD57 | 0.1 | −0.06 | −0.31 | −0.08 | 0.03 | 0 |
| CD16 | 0.22 | 0.19 | −0.5 | 0.13 | 0.37 | 0.25 |
| TCRγδ | 0.002 | −0.16 | −0.2 | 0.21 | 0.61 | 0.6 |
| Kappa MAb | −0.07 | −0.27 | 0.29 | 0.41 | 0.45 | −0.41 |

No significant correlation between disease activity and lymphocyte subsets, except for total lymphocyte counts at week 4 (p = 0.04).

Based on the above data, a single 3 mg/kg natalizumab infusion produced increased circulating levels of most, but not all, leukocyte subsets in patients with active IBD. Circulating eosinophil, monocyte and lymphocyte counts were significantly elevated above baseline values for at least four weeks post-infusion in most patients. A wide range of circulating T cell subsets were significantly increased above pretreatment values, particularly those expressing activation antigens. However, NK cell counts (CD16+/CD3−) were not affected by natalizumab, and CD57+ T cells were affected to a much lesser extent by natalizumab than other T cell subsets. Lymphocytes expressing the γδT cell receptor were also not affected by natalizumab, suggesting that alpha-4 integrins are either not expressed, or are expressed at a lower level on these cells.

Thus, in active IBD patients, natalizumab may limit trafficking and maintain in circulation many leukocyte and activated lymphocyte subsets. The NK cells, γδ cells, neutrophils and basophils appear unaffected by the administration of natalizumab, which may suggest that they are less important mediators in the trafficking of these cell types.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention.

All references cited herein are herein incorporated by reference in their entirety for all purposes.

We claim:

1. A method of monitoring a chronic administration regimen for treating pathological inflammation in a subject, wherein the pathological inflammation is modulated by an alpha-4 integrin, comprising chronically administering 300 mg natalizumab or an immunologically active fragment thereof by infusion every four weeks to the patient for a period of at least six months; and detecting levels of brain lesions using an imaging technique.

2. The method of claim 1, wherein the pathological inflammation is caused by multiple sclerosis.

3. The method of claim 1, wherein the method comprises chronically administering 300 mg natalizumab.

4. The method of claim 3, wherein the imaging technique is magnetic resonance imaging (MRI).

5. The method of claim 4, wherein the pathological inflammation is caused by multiple sclerosis.

6. The method of claim 5, wherein the method comprises detecting presence or absence of new lesions in the central nervous system using MRI.

7. The method of claim 5, wherein the method comprises detecting Gd-enhancing brain lesions.

* * * * *

SEQUENCE LISTING

<160> NUMBER OF SEQ ID NOS: 9

<210> SEQ ID NO 1
<211> LENGTH: 13
<212> TYPE: PRT
<213> ORGANISM: Influenza virus
<220> FEATURE:
<223> OTHER INFORMATION: Influenza Hemagluttinin

<400> SEQUENCE: 1

Pro Lys Tyr Val Lys Gln Asn Thr Leu Lys Leu Ala Thr
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      PADRE T-cell epitopes
<220> FEATURE:
<221> NAME/KEY: MOD_RES
<222> LOCATION: (3)..(3)
<223> OTHER INFORMATION: cyclohexylalanine, tyrosine or phenylalanine

<400> SEQUENCE: 2

Ala Lys Xaa Val Ala Ala Trp Thr Leu Lys Ala Ala Ala
1               5                   10

<210> SEQ ID NO 3
<211> LENGTH: 16
<212> TYPE: PRT
<213> ORGANISM: Plasmodium sp.
<220> FEATURE:
<223> OTHER INFORMATION: Malaria CS

<400> SEQUENCE: 3

Glu Lys Lys Ile Ala Lys Met Glu Lys Ala Ser Ser Val Phe Asn Val
1               5                   10                  15

<210> SEQ ID NO 4
<211> LENGTH: 10
<212> TYPE: PRT
<213> ORGANISM: Hepatitis B virus

<400> SEQUENCE: 4

Phe Phe Leu Leu Thr Arg Ile Leu Thr Ile
1               5                   10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      heat shock protein 65 T-cell epitope

<400> SEQUENCE: 5

Asp Gln Ser Ile Gly Asp Leu Ile Ala Glu Ala Met Asp Lys Val Gly
1               5                   10                  15

Asn Glu Gly

<210> SEQ ID NO 6
<211> LENGTH: 14
<212> TYPE: PRT
<213> ORGANISM: Mycobacterium tuberculosis
<220> FEATURE:

```
<223> OTHER INFORMATION: Bacille Calmette-Guerin

<400> SEQUENCE: 6

Gln Val His Phe Gln Pro Leu Pro Pro Ala Val Val Lys Leu
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      Tetanus toxoid

<400> SEQUENCE: 7

Gln Tyr Ile Lys Ala Asn Ser Lys Phe Ile Gly Ile Thr Glu Leu
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      Tetanus toxoid

<400> SEQUENCE: 8

Phe Asn Asn Phe Thr Val Ser Phe Trp Leu Arg Val Pro Lys Val Ser
1               5                   10                  15

Ala Ser His Leu Glu
            20

<210> SEQ ID NO 9
<211> LENGTH: 16
<212> TYPE: PRT
<213> ORGANISM: Human immunodeficiency virus

<400> SEQUENCE: 9

Lys Gln Ile Ile Asn Met Trp Gln Glu Val Gly Lys Ala Met Tyr Ala
1               5                   10                  15
```